US008338154B2

(12) United States Patent
Inokuchi et al.

(10) Patent No.: US 8,338,154 B2
(45) Date of Patent: Dec. 25, 2012

(54) MUTANT GLYCOPROTEIN RESISTANT TO MODIFICATION WITH ASPARAGINE-LINKED SUGAR CHAIN

(75) Inventors: Jin-ichi Inokuchi, Sendai (JP); Satoshi Uemura, Sendai (JP)

(73) Assignee: Seikagaku Corporation, Chiyoda-ku, Tokyo (JP)

( * ) Notice: Subject to any disclaimer, the term of this patent is extended or adjusted under 35 U.S.C. 154(b) by 157 days.

(21) Appl. No.: 12/943,461

(22) Filed: Nov. 10, 2010

(65) Prior Publication Data

US 2011/0124082 A1 May 26, 2011

Related U.S. Application Data

(62) Division of application No. 11/658,103, filed as application No. PCT/JP2005/013424 on Jul. 21, 2005, now abandoned.

(30) Foreign Application Priority Data

Jul. 21, 2004 (JP) ................................ 2004-213616

(51) Int. Cl.
*C12N 9/10* (2006.01)
*C12P 21/02* (2006.01)
*C07K 14/435* (2006.01)

(52) U.S. Cl. ........................ 435/193; 435/69.1; 530/350

(58) Field of Classification Search .................. 435/193, 435/69.1; 530/350
See application file for complete search history.

(56) References Cited

U.S. PATENT DOCUMENTS 6,555,371 B1 * 4/2003 Saito ............................ 435/325

FOREIGN PATENT DOCUMENTS

| | | |
|---|---|---|
| EP | 1 695 982 A1 | 8/2006 |
| WO | WO 93/18157 | 9/1993 |
| WO | WO 95/04816 | 2/1995 |

OTHER PUBLICATIONS

Result 1, search of Jun. 12, 2012 in issued patents protein database, alignment of instant Seq ID No:4 with Seq ID No:2 of Saito, US 6,555,371.*

Oriol, Database DDBJ/EMBL/Genbank online, Accession No. NP_955810, uploaded Jan. 21, 2004, retrieved Apr. 11, 2011 http://www.ncbl.nlm.nih.gov/protain/41054812?sat=OLD03&satkev=6850534, pp. 1-5 only.

Notice of Reason for Rejection dated Apr. 19, 2011 issued to corresponding Japanese Patent Application No. 2006-529283.

(Continued)

*Primary Examiner* — Rosanne Kosson

(74) *Attorney, Agent, or Firm* — Knobbe, Martens, Olson & Bear, LLP

(57) ABSTRACT

To obtain a mutant protein of an asparagine-linked glycoprotein, which has no N-linked sugar chain under ordinary circumstance, and remains a physiological activity of the glycoprotein before the mutation was introduced, at least one of the amino acids contained in the amino acid sequence motif (I) and/or (II) in the polypeptide of the asparagine-linked glycoprotein is substituted into another amino acid: (I) Asn Xa1 Xa2 (II) Xa3 Val Gly Asn Xa1 Xa2. In amino acid sequence motif (I) and (II), Xa1 represents an amino acid other than Pro, Xa2 represents Thr or Ser and Xa3 represents His or Asp.

8 Claims, 19 Drawing Sheets

OTHER PUBLICATIONS

"Ganglioside GM3 Synthase," Database UniProt [Online], Jul. 5, 2004, retrieved from EBI accession No. UNIPROT:Q705K5.

"Role of N-linked Glycans of Ganglioside GM3 Synthase (SAT-I)," Database Biosis [Online], Nov. 2003, Database accession No. PREV200300585066.

Jeanneau, et al. "Structure-Function Analysis of the Human Sialyltransferase ST3Gal I—Role of *N*-Glycosylation and a Novel Conserved Sialylmotif," *The Journal of Biological Chemistry*, vol. 279, No. 14, pp. 13461-13468, Apr. 2, 2004.

Chen, et al. "Minimal Structural and Glycosylation Requirements for ST6Gal I Activity and Trafficking," *Glycobiology*, vol. 10, No. 5, pp. 531-538, May 2000.

Close, et al. "Polysialyltransferase-1 Autopolysialylation is not Requisite for Polysialylation of Neural Cell Adhesion Molecule," *The Journal of Biological Chemistry*, vol. 275, No. 6, pp. 4484-4491, Feb. 11, 2000.

Close, et al. "The Polysialyltransferase ST8Sia II/STX: Post-translational Processing and Role of Autopolysialylation in the Polysialylation of Neural Cell Adhesion Molecule," *Glycobiology*, vol. 11, No. 11, pp. 997-1008, Nov. 2001.

Uemura, et al. "Substitution of the *N*-glycan Function in Glycosyltransferases by Specific Amino Acids: ST3Gal-V as a Model Enzyme," *Glycobiology*, vol. 16, No. 3, pp. 258-270, Mar. 2006.

Uemura, et al. "Role of N-Linked Glycans of Ganglioside GM3 Synthase (SAT-I)," *Glycobiology*, vol. 13, No. 11, pp. 855-856, Nov. 2003.

GenBank record No. NP_006002, Protein database record for ST8 alpha-N-Acetyl-neuraminide alpha-2,8-sialyltransferase 2 [*Homo sapiens*], especially reference 6, printed on May 3, 2010.

Vance, et al. "Distinct but Dispensable N-Glycosylation of Human CD69 Proteins," *Archives of Biochemistry and Biophysics*, vol. 368, No. 2, pp. 214-220, Aug. 15, 1999.

Mühlenhoff, et al., "The Impact of *N*-Glycosylation on the Functions of Polysialyltransferases," *The Journal of Biological Chemistry*, vol. 276, No. 36, pp. 34066-34073, Sep. 7, 2001.

Oka, et al. "Idenshi Sosa o Mochiita Tosa no Sakujo Oyobi Kaihen," *Protein, Nucleic acid, and Enzyme*, vol. 37, No. 3, pp. 389-394, 1992 with English translation, English language portion only.

Martina, et al. "Influence of *N*-Glycosylation and *N*-Glycan Trimming on the Activity and Intracellular Traffic of GD3 Synthase," *The Journal of Biological Chemistry*, vol. 273, No. 6, pp. 3725-3731, Feb. 6, 1998.

Eckhardt, et al. "N-Glycosylation is Required for Full Enzymic Activity of the Murine Galactosylceramide Sulphotransferase," *The Journal of Biological Chemistry*, vol. 368, pp. 317-324, 2002.

Ishii, et al. "Expression Cloning and Functional Characterization of Human cDNA for Ganglioside $G_{M3}$ Synthase," *The Journal of Biological Chemistry*, vol. 273, No. 48, pp. 31652-31655, Nov. 27, 1998.

Kono, et al. Molecular Cloning and Functional Expression of a Fifth-Type α2,3-Sialyltransferase (mST3Gal V: GM3 Synthase), *Biochemical and Biophysical Research Communications*, vol. 253, pp. 170-175, 1998.

Datta, et al. "What is the Function of the Sialyltransferase "Sialylmotif"?," *Trends in Glycoscience and Glycotechnology*, vol. 7, No. 34, pp. 129-130, Mar. 1995.English language portion only.

Office Action dated Aug. 30, 2011 issued to corresponding Japanese application No. 2006-529283, pp. 8-10 only.

\* cited by examiner

```
hSAT-I    1   MRRPSLLLKDILKCT----LLVFGVWILYILKENYTTEECDMKRMHY-VD
mSAT-I    1   MRRPSLLIKDICKCT----LVAFGVWLLYILILNYTABECDMKRMHY-VD
zSAT-I    1   MRR--VMKQSSCYFSKETMILLSLALMSLAFLKLPSFHTELKPVEVPVD hSAT-I   46   PDRVKRAQKYAQQVLQKECRPKFAKTSMALLFEHRYSVDLLPFVQKAPKD
mSAT-I   46   PDRIKRAQSYAQEVLQKECRPRYAKTAMALLFEDRYSINLEPFVQKVPTA
zSAT-I   49   NKFRKRVHSHVREILDKECRPSFARQRMVT-EHHGSTPTIDPFLNKNMKL hSAT-I   96   SEAESKYDPPEGFRKFSSKVQTLLELLPEHDLPEHLKAKTCRRCVVIGSG
mSAT-I   96   SEAELKYDPPEGFRKFSSKVQSLDMLPEHDFPEHLRAKACKRCVVGNG
zSAT-I   98   DEQIFQYPPPEGFLDMKNKLEEILNLPVSSE-QRLGERDCRRCVVGNC hSAT-I  146   GILHGLELGHTLNQFDVVIRLNSAPVEGYSEHVGNKTIRMTYPEGAPLS
mSAT-I  146   GILHGLELGHALNQFDVVIRLNSAPVEGYSEHVGNKTIIRMTYPEGAPLS
zSAT-I  147   GILKGLGLGHLLNREDIIIRLNSGPLQDFSADVGNRTTIRMSYPESCPKV hSAT-I  196   DLEYYSNDLFVAVLFKSVDFNWLQAMVKKETLPFWVRLFFWKQVAEKIPL
mSAT-I  196   DVEYYANDLFVTLFKSVDFKWLQAMVRLFFWKQVAEKVPL
zSAT-I  197   WEDTDPDLKYAVIFKSVDFHWLRAMISRTPVSLWDRLFFWQNVPMSVPV hSAT-I  246   QPKHFRILNPVIKETAFDILQYSEPQSRFWGRDKNVPTIGVIAVVIATH
mSAT-I  246   QPKHFRILNPVIKETAFDILQYSEPQSRFWGHDKNIPIGVIAVVIATH
zSAT-I  247   KTSQFHLLNPQIREMALDLLNYPEEKKRLWSWDONIPTLGLTALNLATY hSAT-I  296   LCDEVSLAGFGYDLNQPRTPLHYFDSQCMAAMNFQTMHNVITETKFLLKL
mSAT-I  296   LCDEVSLAGFGYDLSQPRTPLHYFDSQCMGAMHWQVMHNVITETKFLLKL
zSAT-I  297   ICDEVSLAGFGYNLSQKEAPLHYDSVPMTTILKEAMHNVQKETVETLKRL hSAT-I  346   VKEGVVKDLSGGIDREF-    (SEQ ID NO:42)
mSAT-I  346   LKEGVVEDLSGGIH----    (SEQ ID NO:4)
zSAT-I  347   VASGSITDLTGGIHCSFC    (SEQ ID NO:41)
```

Fig.1

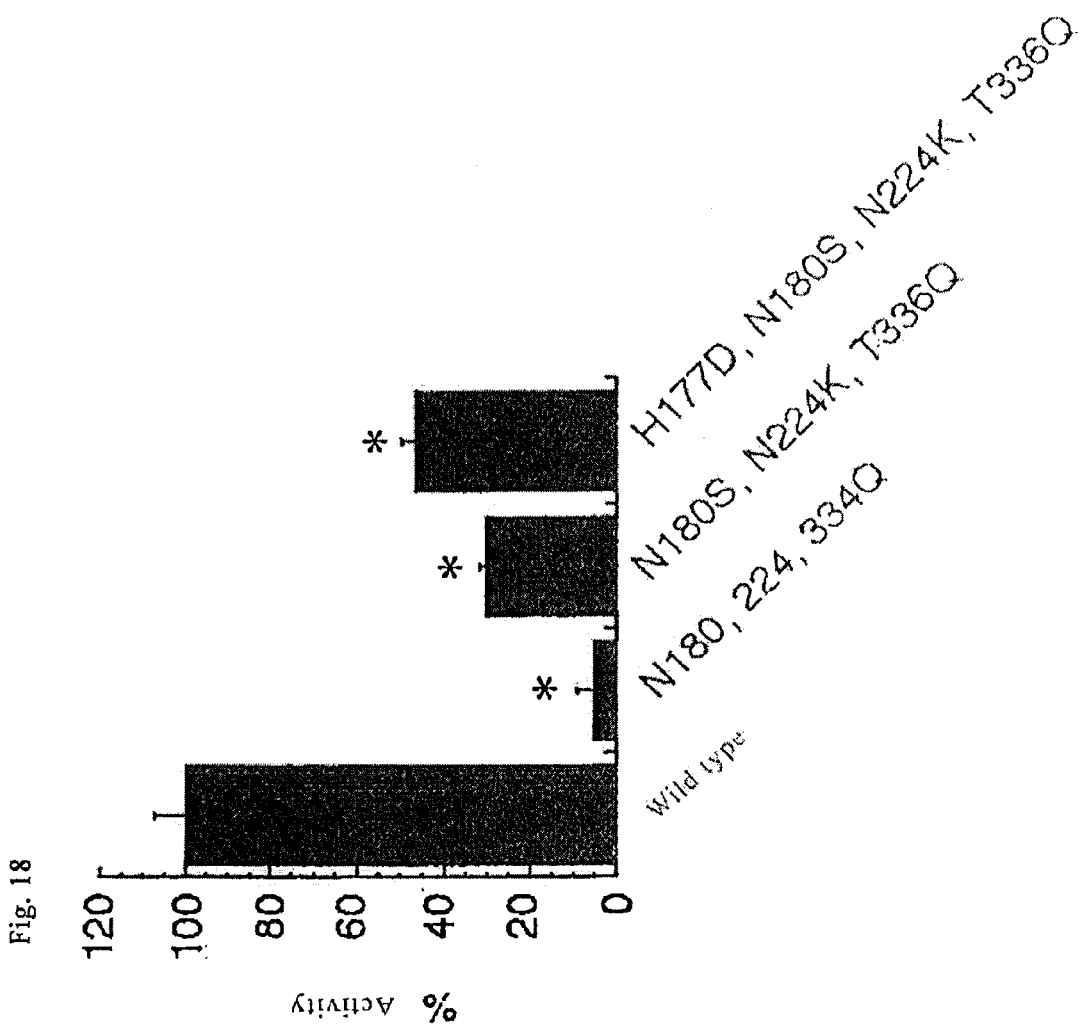
Fig. 18
Fig. 19
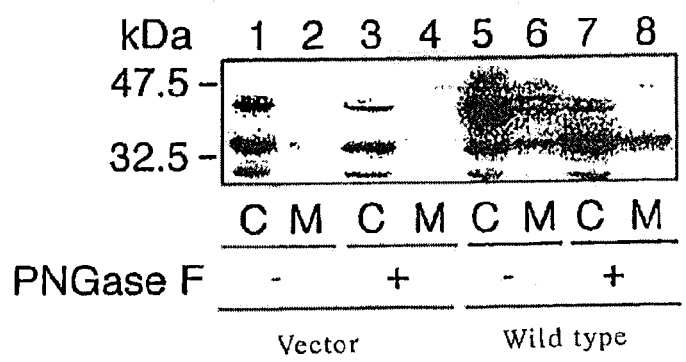

MUTANT GLYCOPROTEIN RESISTANT TO MODIFICATION WITH ASPARAGINE-LINKED SUGAR CHAIN

RELATED APPLICATIONS

This application is a divisional of U.S. application Ser. No. 11/658,103, filed Jan. 22, 2007, which is the U.S. National Phase under 35 U.S.C. §371 of International Application PCT/JP2005/013424, filed Jul. 21, 2005, which was published in a language other than English which claims priority of JP Application No. 2004-213616, filed Jul. 21, 2004.

TECHNICAL FIELD

The present invention relates to a mutant protein of an asparagine-linked glycoprotein, which has no N-linked sugar chain and retains a physiological activity of a glycoprotein before the mutation was introduced, and a method of producing the same.

BACKGROUND ART

First, abbreviations used in the specification are explained.
BPB: bromophenol blue
CMP: cytidine 5'-monophosphate
EDTA: ethylenediamine tetraacetic acid
EGTA: ethylene glycol bis(2-aminoethyl ether)-N,N,N',N'-tetraacetic acid
Endo H: endo-β-N-acetylglucosaminidase H
ER: endoplasmic reticulum
FBS: fetal bovine serum
HRP: horseradish peroxidase
HPTLC: high performance thin-layer chromatography
LacCer: lactosylceramide
N-linked sugar chain: asparagine-linked sugar chain
N-linked glycoprotein: asparagine-linked glycoprotein
PBS: phosphate-buffered saline
PCR: polymerase chain reaction
PMSF: phenylmethanesulfonyl fluoride
PNGase F: peptide-N(4)-(N-acetyl-β-D-glucosaminyl) asparagine amidase
PVDF: polyvinylidene difluoride
SAT-I: sialyltransferase-I
hSAT-I: human SAT-I
mSAT-I: mouse SAT-I
zSAT-I: zebrafish SAT-I
SDS: sodium dodecyl sulfate
SDS-PAGE: sodium dodecyl sulfate-polyacrylamide electrophoresis Further, in the specification, an amino acid X (one-letter notation) which is at the J-th position from the N-terminal of a protein is represented as "XJ". For example, Asn at the 180th position from the N-terminal is represented as "N180" and Thr at the 336th position from the N-terminal is represented as "T336".

Further, in the specification, a protein obtained by substituting an amino acid X (one-letter notation) at the J-th position from the N-terminal of a protein by an amino acid Z (one-letter notation) is represented as "XJZ". For example, a protein in which His at the 177th position from the N-terminal is substituted by Asp is represented as "H177D" and a protein in which Asn at the 224th position from the N-terminal is substituted by Lys is represented as "N224K". Further, when substitution of one amino acid by another occurs at a plurality of sites, the substitutions are represented side by side. For example, a protein in which His at the 177th position from the N-terminal is substituted by Asp and Asn at the 224th position from the N-terminal is substituted by Lys is represented as "H177D, N224K".

Most of secretory proteins in a living body are considered to be present as glycoproteins. Sugar chains have a wide variety of functions such as physical stabilization of proteins, expression of enzyme activity, cell adhesion, metastasis of cancer, signal transduction, subcellular localization, microbial infection, and immune response. Therefore, lack of the sugar chains to be linked to glycoproteins, in many cases, causes effects such as failure or reduction of expression of physiological activity of the glycoprotein.

An N-linked sugar chain, which is a sugar chain to be linked to a glycoprotein, is known to link to Asn in a consensus sequence comprising Asn-Xaa-Ser/Thr (provided that Xaa is an amino acid other than Pro) of a protein.

It is also known that a glycosyltransferase is one of glycoproteins, and a plurality of N-linked sugar chains are linked to most of glycosyltransferases. It has been reported that a glycosyltransferase wherein N in said consensus sequence is substituted by Q, which is structurally most similar to N, and a glycosyltransferase treated with tunicamycin, which inhibits formation of dolichol pyrophosphate-N-acetylglucosamine to suppress sugar transfer to a protein, have a remarkably reduced enzymatic activity (Non-patent Document 1 and Non-patent Document 2).

For example, α1,3-fucosyltransferase (Fuc) III, IV, V and VI, α2,3-sialyltransferase (ST3Gal I), α2,6-sialyltransferase (ST6Gal I), α2,8-sialyltransferase (ST8Sia I); GD3 synthase, UDP-N-acetylglucosamine:β-D-mannoside β1,4-N-acetylglucosaminyltransferase III (GnT III), core 2β1,6-N-acetylglucosaminyltransferase (C2 GnT), galactosylceramide sulfotransferase (CST), N-acetylgalactosaminyltransferase 1 (GalNac-T), β1,3-galactosyltransferase (Gal-T2), UDP-glucuronosyltransferase 2B (UGT2B) and the like are reported to require sugar chains to express their enzymatic activities.

SAT-I is one of sialyltransferases (i.e., sialic acid transferases) that transfer sialic acid to lactosylceramide and synthesizes GM3, and hSAT-I, mSAT-I and zSAT-I have been cloned (Non-patent Document 3 and Non-patent Document 4). In addition, SAT-Is from dog, bovine, rat, chicken, medaka, and tetradon have been cloned.

However, in N-linked glycoproteins, a mutant protein is not known which has no N-linked sugar chains to be linked thereto, but retains a physiological activity of a glycoprotein before the mutation is introduced. Neither is a method of producing such a mutant protein and the like.
Non-patent Document 1: Martina J. A. et al., 1998, The Journal of Biological Chemistry, vol. 273, p. 3725-3731
Non-patent Document 2: Eckhardt M. et al., 2002, The Biochemical Journal vol. 368, p. 317-324
Non-patent Document 3: Ishii A. et al., 1998, The Journal of Biological Chemistry, vol. 273, p. 31652-31655
Non-patent Document 4: Kono M. et al., 1998, Biochemical and Biophysical Research Communications, vol. 253, p. 170-175

SUMMARY OF THE INVENTION

If a physiological activity of a glycoprotein is expressed in a state where a sugar chain to be linked to the glycoprotein is absent, a protein which has the physiological activity equivalent to that of the glycoprotein can be produced conveniently, rapidly, in large amounts and at low cost and its quality can be kept constant. Therefore, it is an object of the present invention to provide a mutant protein of an N-linked glycoprotein, which lacks an N-linked sugar chain to be linked, but retains the physiological activity of the glycoprotein, and to provide a method of producing the same.

The inventors of the present invention made an intensive effort to achieve the above-mentioned objects and as a result, they have found that substitution of an amino acid in a specified amino acid sequence in the polypeptide of an N-linked glycoprotein by other amino acid allows the glycoprotein to retain the function of the glycoprotein before the mutation is introduced even in a state where N-linked sugar chains are absent, thereby accomplishing the present invention.

Thus, the present invention provides a mutant protein (hereinafter, referred to as "the protein of the present invention") comprising an amino acid sequence of N-linked glycoprotein having the amino acid sequence motif (I) and/or (II) shown below, wherein at least one amino acid selected from the amino acids in the amino acid sequence motif (I) and/or (II) is substituted by other amino acid, and wherein the amino acid sequence containing the substituted amino acids is not subject to modification with N-linked sugar chain and an activity is maintained:

(I) Asn Xa1 Xa2 (SEQ ID NO: 1); and (II) Xa3 Val Gly Asn Xa1 Xa2 (SEQ ID NO: 2)

(Xa1 indicates an amino acid other than Pro, Xa2 indicates Thr or Ser, and Xa3 indicates His or Asp in the amino acid sequence motif (I) and (II)).

Further, the amino acid substitution in the amino acid sequence motif (I) and/or (II) is preferably one or more substitutions (A) to (C) described below:

(A) substitution of Asn by Lys or Ser;

(B) substitution of Xa2 by Gln; and (C) substitution of Xa3 by Asp.

Further, the glycoprotein is preferably an enzyme, more preferably a glycosyltransferase, in particular a sialic acid transferase.

Further, the sialyltransferase is preferably SAT-I, and in SAT-I, the amino acid sequence motif (I) is preferably an amino acid sequence (i) and/or (ii) described below, and the amino acid sequence motif (II) is preferably an amino acid sequence (iii) described below:

(i) Asn Glu Ser;

(ii) Asn Val Thr; and (iii) His Val Gly Asn Lys Thr (SEQ ID NO: 43).

Further, the amino acid substitution in the amino acid sequences (i) to (iii) preferably includes one or more substitutions (a) to (d):

(a) substitution of Asn by Lys in the amino acid sequence (i);

(b) substitution of Thr by Gln in the amino acid sequence (ii);

(c) substitution of Asn by Ser in the amino acid sequence (iii); and (d) substitution of His by Asp in the amino acid sequence (iii).

Further, the amino acid sequence of SAT-I before the mutation is introduced preferably has the amino acid sequence of SEQ ID NO: 4 or an amino acid sequence having homology of 80% or more with an amino acid sequence of SEQ ID NO: 4.

Further, the mutant SAT-1 is, in particular, preferably a protein having the following amino acid sequence.

the amino acid sequence of SEQ ID NO: 6.

the amino acid sequence of SEQ ID NO: 8.

the amino acid sequence of SEQ ID NO: 10.

the amino acid sequence of SEQ ID NO: 12.

the amino acid sequence of SEQ ID NO: 14.

the amino acid sequence of SEQ ID NO: 16.

the amino acid sequence of SEQ ID NO: 18.

Further, the present invention provides a polynucleotide encoding the protein of the present invention (hereinafter, referred to as "the polynucleotide of the present invention").

Further, the present invention provides a method of producing a mutant protein that retains an activity (hereinafter, referred to as "the method of the present invention"), comprising:

comparing, in an amino acid sequence of an asparagine-linked glycoprotein having the amino acid sequence motif (I) and/or (II) shown below, the amino acid sequence motif (I) and/or (II) described below or an amino acid sequence comprising the amino acid sequence motif (I) and/or (II) with a corresponding protein from another organism, or with a corresponding amino acid sequence of another protein which is from the same organism as the glycoprotein and which belongs to the same protein family as the glycoprotein to clarify differences between the amino acid sequences; and substituting the different amino acids by corresponding amino acids of the target of comparison, wherein the amino acid sequence comprising the substituted amino acids undergoes no modification by an asparagine-linked sugar chain:

(I) Asn Xa1 Xa2 (SEQ ID NO: 1); and (II) Xa3 Val Gly Asn Xa1 Xa2 (SEQ ID NO: 2)

(Xa1 indicates an amino acid other than Pro, Xa2 indicates Thr or Ser, and Xa3 indicates His or Asp in the amino acid sequence motif (I) and (II)).

Further, in the method of the present invention, the amino acid substitution in the amino acid sequence motif (I) and/or (II) is preferably one or more substitutions (A) to (C):

(A) substitution of Asn by Lys or Ser;

(B) substitution of Xa2 by Gln; and (C) substitution of Xa3 by Asp.

Further, the method of the present invention is preferably applied to an enzyme, more preferably to a glycosyltransferase, in particular to a sialic acid transferase.

The method of the present invention is preferably adapted to SAT-I among sialic acid transferases and in the SAT-I, the amino acid sequence motif (I) is preferably an amino acid sequence (i) and/or (ii) described below, and the amino acid sequence motif (II) is preferably an amino acid sequence (iii) described below:

(i) Asn Glu Ser;

(ii) Asn Val Thr; and (iii) His Val Gly Asn Lys Thr (SEQ ID NO: 43).

BRIEF DESCRIPTION OF THE DRAWINGS

FIG. 1 is a drawing showing a comparison among amino acid sequences of hSAT-I, mSAT-I, and zSAT-I. In FIG. 1, the dotted crossbar line portion indicates a transmembrane region, the first solid crossbar line portion indicates a sialyl motif L, the second solid crossbar line portion indicates a sialyl motif S, and the third solid crossbar line portion indicates a sialyl motif VS. A boxed portion indicates the portion to which an N-linked sugar chain can be linked (i.e., N-glycosylation site).

FIG. 2 is a diagram (photograph) showing immunoblotting of cell lysates expressing mSAT-I.

FIG. 3 is a diagram (photograph) showing immunoblotting of cell lysates expressing mSAT-I in the presence of tunicamycin (Tuni.), Kifnecin (Kif.), or castanospermine (Cas.).

FIG. 4 is a diagram showing the SAT-I activity of the lysate used in FIG. 3. "*" indicates a significant difference with respect to the wild type at $p<0.001$.

FIG. 5 is a diagram (photograph) showing immunoblotting of cell lysates of expressing the mSAT-I mutant.

FIG. 6 is a diagram (photograph) showing immunoblotting of Endo H-treated cell lysates expressing the mSAT-I mutant.

FIG. 7 is a diagram (photograph) showing immunoblotting of PNGase F-treated cell lysates expressing the mSAT-I mutant.

Figure 10:
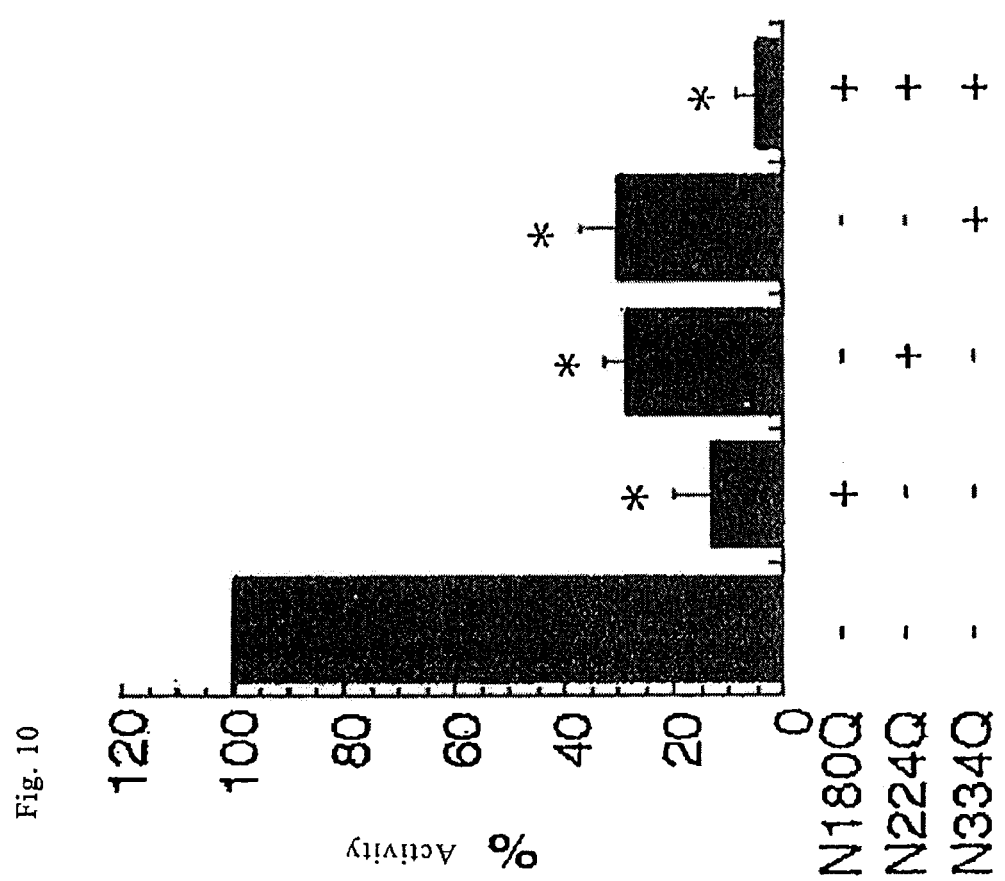
Figure 11:
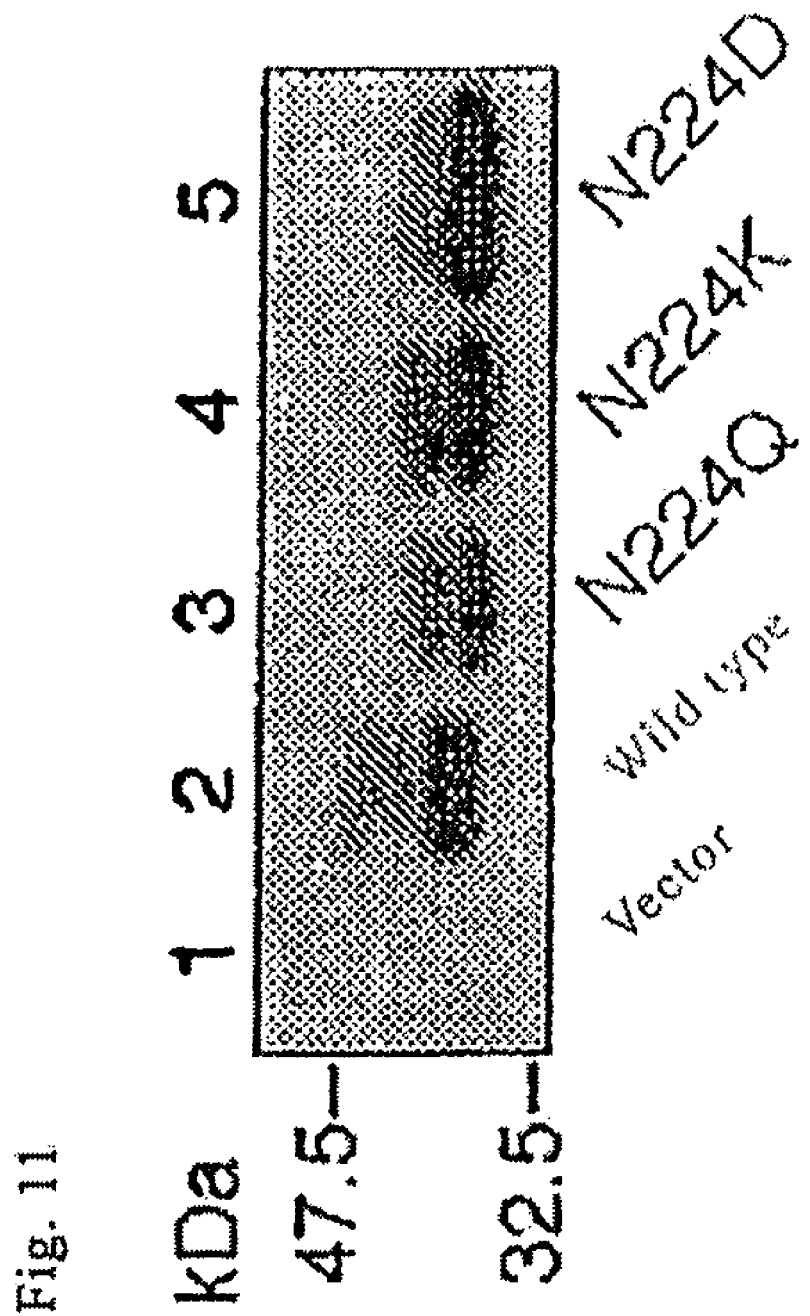
Figure 12:
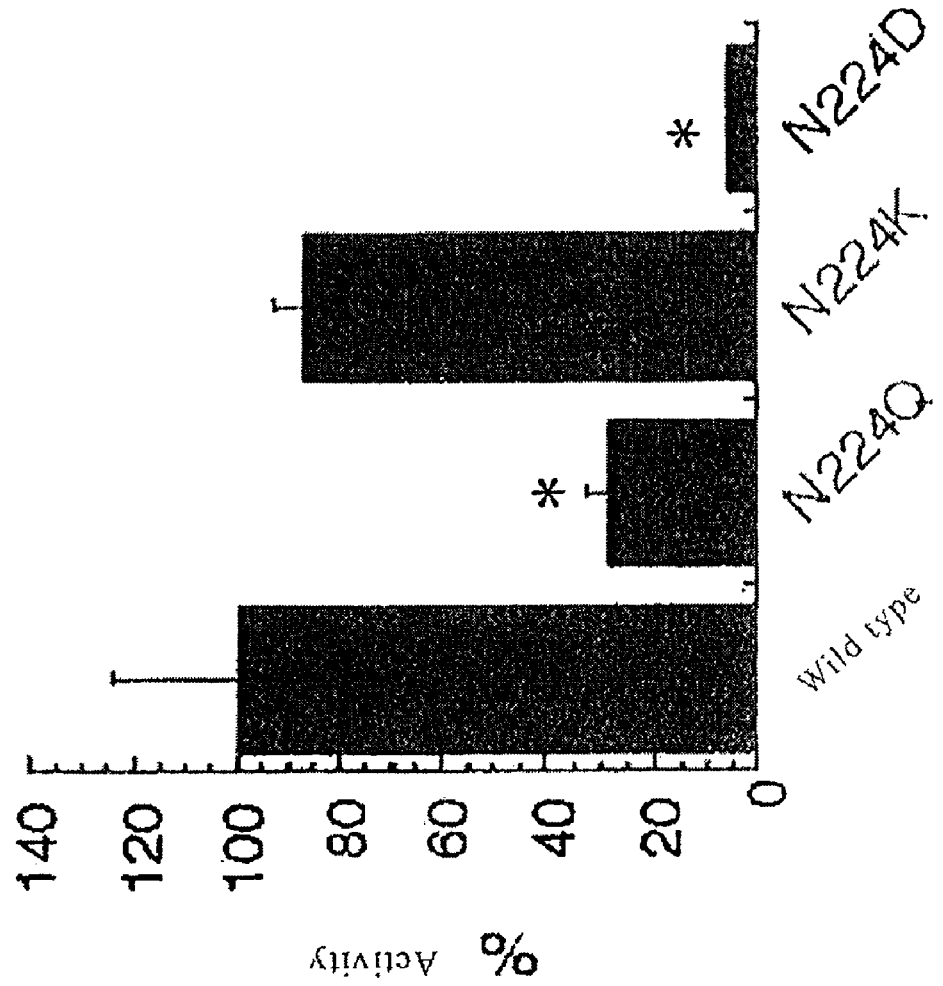
Figure 13:
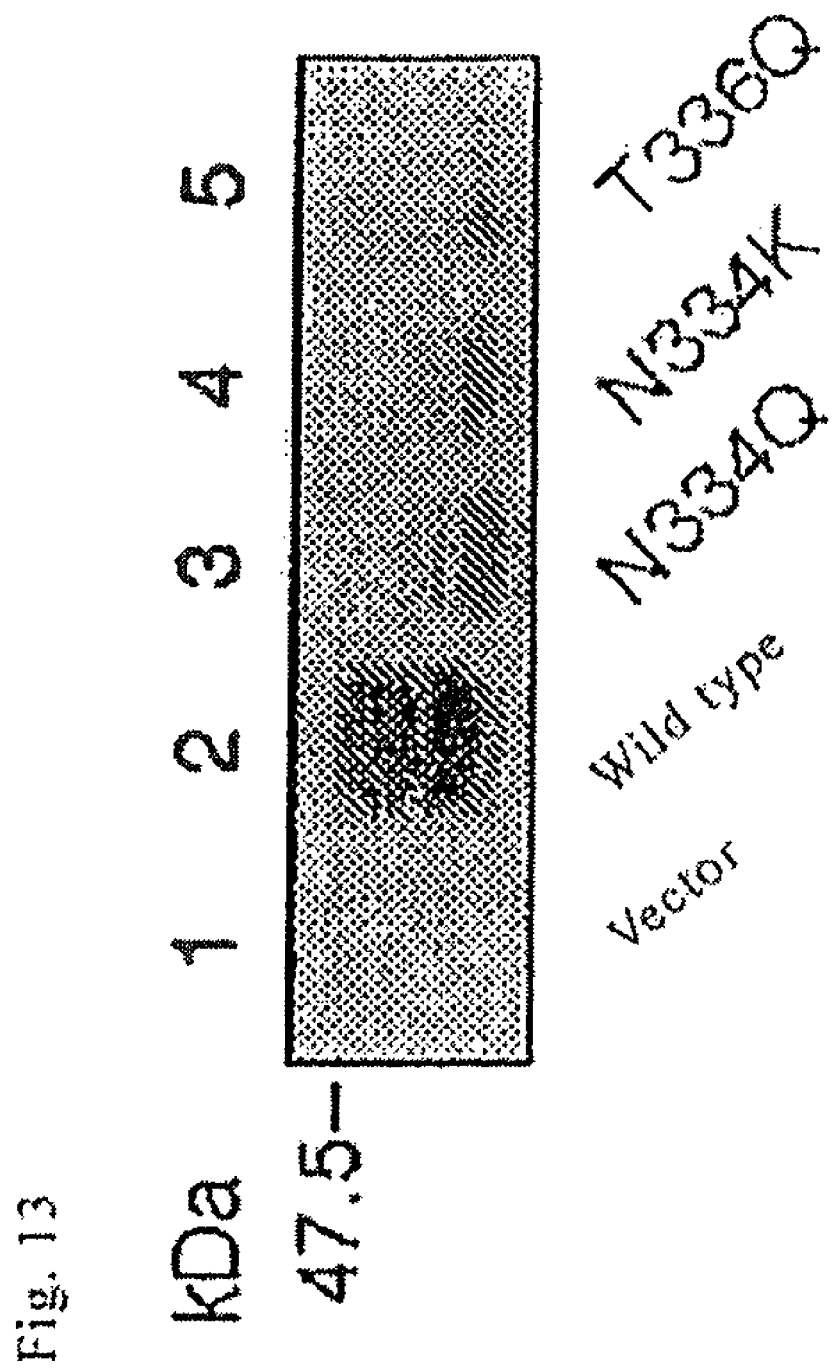
Figure 14:
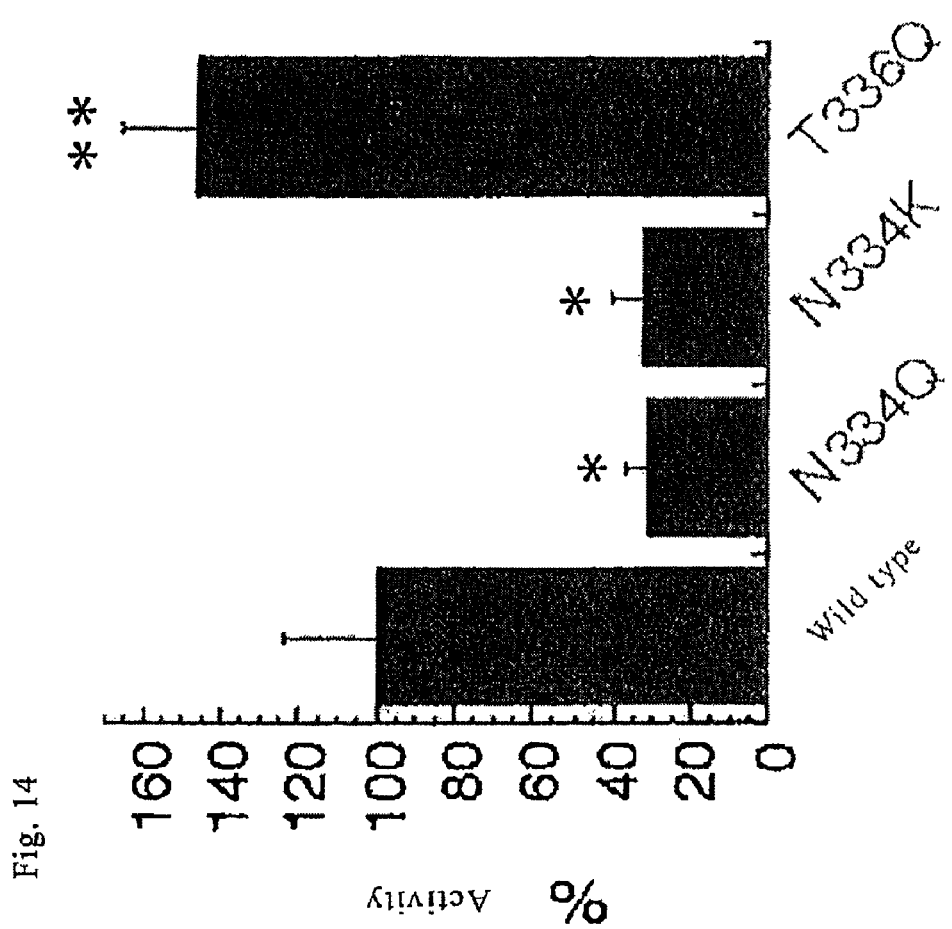
Figure 15:
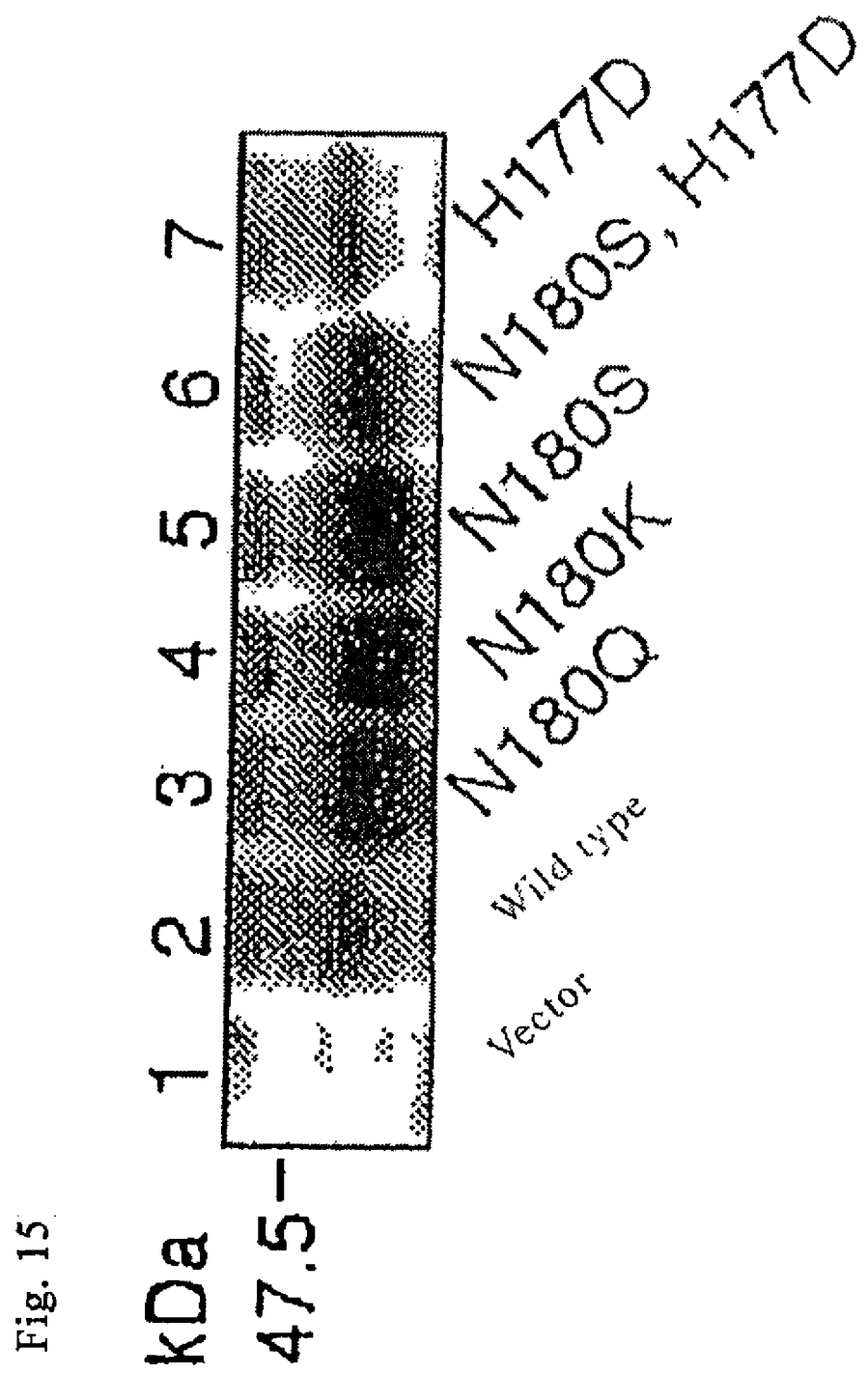
Figure 16:
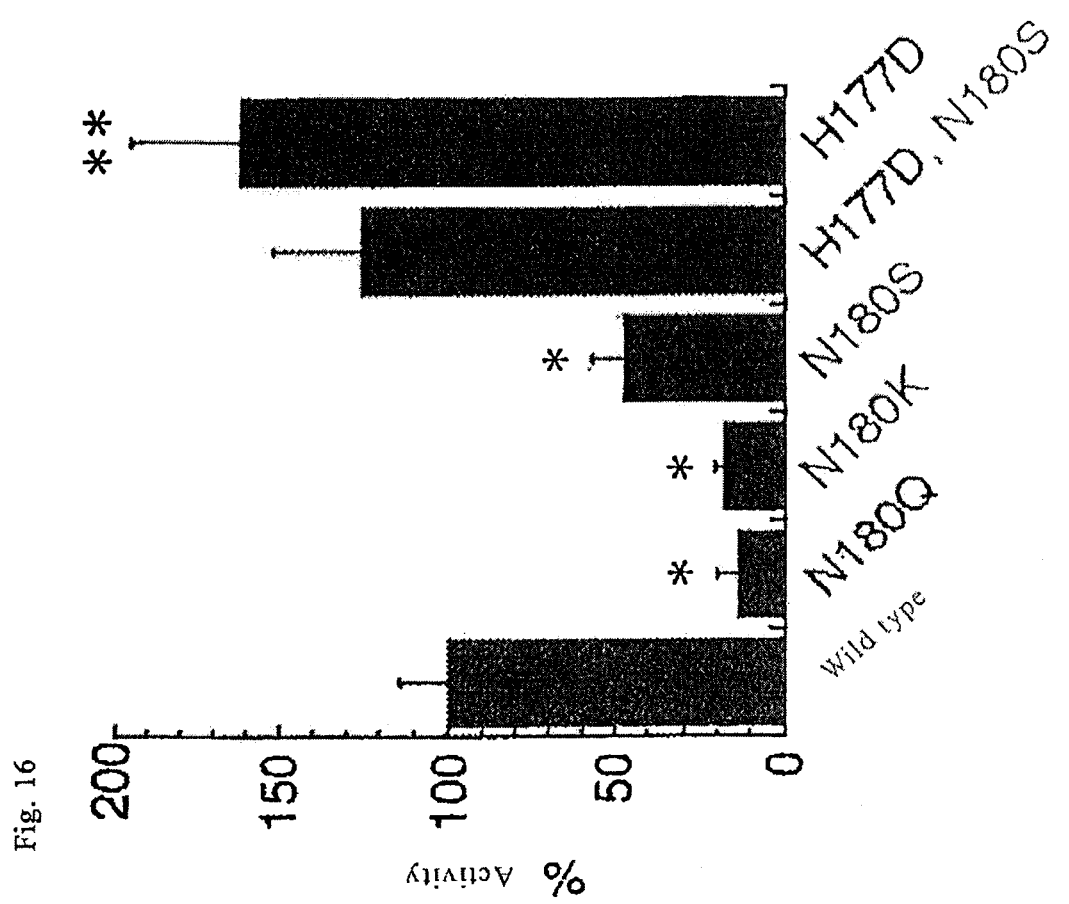

FIG. 10 is a diagram (photograph) showing the enzyme activity of the mSAT-I mutant. "*" indicates a significant difference with respect to the wild type at p<0.001.

FIG. 11 is a diagram (photograph) showing immunoblotting of cell lysates of expressing mSAT-I mutants.

FIG. 12 is a diagram showing the enzyme activity of the mSAT-1 mutants. "*" indicates a significant difference with respect to the wild type at p<0.001.

FIG. 13 is a diagram (photograph) showing immunoblotting of cell lysates expressing mSAT-1 mutants.

FIG. 14 is a diagram showing the enzyme activity of the mSAT-1 mutants. "*" indicates a significant difference with respect to the wild type at p<0.001 and "*" indicates a significant difference with respect to the wild type at p<0.05.

FIG. 15 is a diagram (photograph) showing immunoblotting of cell lysates of expressing mSAT-1 mutants.

FIG. 16 is a diagram showing the enzyme activity of the mSAT-1 mutants. "*" indicates a significant difference with respect to the wild type at p<0.001 and "*" indicates a significant difference with respect to the wild type at p<0.05.

FIG. 17 is a diagram (photograph) showing immunoblotting of cell lysates expressing mSAT-1 mutants.

FIG. 18 is a diagram showing the enzyme activity of the mSAT-1 mutant. "*" indicates a significant difference with respect to the wild type at p<0.001.

FIG. 19 is a diagram (photograph) showing immunoblotting of a lysate and culture medium of HEK293 cells which express mSAT-I. "1" to "4" indicate vectors used as controls, "5" to "8" show results of mSAT-I, "C" and "M" show results of a lysate of each cell and culture medium, respectively, PNGase F(−) indicates results without PNGase F treatment, and PNGase F(+) indicates results with PNGase F treatment.

FIG. 20 is a diagram showing the secretion amount of the mSAT-I mutant. Note that the secretion amount is indicated as a ratio of the amount of SAT-I protein secreted to a substrate to the amount of SAT-I protein present in the cell. "*" indicates a significant difference with respect to the wild type at p<0.001 and "**" indicates a significant difference with respect to the wild type at p<0.02.

FIG. 21 is a diagram (photograph) showing the enzyme activities of mSAT-I, "H177D, N180S, N224K, T336Q" mutants and the wild type mSAT-I which are expressed in *E. coli*. "-" in the first lane from the left indicates buffer only, and the first and second lanes from the right indicate 0.05 μg and 0.25 μg of GM3 standard, respectively.

DETAILED DESCRIPTION OF THE INVENTION

Hereinafter, detailed description will be made with reference to embodiments of the present invention.

<1> Protein of the Present Invention

The protein of the present invention is a mutant protein comprising an amino acid sequence of N-linked glycoprotein having the amino acid sequence motif (I) and/or (II) described below, wherein at least one amino acid selected from the amino acid sequence motif (I) and/or (II) described below is substituted by other amino acid, and wherein the amino acid sequence comprising the substituted amino acids retains an activity without undergoing any modification by N-linked sugar chain:

(I) Asn Xa1 Xa2 (SEQ ID NO: 1); and (II) Xa3 Val Gly Asn Xa1 Xa2 (SEQ ID NO: 2)

(in the amino acid sequence motif (I) and (II), Xa1 indicates an amino acid other than Pro, Xa2 indicates Thr or Ser, and Xa3 indicates His or Asp).

Herein, an N-linked glycoprotein into which the mutation is to be introduced is not particularly limited as far as it is a glycoprotein which contains an N-linked sugar chain. The N-linked sugar chains may be any one of high-mannose-type, complex-type, and hybrid-type and the number of the N-linked sugar chains is not limited. Further, the N-linked glycoprotein may contain an O-linked sugar chain.

Generally, in a polypeptide of a wild type N-linked glycoprotein, there is one or more amino acid sequences of the above-mentioned (I), (II) or both.

When the amino acid sequence motif (I) shown above is present at only one site in the glycoprotein into which the mutation is to be introduced, the protein of the present invention may be one in which at least one amino acid in the amino acid sequence motif is substituted. When the amino acid sequence motif (I) is present at two or more sites in the glycoprotein, the protein of the present invention may be one in which at least one amino acid is substituted in at least one of the amino acid sequences. Of course, the protein of the present invention may be one in which amino acids are substituted in all the amino acid sequence motifs that are present in the glycoprotein. The same applies to the amino acid sequence motif (II).

Further, when both the amino acid sequences (I) and (II) are present in the glycoprotein into which the mutation is introduced, the protein of the present invention may be one in which at least one amino acid is substituted in at least one of the amino acid sequences. Of course, the protein of the present invention may be one in which amino acids are substituted in both of them.

Therefore, when the amino acid sequence motif (I) is present at two sites and the amino acid sequence motif (II) is present at three sites in the glycoprotein, the protein of the present invention may be one in which one amino acid is substituted in at least one site among the five sites. In this case, the proteins of the present invention include, for example, one in which amino acids are substituted at two sites of the amino acid sequence motif (I) and at two sites of the amino acid sequence motif (II) among the five sites, and one in which amino acids are substituted at all the five sites.

In the proteins of the present invention obtained by amino acid substitution, Asn in the amino acid sequences (I) and (II) which contain the substituted amino acid does not undergo sugar chain modification. Since the N-linked sugar chain is linked to Asn in the consensus sequence comprising Asn-Xaa-Ser/Thr (Xaa is an amino acid other than Pro) in a protein, if the consensus sequence is destroyed by the above-mentioned substitution, the N-linked sugar chain is not retained in the above-mentioned amino acid sequences which contain the substituted amino acid. Although the mutant protein of the present invention may be one that has an N-linked sugar chain at site other than the substitution site, preferably it has no N-linked sugar chain as a whole.

A mutant protein in which at least one amino acid in the amino acid sequence (I) and/or (II) of the N-linked glycoprotein is substituted and which retains an activity can be obtained, for example: by comparing a glycosylation site or an amino acid sequence containing the glycosylation site with the amino acid sequence of a corresponding glycoprotein which is from another organism or which is from the same organism and belongs to the same protein family to clarify differences in the amino acid sequences at the glycosylation site between the protein in which a sugar chain is linked to the glycosylation site and the protein in which no sugar chain is linked to the glycosylation site; and by substituting the different amino acids in the protein in which a sugar chain is linked to the glycosylation site by the corresponding amino acids in the protein in which no sugar chain is linked to the glycosylation site.

In particular, the amino acid substitution in the amino acid sequence motif (I) and/or (II) is preferably one or more substitutions (A) to (C):
(A) substitution of Asn by Lys or Ser;
(B) substitution of Xa2 by Gln; and
(C) substitution of Xa3 by Asp.

For example, when the amino acid sequence motif (I) is present only at one site in a glycoprotein into which the mutation is introduced, the protein of the present invention may be any one of a protein in which Asn in the amino acid sequence is substituted by Lys or Ser, a protein in which Xa2 is substituted by Gln, or a protein in which both Asn and Xa2 are substituted. When the amino acid sequence motif (I) is present at 2 or more sites, the protein of the present invention may be one in which Asn in at least one of the amino acid sequences is substituted by Ser or Lys, or Xa2 in at least one of the amino acid sequences is substituted by Gln. Therefore, for example, when the amino acid sequence motif (I) is present at 6 sites in the glycoprotein into which the mutation is introduced, the protein of the present invention is one in which at least one of the substitutions selected from the substitution of Asn by Lys or Ser and the substitution of Xa2 by Gln occurs at least one site among the 6 sites.

When a plurality of the amino acid sequence motifs (I) are present in the glycoprotein into which the mutation is introduced, the kind and the number of amino acid substitutions of the protein of the present invention are not particularly limited.

That is, when the amino acid sequence motif (I) is present at 6 sites in the glycoprotein, the protein of the present invention may be one in which Asn is substituted by Ser in one of the amino acid sequences, Asn is substituted by Lys in another amino acid sequence, Xa2 is substituted by Gln in two other amino acid sequences, and the remaining two amino acid sequences are not substituted. Similar explanation is applicable to the amino acid motif (II).

In the present invention, the glycoprotein into which a mutation is introduced is preferably one which has some physiological activities. The protein of the present invention obtained by the above-mentioned amino acid substitution is characterized by retaining the physiological activity of the original glycoprotein even if it does not retain a part of or all the N-linked sugar chains to be linked. Whether the physiological activity of the glycoprotein is retained can be examined by comparing it with the physiological activity of the glycoprotein before the mutation is introduced by using a method of measuring the physiological activity that is selected as appropriate by one skilled in the art depending on the kind of the glycoprotein.

The phase "retains a physiological activity" does not necessarily mean that the mutant glycoprotein must have the same or higher activity than that of the N-linked glycoprotein before the mutation is introduced, as far as the mutant glycoprotein has the same kind of a physiological activity as the N-linked glycoprotein before the mutation is introduced. However, it is preferable that the mutant protein have preferably 30% or more activity, more preferably 50% or more activity than that of the N-linked glycoprotein before the mutation is introduced.

Further, examples of the glycoprotein having a physiological activity include enzymes, antibodies, cytokines, hormones, signal transducers, and receptors. These are exemplary and the present invention is not limited thereto. Among these, enzymes are preferable. Examples of the enzymes include glycosyltransferases, sulfotransferases, glycolytic enzymes, oxidoreductases, transferases, hydrolases, lyases, isomerases, and ligases. These are exemplary and the present invention is not limited thereto. Among these, glycosyltransferases are preferable. Examples of the glycosyltransferases include sialyltransferase, fucosyltransferase, N-acetylglucosaminyltransferase, N-acetylgalactosaminyltransferase, galactosyltransferase, and glucuronosyltransferase. These are exemplary and the present invention is not limited thereto. Among these, sialic acid transferase is preferable.

The sialic acid transferase is not particularly limited and examples thereof include SAT-I, α2,3-sialyltransferase, α2,6-sialyltransferase, and α2,8-sialyltransferase, and SAT-1 is preferable.

In addition, in the amino acid sequence of SAT-I, the amino acid sequence motif (I) above is preferably the amino acid sequence (i) and/or (ii) described below, and the amino acid sequence motif (II) above is preferably the amino acid sequence of (iii) described below.
(i) Asn Glu Ser (amino acid sequence represented by the amino acid Nos. 224 to 226 of SEQ ID NO: 4);
(ii) Asn Val Thr (amino acid sequence represented by the amino acid Nos. 334 to 336 of SEQ ID NO: 4); and
(iii) His Val Gly Asn Lys Thr (SEQ ID NO: 43 and amino acid sequence represented by the amino acid Nos. 177 to 182 of SEQ ID NO: 4).

Further, the amino acid substitution in the amino acid sequences (i) to (iii) is preferably one or more substitutions (a) to (d):
(a) substitution of Asn by Lys in the amino acid sequence (i);
(b) substitution of Thr by Gln in the amino acid sequence (ii);
(c) substitution of Asn by Ser in the amino acid sequence (iii); and
(d) substitution of His by Asp in the amino acid sequence (iii).

The kind of the amino acid substitution is not particularly limited as far as the mutant SAT-I retains the enzymatic activity, but is preferably substitutions of any one of the above-mentioned items (a), (b), (c), and (d), a combination of the above-mentioned items (a) and (b), a combination of the above-mentioned items (c) and (d), a combination of the above-mentioned items (a), (b) and (c), or a combination of all of the above-mentioned items (a) to (d).

The amino acid sequence of SAT-I before the mutation is introduced is not particularly limited as far as it serves as an enzyme that transfers sialic acid to lactosylceramide to synthesize GM3, that is a sialyltransferase that catalyzes a reaction wherein sialic acid is transferred to non-reducing terminal galactose through α-2,3-linkage. The amino acid sequence of mSAT-I (SEQ ID NO: 4) is preferably used. Also, SAT-I that has an amino acid sequence having homology of 80% or more, preferably 90% or more, and more preferably 95% or more with the amino acid sequence of mSAT-I may be used.

It is also preferable to use the amino acid sequence of hSAT-I (SEQ ID NO: 42) as the amino acid sequence of SAT-I before the mutation is introduced. Also, SAT-I that has an amino acid sequence having homology of 80% or more, preferably 90% or more, and more preferably 95% or more with the amino acid sequence of hSAT-I may be used.

Further, the mutant SAT-1 is particularly preferably the protein having the following amino acid sequences.
the amino acid sequence of SEQ ID NO: 6.
the amino acid sequence of SEQ ID NO: 8.
the amino acid sequence of SEQ ID NO: 10.
the amino acid sequence of SEQ ID NO: 12.
the amino acid sequence of SEQ ID NO: 14.
the amino acid sequence of SEQ ID NO: 16.
the amino acid sequence of SEQ ID NO: 18.

In addition, other proteins (including peptide or peptides) may be linked to the protein of the present invention as far as the proteins give no substantial influence to the physiological activity of the protein of the present invention. That is, the term "protein of the present invention" includes a fusion protein composed of the protein of the present invention to which one or more other proteins (including peptide or peptides) is/are linked. The term "other proteins" as used herein includes peptides, and the kind of the other protein is not particularly limited and may be selected as appropriate depending on the purpose. Production of a fusion protein is intended to, for example, allow the protein to be secreted outside the cells, facilitate separation and purification, facilitate detection, or combine activities of a plurality of proteins. However, the object is not limited thereto. Reference is made to the explanation regarding the section "Polynucleotide of the Present Invention" described hereinbelow about examples of the term "other proteins".

The protein of the present invention can be either chemically synthesized or produced by genetic engineering since it has been clarified by the present invention which part of it should be substituted and how it should be made. Regarding the method of producing the protein of the present invention by genetic engineering, reference is made to the section "Polynucleotide of the Present Invention" and Examples described hereinbelow.

Whether the protein of the present invention is obtained, synthesized, produced or the like can be readily judged by analyzing the amino acid sequence (or nucleotide sequence of the polynucleotide encoding the same) of a resultant protein and comparing the amino acid sequence with the sequence of the protein of the present invention (or the polynucleotide of the present invention).

Further, in the protein of the present invention, whether an N-linked sugar chain is linked to the amino acid sequence that contains the substituted amino acids can be conveniently examined by observing whether a sugar chain is released and whether the molecular weight of the protein is changed by allowing a suitable glycosidase (for example, PNGase F) to react with the protein.

<2> Polynucleotide of the Present Invention

The polynucleotide of the present invention is a polynucleotide that encodes the protein of the present invention.

The polynucleotide that encodes the protein of the present invention includes various polynucleotides having different nucleotide sequences due to degeneration of a genetic code. One skilled in the art can easily understand that any of such polynucleotides is included in the polynucleotide of the present invention.

For example, to obtain the mutant mSAT-I having amino acid sequences set forth below by introducing a mutation into mSAT-I having the amino acid sequence of SEQ ID NO: 4, the polynucleotides having the following nucleotide sequences may be used. However, it can be readily understood that these polynucleotides are exemplary and the present invention is not limited thereto.

(Protein)
the amino acid sequence of SEQ ID NO: 6.
the amino acid sequence of SEQ ID NO: 8.
the amino acid sequence of SEQ ID NO: 10.
the amino acid sequence of SEQ ID NO: 12.
the amino acid sequence of SEQ ID NO: 14.
the amino acid sequence of SEQ ID NO: 16.
the amino acid sequence of SEQ ID NO: 18.

(Polynucleotide)
the nucleotide sequence of SEQ ID NO: 5.
the nucleotide sequence of SEQ ID NO: 7.
the nucleotide sequence of SEQ ID NO: 9.
the nucleotide sequence of SEQ ID NO: 11.
the nucleotide sequence of SEQ ID NO: 13.
the nucleotide sequence of SEQ ID NO: 15.
the nucleotide sequence of SEQ ID NO: 17.

Although the nucleotides that constitute the polynucleotide of the present invention may be either a DNA or an RNA, it is preferably a DNA in terms of stability.

The polynucleotides of the present invention includes not only polynucleotides which directly encode the protein of the present invention but also polynucleotides having a sequence complementary to them.

The polynucleotide of the present invention can be produced, for example, by the following method.

First, the amino acid sequence of N-linked glycoprotein of interest is analyzed. Also, the nucleotide sequence of a polynucleotide that encodes the N-linked glycoprotein is determined as necessary. Then, nucleotides of a corresponding portion of the polynucleotide that encodes the glycoprotein is substituted by other nucleotides so that at least one amino acid of one or more of the amino acid sequence motif (I) and/or (II) present in the amino acid sequence is substituted by other amino acid(s):

(I) Asn Xa1 Xa2 (SEQ ID NO: 1); and
(II) Xa3 Val Gly Asn Xa1 Xa2 (SEQ ID NO: 2)
(in (I) and (II), Xa1 indicates an amino acid other than Pro, Xa2 indicates Thr or Ser, and Xa3 indicates His or Asp).

The number and kind of the nucleotide to be substituted are not particularly limited as far as the amino acid to be substituted can be substituted by other amino acid as a target. For example, there may be a case where substitution of only one nucleotide is sufficient or where three nucleotides must be substituted to effect the substitution by the target amino acid. How to introduce substitution of nucleotides can be determined as appropriate by one skilled in the art.

Since it has now been clarified what a portion and how a substitution should be performed, the substitution of nucleotides (i.e., production of the polynucleotide of the present invention) can be performed by using either a technique of chemical synthesis or a technique of genetic engineering.

In the case where the technique of chemical synthesis is used, chemical synthesis may be performed by designing a nucleotide sequence such that the substitution of interest can be introduced and then by performing chemical synthesis so that a nucleotide sequence as designed can be obtained.

In the case where the technique of genetic engineering is used, various methods can be adapted. For example, there can be used a method in which a primer corresponding to a portion of the polynucleotide encoding a target N-linked glycoprotein into which a nucleotide substitution is intended to be introduced (i.e., a primer having a nucleotide substituted by the target nucleotide) is synthesized, and a nucleotide is substituted using a polynucleotide encoding the target glycoprotein as a template and a commercially available mutation introducing kit (for example, QuickChange site-directed mutagenesis kit manufactured by Stratagene). For specific examples thereof, reference is made to the Examples below.

The obtained polynucleotide of the present invention may be further amplified or purified. Also, it may be incorporated into suitable plasmids, vectors, and so on.

The polynucleotide of the present invention thus obtained can be used in the production of the proteins of the present invention.

For example, PCR is performed by using the polynucleotide (i.e., DNA) of the present invention as a template to amplify the polynucleotide of the present invention. Then, the amplified polynucleotide of the present invention is incorporated into a suitable expression vector or the like.

The vector to be used herein is not particularly limited and can be selected as appropriate by one skilled in the art depending on the kind of cells (i.e., host) into which a gene is introduced and so on. For example, when eukaryotic cells are used as host cells, an expression vector for eukaryotic cells can be selected, while when prokaryotic cells are used as host cells, an expression vector for prokaryotic cells can be selected.

In particular, the expression vector for eukaryotic cells are preferably used, and an expression vector for mammalian cells are more preferably used.

Further, the expression vector may be constructed so that the protein of the present invention encoded by the polynucleotide of the present invention can be isolated and purified easily. In particular, when the expression vector is constructed so that the protein of the present invention is expressed in a form of a "fusion protein" comprising the protein of the present invention linked to other protein (for example, a labeled peptide), the protein of the present invention can be isolated and purified easily.

Examples of such "other protein" include various peptides such as signal peptides (i.e. peptides consisting of 15 to 30 amino acid residues which present at N-terminals of many proteins and function inside cells for the selection of proteins in the intracellular membrane penetration mechanism: for example, OmpA, OmpT, Dsb and so on), protein kinase A, protein A (a protein having a molecular weight of about 42,000, which is a constituent of a cell wall of *Staphylococcus aureus*), glutathione S-transferase, His tag (a sequence of 6 to 10 histidine residues arranged in a row), myc tag (a sequence of 13 amino acids from cMyc protein), FLAG peptide (a marker for analysis consisting of 8 amino acid residues), T7 tag (consisting of first 11 amino acid residues of gene 10 protein), S tag (consisting of 15 amino acid residues from pancreatic RNase A), HSV tag, pelB (a sequence consisting of 22 amino acids of *Escherichia coli* outer membrane protein pelB), HA tag (consisting of 10 amino acid residues from haemagglutinin), Trx tag (thioredoxin sequence), CBP tag (calmodulin binding peptide), CBD tag (cellulose binding domain), CBR tag (collagen binding domain), β-lac/blu (β-lactamase), β-gal (β-galactosidase), luc (luciferase), HP-Thio (His-patch thioredoxin), HSP (heat shock peptide), Lny (laminin-γ-peptide), Fn (fibronectin partial peptide), GFP (Green fluorescent peptide), YFP (yellow fluorescent peptide), CFP (cyan fluorescent peptide), BFP (blue fluorescent peptide), DsRed and DsRed2 (red fluorescent peptides), MBP (maltose binding peptide), LacZ (lactose operator), IgG (immunoglobulin G), avidin, and protein G.

Expression vectors into which the protein of the present invention has been incorporated are extracted and purified and then introduced into host cells. Host cells can be selected as appropriate depending on the kind of the expression vector to be used and are not particularly limited. Host cells may be either eukaryotic cells (e.g., mammalian cells, yeast, insect cells, and so on) or prokaryotic cells (e.g., *Escherichia coli*, *Bacillus subtilis*, and so on).

For example, when an expression vector for mammalian cells is used, mammalian cells can be used as host cells. The kind of the mammalian cells referred to herein is not particularly limited and can be selected as appropriate in terms of the object, expression efficiency, or the like. For example, chinese hamster ovary derived cell line (i.e., CHO cell line) and so on may be used.

The expression vector into which the polynucleotide (DNA) of the present invention has been incorporated is introduced into such cells and cultivated by conventional methods. The conditions of culture may be selected as appropriate depending on the kind of vector/host cells, objects, and so on.

In this manner, by culturing the cells into which the polynucleotide of the present invention has been introduced and collecting the culture product, the protein of the present invention is produced. As appropriate, the protein of the present invention may be further purified by using known extraction and purification methods.

<3> Method of the Present Invention

The method of the present invention is characterized by:
comparing, in an amino acid sequence of an N-linked glycoprotein having the amino acid sequence motif (I) and/or (II) shown below, the amino acid sequence motif (I) and/or (II) described below or an amino acid sequence comprising the amino acid sequence motif (I) and/or (II) with a corresponding protein from another organism, or with a corresponding amino acid sequence of another protein which is from the same organism as the glycoprotein and which belongs to the same protein family as the glycoprotein to clarify differences between the amino acid sequences; and
substituting the different amino acids by corresponding amino acids of the target of comparison:
(I) Asn Xa1 Xa2 (SEQ ID NO: 1); and
(II) Xa3 Val Gly Asn Xa1 Xa2 (SEQ ID NO: 2)

(Xa1 indicates an amino acid other than Pro, Xa2 indicates Thr or Ser, and Xa3 indicates His or Asp in the amino acid sequence motif (I) and (II)).

Further, in the case of comparing amino acid sequences according to the method of the present invention, only the glycosylation sites represented by the amino acid sequences (I) and (II) may be compared, but usually it is preferable that amino acid sequences including those sequences are compared in a wider range. Accordingly, it becomes possible to define the amino acid sequence corresponding to the glycosylation site.

The term "corresponding protein from another organism" is not particularly limited as far as it is a protein that has a similar physiological activity in an organism which belongs to a different genus. However, it is preferable that the protein from said organism has no N-linked sugar chain in a part of or the whole glycosylation site thereof and retains the physiological activity of the N-linked glycoprotein before the mutation is introduced. In the method of producing the mutant protein of the present invention from a wild type glycoprotein from a mammal, for example, an amino acid sequence of a wild type glycoprotein from a mammalian is compared preferably with an amino acid sequence of a corresponding wild type glycoprotein from fishes such as medaka or tetradon.

Further, another protein which is from the same organism as the glycoprotein that is the target of amino acid substitution and which belongs to the same protein family is not particularly limited as far as the protein is from the same organism as the glycoprotein that is the target of amino acid substitution and the protein has a physiological activity or structure similar to that of the glycoprotein. However, it is preferable that the another protein has no N-linked sugar chain in a part of or the whole glycosylation site thereof and has a physiological activity similar to that of the N-linked glycoprotein before the mutation is introduced.

The meanings of all the other terms described in connection with the method of the present invention are the same as those used in connection with the protein of the present invention.

Thus, the amino acid substitution in the amino acid sequence motif (I) and/or (II) is preferably one or more substitutions (A) to (C):
(A) Substitution of Asn by Lys or Ser;
(B) Substitution of Xa2 by Gln; and
(C) Substitution of Xa3 by Asp.

Further, the method of the present invention can preferably be applied to enzymes and more preferably glycosyltransferases. In particular, the method of the present invention is preferably applicable to sialyltransferase, and more preferably SAT-I.

Further, in the amino acid sequence of SAT-I before the mutation is introduced, the amino acid sequence motif (I) is preferably the amino acid sequence (i) and/or (ii), and the amino acid sequence motif (II) is preferably the amino acid sequence (iii):

(i) Asn Glu Ser (an amino acid sequence represented by the amino acid Nos. 224 to 226 of SEQ ID NO: 4);

(ii) Asn Val Thr (an amino acid sequence represented by the amino acid Nos. 334 to 336 of SEQ ID NO: 4); and (iii) His Val Gly Asn Lys Thr (SEQ ID NO: 43 and an amino acid sequence represented by the amino acid Nos. 177 to 182 of SEQ ID NO: 4).

Further, at least one amino acid substitution of the amino acid sequences (i) to (iii) described below is preferably one or more substitutions (a) to (d):

(a) Substitution of Asn by Lys in the amino acid sequence (i);

(b) Substitution of Thr by Gln in the amino acid sequence (ii);

(c) Substitution of Asn by Ser in the amino acid sequence (iii); and (d) Substitution of His by Asp in the amino acid sequence (iii).

The substitution of an amino acid in the method of the present invention can be performed according to the method described in the explanation of "the protein of the present invention" and "the polynucleotide of the present invention".

In the method of the present invention, whether the protein retains an N-linked sugar chain or whether it retains the physiological activity of the glycoprotein can be confirmed by the method described in the explanation of "the protein of the present invention".

EXAMPLES

Hereinafter, the present invention is described in more detail by referring to examples in which SAT-I (a kind of N-linked glycoprotein) is used.

<1> Materials, Methods, and so on

The materials, methods, and so on used in the present invention are as follows.

LIPOFECTAMINE™ 2000 Reagent: manufactured by Life Technology, Inc.

NUTRIENT MIXTURE F-12 HAM (HAM): manufactured by SIGMA.

PVDF membrane (i.e., Immobilon): manufactured by MILLIPORE.

X-ray film (i.e., Medical X-ray film): manufactured by Kodak.

Endo H: manufactured by New England Biolabs.

PNGase F: manufactured by New England Biolabs.

Tunicamycin: manufactured by SIGMA.

Kifnecin: manufactured by CALBIOCHEM.

Castanospermine: manufactured by CALBIOCHEM.

CMP-sialic acid: manufactured by SIGMA.

LacCer: manufactured by Matreya, Inc.

SepPak Plus 18: manufactured by Waters Associates (Milford, Mass.)).

Silica gel HPTLC: manufactured by Merck.

Anti-SAT-I antibody: anti-SAT-I rabbit IgG antibody (i.e., a polyclonal antibody prepared by using 51 residues at C-terminal side of mSAT-I as an antigen).

5×SDS sample buffer: 62.5 mM Tris (pH 6.8), 2% SDS, 10% glycerol, 0.001% BPB, and 5% 2-mercaptoethanol.

Running buffer: 25 mM Tris (pH 8.9), 192 mM glycine, 0.1% SDS.

Transfer buffer: 25 mM Tris, 192 mM glycine, 20% methanol.

TBS-T buffer: 137 mM NaCl, 20 mM Tris (pH 7.5), 0.05% Tween 20.

Blocking buffer: 5% skim milk solution prepared by using TBS-T buffer.

Cell suspension solution: 5% glycerol, 15 mM sodium cacodylate, 0.1% Lubrol (manufactured by ICN Biochemicals Inc.), protease inhibitor mixture (Complete™ EDTA free): manufactured by Roche Applied Science.

4× Reaction mixture: 400 mM sodium cacodylate, 40 mM $MgCl_2$, 1.6% Triton X-100.

PBS: 137 mM NaCl, 2.68 mM KCl, 10 mM $Na_2HPO_4$, 1.76 mM $KH_2PO_4$.

IP buffer: 50 mM Tris (pH 7.4), 150 mM NaCl, 2 mM NaF, 1 mM EDTA, 1 mM EGTA, 1% Triton X-100, 1 mM PMSF, protease inhibitor mixture (Complete™ EDTA free): manufactured by Roche Applied Science.

Cell culture: CHO cells were cultured by using NUTRIENT MIXTURE F-12 HAM medium containing 10% (v/v) FBS, 100 units/ml penicillin, 100 ng/ml streptomycin, 9.4% (v/v) sodium hydrogen carbonate, and 100 mM L-glutamine under conditions of 37° C. and 5% $CO_2$. The cells were recovered by using 0.25% trypsin/1 mM EDTA solution by subculturing once for every 3 days.

Introduction of SAT-I gene into CHO cells

CHO cells were inoculated on a 6-well plate and cultivated until 90% to 95% confluent was achieved. Then, the cells were gently washed with a medium that contained neither antibiotics nor serum (i.e., HAM (−/−)), followed by addition of 2.25 ml of the same medium and 250 μl of FBS.

Then, a plasmid (2 μg; pcDNA3.1 Zeo(+) (Invitrogen) into which the mSAT-I gene was incorporated) and 10 μl of LIPOFECTAMINE™ 200 Reagent were mixed with 250 μl of HAM (−/−), respectively, and the resultants were left to stand at room temperature for 5 minutes. After that, the both were mixed with each other and the resultant was left to stand at room temperature for 20 minutes. Then the resultant was added to the cells, followed by culturing for 24 hours. In the case where an inhibitor such as tunicamycin was added, the medium was replaced 6 hours after the transfection and inhibitors were added thereto (final concentration: tunicamycin: 2.5 Kifnecin: 5 μg/ml, castanospermine: 1 mM) and the mixture was cultured for 18 hours.

SDS-PAGE

5% polyacrylamide gel as a concentration gel and 7.5% or 10% polyacrylamide gel as a separation gel were used. 5×SDS sample buffer was added in a volume ⅓ of that of the sample solution and the mixture was boiled at 37° C. for about 3 minutes to denature the sample to prepare a sample for electrophoresis. By using a mini-real slab gel electrophoresis apparatus (manufactured by Biocraft, Inc.), electrophoresis was performed at a constant current of 20 mA for about 80 minutes. As a molecular weight marker serving as an index for molecular weight, Prestained Protein Marker was used. The molecular weights of the proteins included in the molecular weight marker were 175, 83, 62, 47.5, 32.5, 25, 16.5, and 6.5 kDa.

Immunoblotting

After SDS-PAGE was completed, the gel and the activated PVDF membrane were each equilibrated with transfer buffer by shaking for about 5 minutes. By using a semi-dry type transfer apparatus (trade name: Trans-Blot SD, manufactured by Biorad, Inc.), the protein in the gel was transferred onto the PVDF membrane at 10 V for 30 minutes. The PVDF membrane was blocked by using a blocking buffer at room temperature for 1 hour. After that, a primary antibody (i.e., anti-SAT-I antibody) was diluted 1,000 fold with the blocking buffer. The PVDF membrane was dipped in the resultant solution and shaken at overnight 4° C. After that, the PVDF membrane was dipped in a secondary antibody solution (i.e., anti-rabbit IgG labeled with HRP) diluted about 5,000 folds with TBS-T buffer, and allowed to react at room temperature for 1 hour.

The PVDF membrane after the reaction was colored with a Western blotting detecting reagent (i.e., ECL or ECL Plus (manufactured by Amersham Biosciences) or Lumi-Light Plus (manufactured by Roche Diagnostics Co., Ltd.). For detection, an X-ray film was used.

Sugar Chain Cleaving Reaction

Endo H or PNGase F was added to samples prepared by the alkali-acetone method and the samples were allowed to react at 37° C. for 1 hour. Then, the samples were analyzed by immunoblotting.

Assay of SAT-I Activity

CHO cells into which the mSAT-I gene was introduced (placed on a 6-well plate) were washed with ice-cold PBS and then 80 μl of solution for cell suspension was added to the cells and the cells were collected. After the cells were sonicated (once for 10 seconds), the sonicated product was centrifuged at 4° C. and 15,000×g for 10 minutes to collect the supernatant, which was used as an enzyme source. Further, 10.68 μl of 1 mg/ml LacCer was dried at room temperature, to which 10 μl of 4× Reaction mixture was added. The resultant was sonicated to suspend LacCer. To the suspension were added 20 μl of the enzyme source and a 1:4 mixture of radiolabeled CMP-sialic acid (i.e., Cytidine 5'-monophosphate, [4,5,6,7,8,9-$^{14}$C]sialic acid (manufactured by NEN Life Science Products)) and non-radiolabeled CMP-sialic acid were added and the resultant mixture was allowed to react at 37° C. for 2 hours.

A fraction that contained lipids was purified from the solution after the reaction by using Sep-Pak Plus 18 and the resultant was applied to an HPTLC plate. Lipids were separated with a developing solvent (chloroform/methanol/0.2% $CaCl_2$ (55/45/10)).

Creation of SAT-I Mutant

Various mutants of mSAT-I were created by using mSAT-I as a template and QuickChange site-directed mutagenesis kit (manufactured by Stratagene) according to the recommendations described in the manual attached to the kit. The primers used for creating the various mutants are shown below.

N180Q:
(SEQ ID NO: 19)
5'-CTCTGAACACGTTGGGCAGAAAACTACTATAAGG-3'
(SEQ ID NO: 20)
5'-CCTTATAGTAGTTTTCTGCCCAACGTGTTCAGAG-3'

N180K:
(SEQ ID NO: 21)
5'-CTCTGAACACGTTGGGAAGAAAACTACTATAAGG-3'
(SEQ ID NO: 22)
5'-CCTTATAGTAGTTTTCTTCCCAACGTGTTCAGAG-3'

N180S:
(SEQ ID NO: 23)
5'-CTCTGAACACGTTGGGAGCAAAACTACTATAAGG-3'
(SEQ ID NO: 24)
5'-CCTTATAGTAGTTTTGCTCCCAACGTGTTCAGAG-3'

H177D, N180S:
(SEQ ID NO: 25)
5'-GAGGGTTACTCTGAAGAGGTTGGGCAGAAAACTACTATAAGG-3'
(SEQ ID NO: 26)
5'-CCTTATAGTAGTTTTGCTCCCAACGTCTTCAGAGTAACCCTC-3'

H177D:
(SEQ ID NO: 27)
5'-GAGGGTTACTCTGAAGAGGTTGGGCAGAAAACTAC-3'
(SEQ ID NO: 28)
5'-GTAGTTTTATTCCCAACGTCTTCAGAGTAACCCTC-3'

N224Q:
(SEQ ID NO: 29)
5'-GCAATGGTAAAACAGGAAAGCCTGCCC-3'
(SEQ ID NO: 30)
5'-GGGCAGGCTTTCCTGTTTTACCATTGC-3'

N224K:
(SEQ ID NO: 31)
5'-GCAATGGTAAAAAAGGAAAGCCTGCCC-3'
(SEQ ID NO: 32)
5'-GGGCAGGCTTTCCTTTTTTACCATTGC-3'

N224D:
(SEQ ID NO: 33)
5'-GCTTCAAGCAATGGTAAAACAGGAAAGCCTGCCCTTTTG-3'
(SEQ ID NO: 34)
5'-CAAAAGGGCAGGCTTTCATCTTTTACCATTGCTTGAAGC-3'

N334Q:
(SEQ ID NO: 35)
5'-CTGGCAGGTCATGCACCAGGTGACCACAGAGACCAAG-3'
(SEQ ID NO: 36)
5'-CTTGGTCTCTGTGGTCACCTGGTGCATGACCTGCCAG-3'

N334K:
(SEQ ID NO: 37)
5'-CTGGCAGGTCATGCACAAGGTGACCACAGAGACCAAG-3'
(SEQ ID NO: 38)
5'-CTTGGTCTCTGTGGTCACCTTGTGCATGACCTGCCAG-3'

T336Q:
(SEQ ID NO: 39)
5'-CAGGTCATGCACAAGGTGACCACAGAGACCAAGTTCCTC-3'
(SEQ ID NO: 40)
5'-GAGGAACTTGGTCTCTGTCTGCACATTGTGCATGACCTG-3'

Trypsin Sensitivity Test

After washing of CHO cells into which the mSAT-I gene was transfected (placed on a 6-well plate) with ice-cold PBS, 100 μl of IP buffer was added thereto and the cells were collected. The cells were sonicated (once for 10 seconds), and centrifuged at 4° C. and 15,000×g for 10 minutes. The supernatant was collected, to which trypsin was added such that the final concentration was 0, 10, 20, 50, or 100 ng/μl and the resultants were allowed to react at 37° C. for 30 minutes. After that, 10% SDS was added to a final concentration of 1% to stop the reaction.

<2> Results
(1) Interspecies Comparison of N-Glycosylation Sites

Cloned SAT-Is of human, mouse, rat, and zebra-fish each have a transmembrane region in the N-terminal side and have sequences that are conserved in sialic acid transferase, called "sialyl motif L", "sialyl motif S", and "sialyl motif VS". The sialyl motif L is known to participate in binding to CMP-sialic acid, while functions of the other motifs have not been defined yet. The results of amino acid sequence comparison between hSAT-I (SEQ ID NO: 42), mSAT-I (SEQ ID NO: 4) and zSAT-I (SEQ ID NO: 41) are shown in Table 1.

Further, N-linked sugar chains are known to link to the Asn residue of the amino acid sequence referred to as "Asn-Xaa-Thr/Ser" present in a glycoprotein.

In FIG. 1, the dotted crossbar line portion indicates a transmembrane region, the first solid crossbar line portion indicates a sialyl motif L, the second solid crossbar line portion indicates a sialyl motif S, and the third solid crossbar line portion indicates a sialyl motif VS. Further, the portion boxed with a bold line indicates a portion to which an N-linked sugar chain can be linked (N-glycosylation site). It has been shown that N-linked sugar chains can be linked to N180, N224, and N334 of mSAT-I.

Comparison of the amino acid sequences at the N-glycolation site indicates that except for the site in the sialyl motif L, the amino acid sequences at the N-glycosylation site are not conserved in the species. This suggests two possibilities that the sugar chains other than the sialyl motif L are not important to SAT-I, or that the modified amino acid sequence alternates the function of the sugar chain.

The comparison of the amino acid sequence of mSAT-I with the amino acid sequences of cloned SAT-Is from bovine, dog, rat, chicken, medaka, and a tetradon was performed according to the procedures of Clustal W (Thompson, J. D., Higgins, D. G, and Gibson, T. J. (1994) Nucleic Acids Res. 22, 4673-4680), and BOXSHADE (Institute for Animal Health, Surrey, UK), and indicated that regarding the amino acid sequence portions of the bovine, dog, rat, and chicken corresponding to the amino acid sequences of the N-glycosylation sites (around N180, N224, and N334) of mSAT-I, percentages of amino acid conservation were high. On the other hand, in medaka and tetradon, percentages of amino acid conservation were relatively low and the amino acids corresponding to N180, N224, and N334 were different, that is, they were S, K, and D, respectively.

Similarly, comparison of the amino acid sequence of the human-derived sialyltransferase with those of various enzyme families indicated that differences were observed among the enzyme families, that, for example, N at the 180th position in the glycosylation site present in the sialyl motif L in SAT-I was S or T, and H at the 177th position was D.

Further, the glycosylation site and its number in various sialyltransferases are known to differ from each other among species or enzyme families; this fact is considered to reflect a change in functional regulation of glycosyltransferases in the process of evolution to higher organisms. That is, the difference suggests the possibility that substitution of a particular amino acid allows to create an enzyme that retains its activity without sugar chains.

(2) Study on the Presence or Absence of Sugar Chains Linked to Sat-I and Kinds Thereof.

An anti-SAT-I antibody (polyclonal antibody) was prepared by using 51 residues at C-terminal of mSAT-I as an antigen. mSAT-I was transiently expressed by using CHO cells, and a lysate of the cells was subjected to SDS-PAGE and then to immunoblotting with an anti-SAT-I antibody. A lysate of the cells treated with Endo H or PNGase F was also subjected to immunoblotting with an anti-SAT-I antibody. The results are shown in FIG. 2.

The molecular weight of mSAT-I estimated by the amino acid sequence of mSAT-I is about 40 kDa. However, a major band having a larger molecular weight than that of mSAT-I was detected near 42 kDa and a broad band was detected from 45 kDa to 48 kDa (Lane 2 in FIG. 2). The result suggested that some modification was made to mSAT-I.

Figure 2:
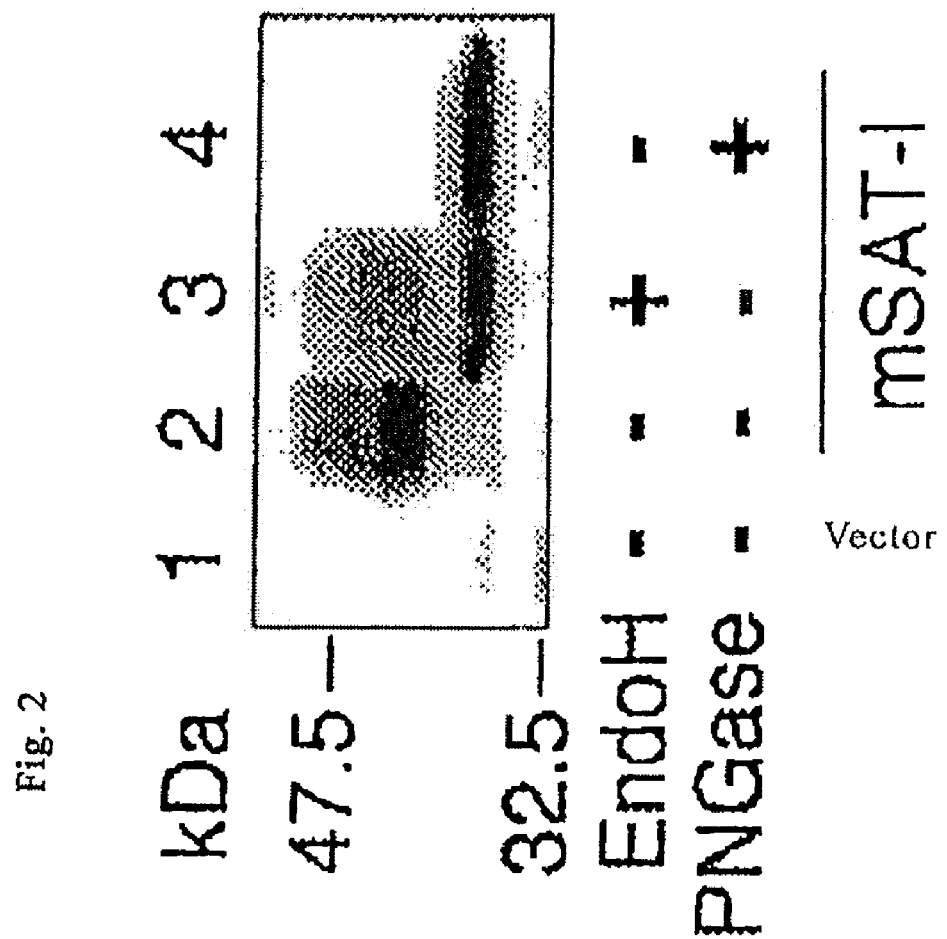

Further, treatment with PNGase F resulted in all the mSAT-I bands aggregated to a molecular weight of 40 kDa (Lane 4 in FIG. 2), while treatment with Endo H did not lead to complete cleavage of sugar chains, so that an Endo H-resistant band was detected (Lane 3 in FIG. 2). These results indicate that a complex sugar chain modified by the Golgi apparatus is linked to mSAT-I.

(3) Influence of Sugar Chain on Sat-I Activity

When mSAT-I was transiently expressed by using CHO cells, the cells were treated with an inhibitor (tunicamycin, Kifnecin, or castanospermine) of sugar chain processing in ER. Treatment with tunicamycin inhibited dolicholpyrophosphate-N-acetylglucosamine formation to suppress the glycosyltransfer to the protein. Treatment with Kifnecin inhibited mannosidase, resulting in generation of mSAT-I having a high mannose type sugar chain immediately before the transportation to the Golgi apparatus, preventing the formation of mSAT-I having a complex type sugar chain. Treatment with castanospermine causes inhibition of glucosidases I and II to suppress the interaction with calnexin or calreticulin that interacts by recognizing monoglucosylated sugar chains.

Figure 3:
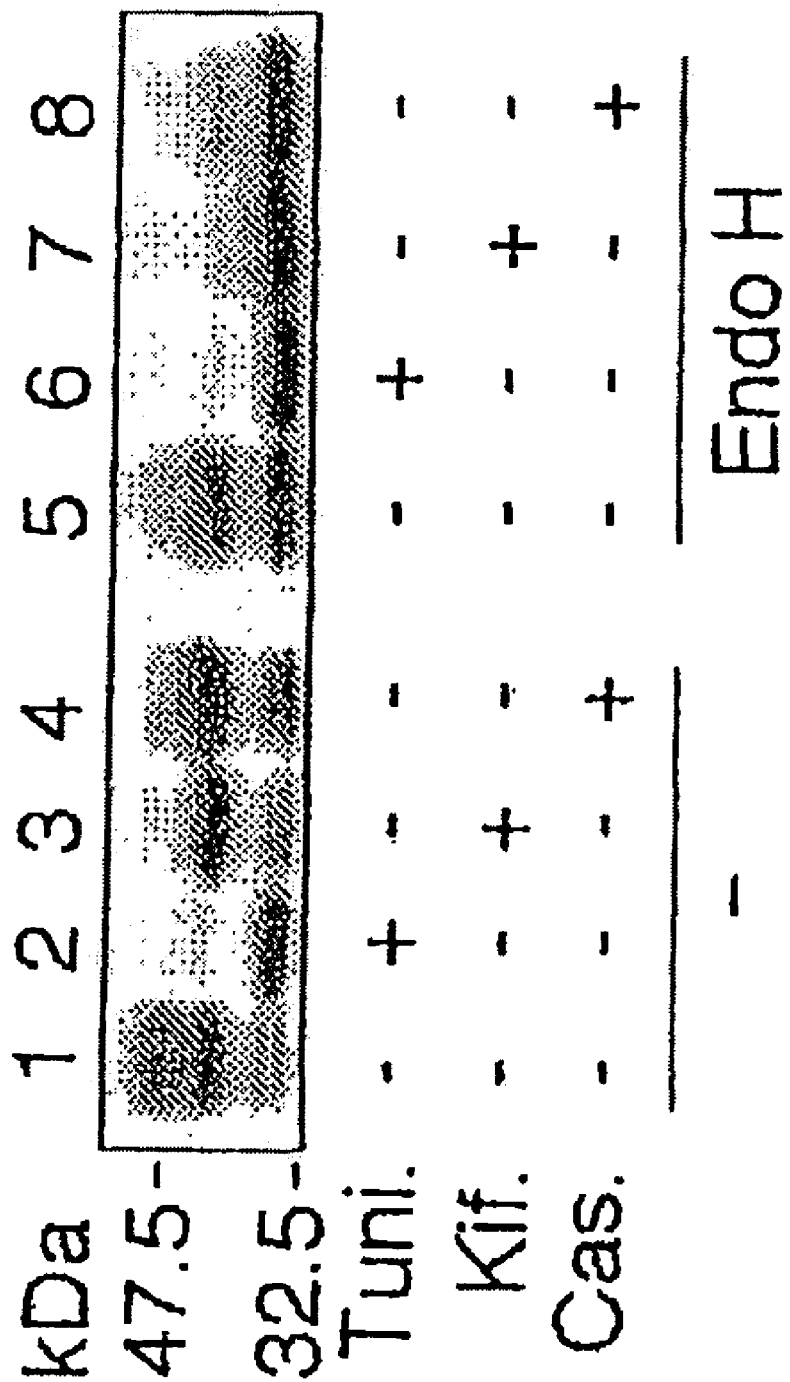

Lysates of the cells treated with those inhibitors were prepared in the presence or absence of Endo H and the lysates were subjected to SDS-PAGE, followed by immunoblotting with an anti-SAT-I antibody. Results are shown in FIG. 3. Results of assay of SAT-I activity by using the lysates are shown in FIG. 4.

FIG. 3 indicates that treatment with tunicamycin completely suppressed the glycosyltransfer to SAT-I and that treatment with Kifnecin or castanospermine resulted in linking of only high mannose type sugar chain (cleaved by Endo H).

Figure 4:
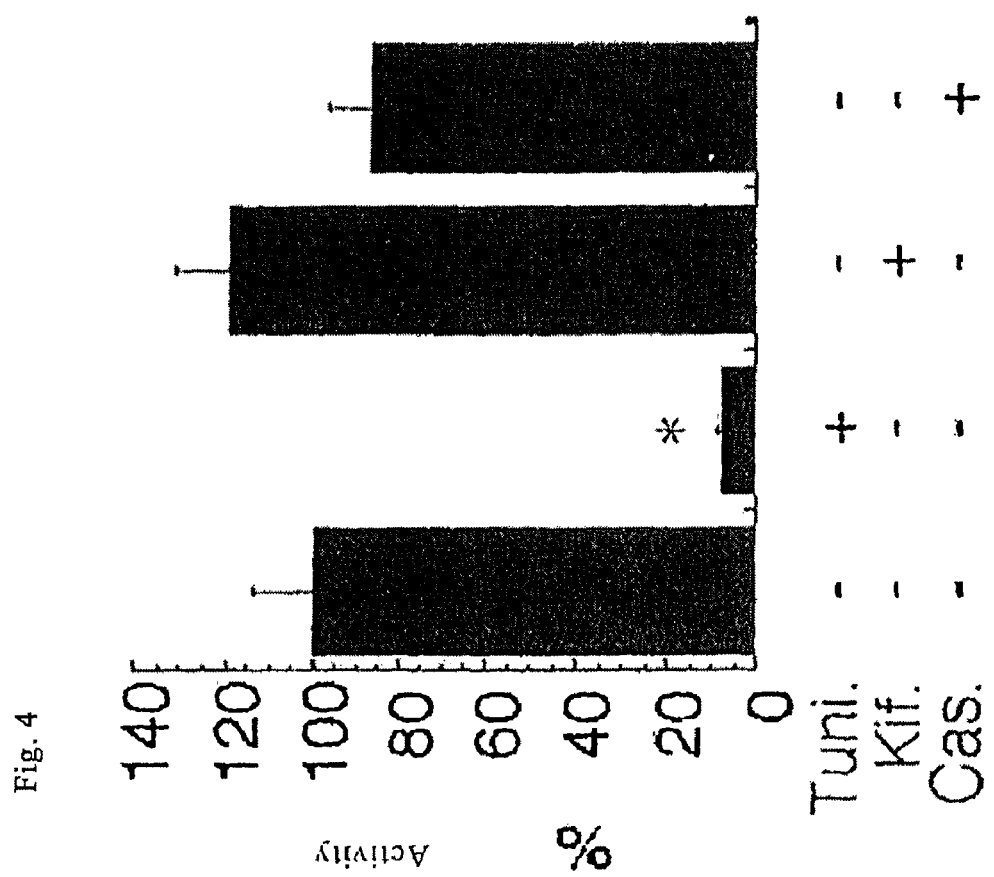

FIG. 4 indicates that the activity of SAT-I to which no sugar chain was added by the treatment with tunicamycin decreased remarkably. On the other hand, SAT-I that retained the high mannose type sugar chain obtained by the treatment with Kifnecin or castanospermine had an activity equivalent to that of mSAT-I subjected to treatment without the inhibitors. These results indicated that a high mannose type sugar chain is essential for the activity of SAT-I and interaction with calnexin or calreticulin is unnecessary in the process of usual SAT-I folding.

(4) Creation of "N180Q", "N224Q", "N334Q", and "N180Q, N224Q, N334Q" Mutants

Mutants (i.e., "N180Q", "N224Q", "N334Q", and "N180Q, N224Q, N334Q") in which any one or all of Asns in three N-glycosylation sites (i.e., N180, N224, and N334) present in mSAT-I was substituted by Gln were created.

Figure 5:
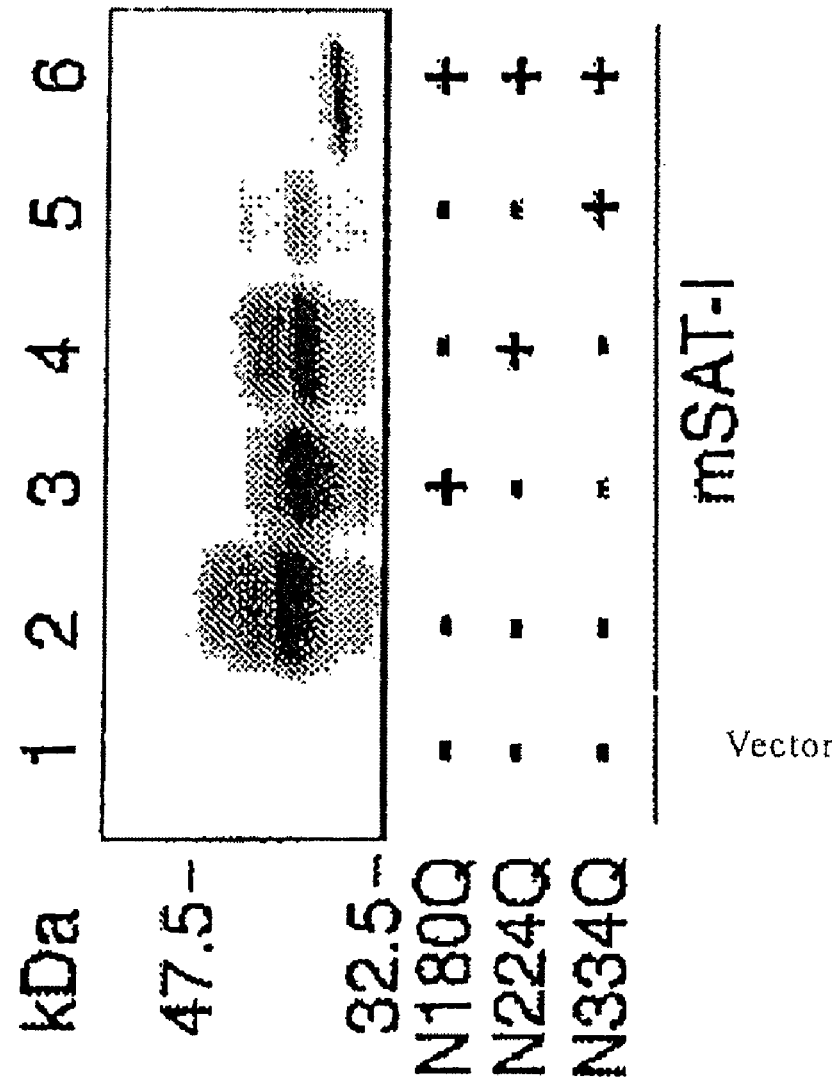

These mutants were transiently expressed in CHO cells and the cell lysates were subjected to SDS-PAGE and immunoblotting with an anti-SAT-I antibody was performed. Results are shown in FIG. 5.

As a result, a decrease in molecular weight was observed in all the mutant and the "N180Q, N224Q, N334Q" mutant had the same molecular weight as that of the wild type mSAT-I treated with PNGase.

Further, in the N334Q mutant and the "N180Q, N224Q, N334Q" mutant, the amount of SAT-I remarkably decreased. The above-mentioned results indicated that a sugar chain was added to all the three N-glycosylation sites in mSAT-I and no modification of sugar chain occurred in other sites.

Figure 6:
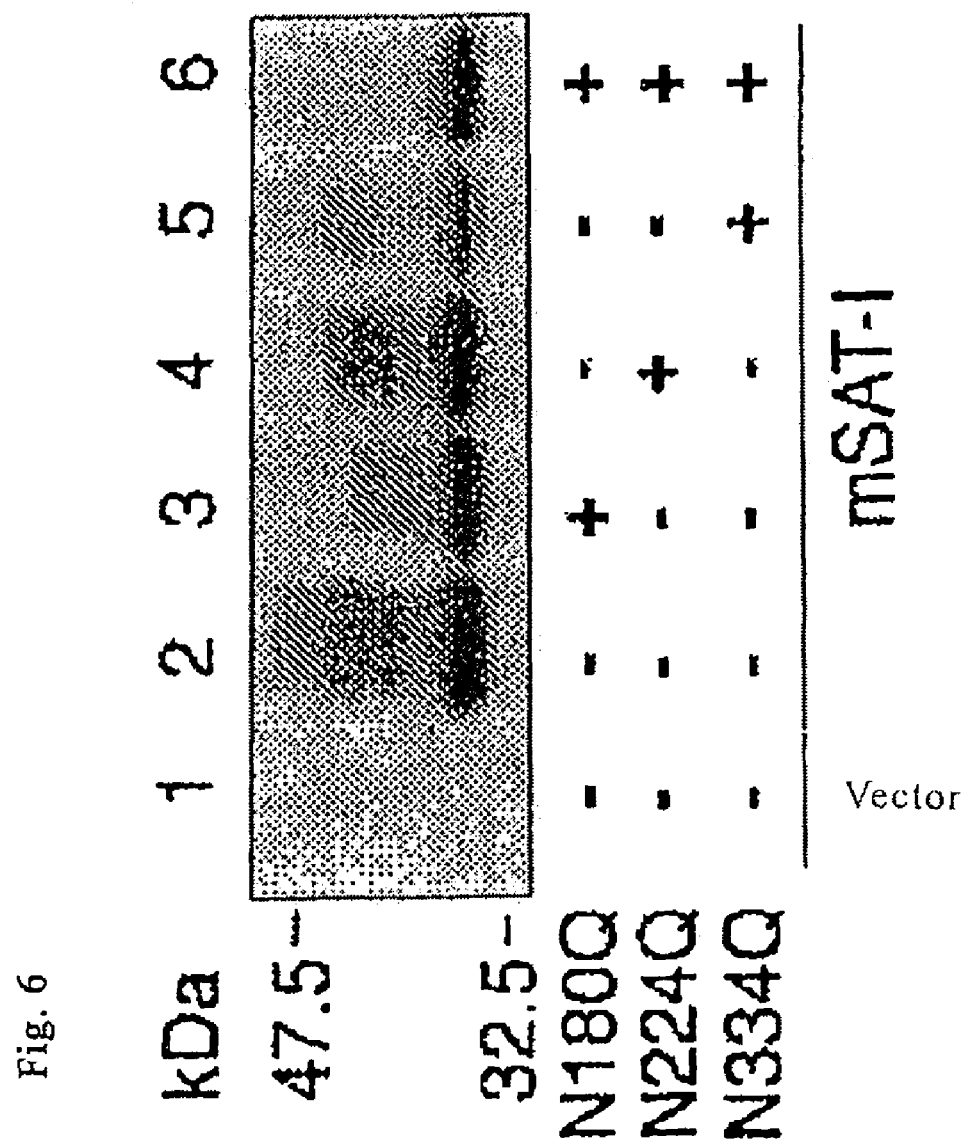

Then, the lysates of the cells in which various mutants were respectively expressed were treated with Endo H (37° C., 1 hour), and the treated lysates were subjected to SDS-PAGE, followed by immunoblotting with an anti-SAT-I antibody. Results are shown in FIG. 6.

As a result, Endo H-resistant band specifically decreased in the N180Q mutant. The decrease in Endo H-resistant band in the N334Q mutant was thought to be non-specific thereto from the fact that the Endo H-sensitive band similarly decreased.

Figure 7:
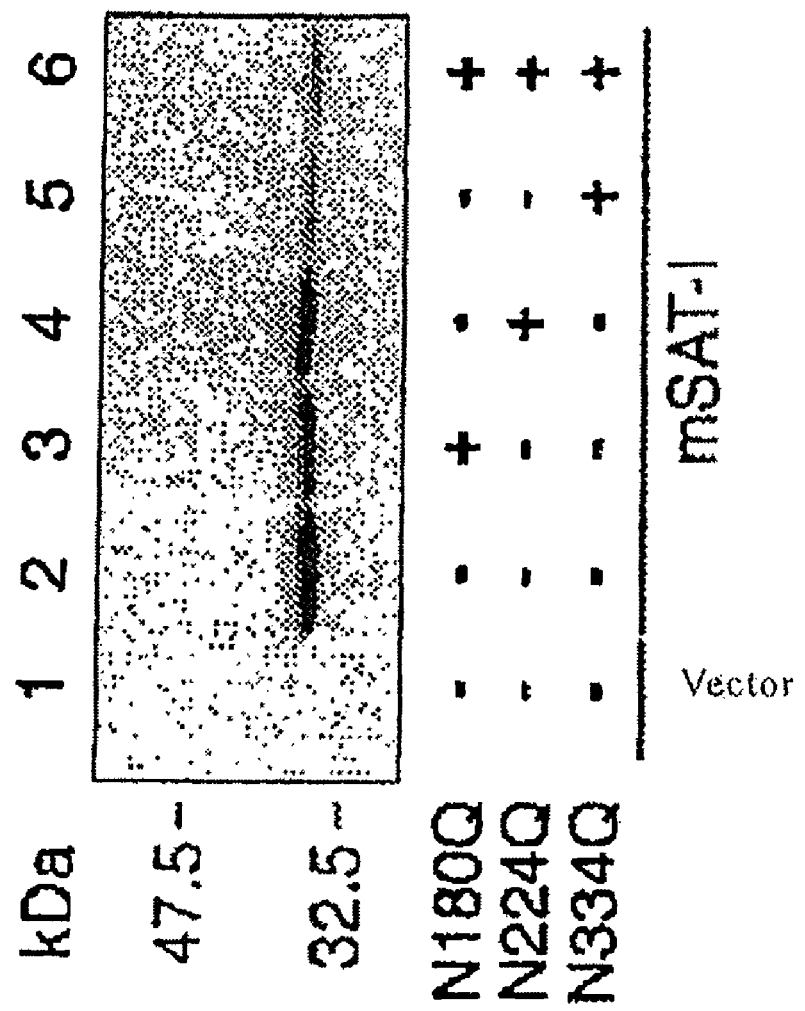
Figure 8:
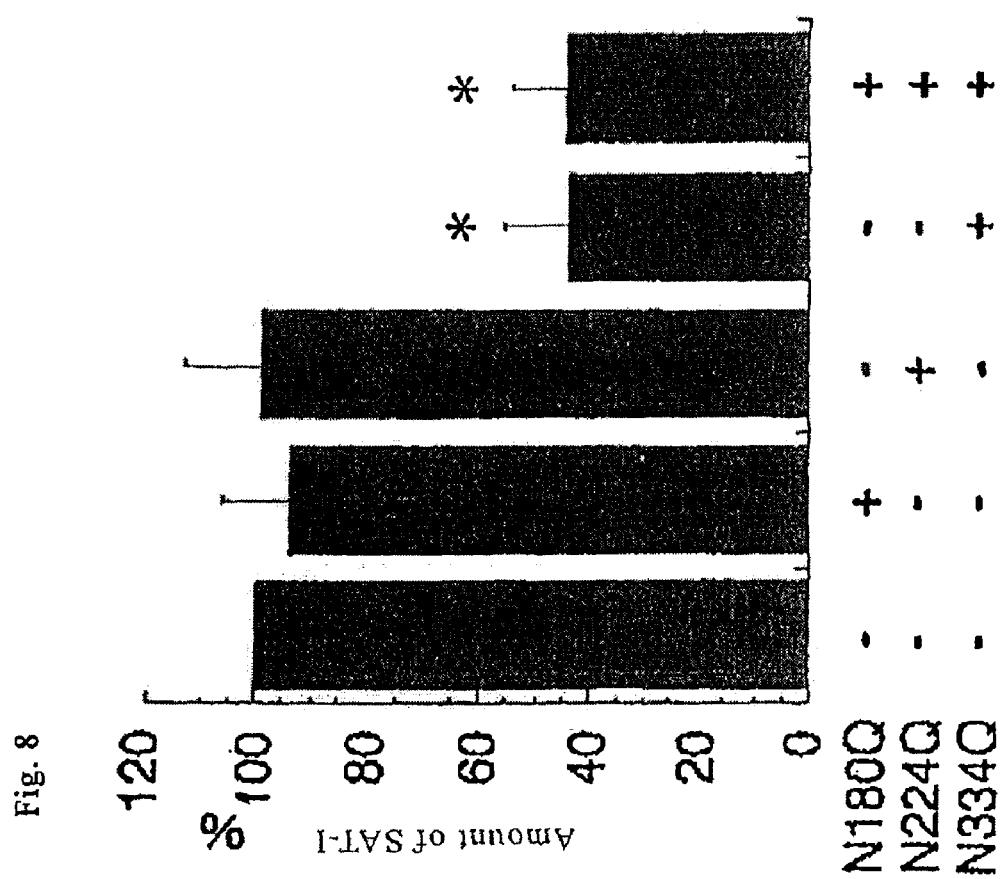
FIG. 8 is a diagram showing results of FIG. 7 (i.e., total amount of SAT-I) in numerical values. "*" indicates a significant difference with respect to the wild type at p<0.05.
Figure 9:
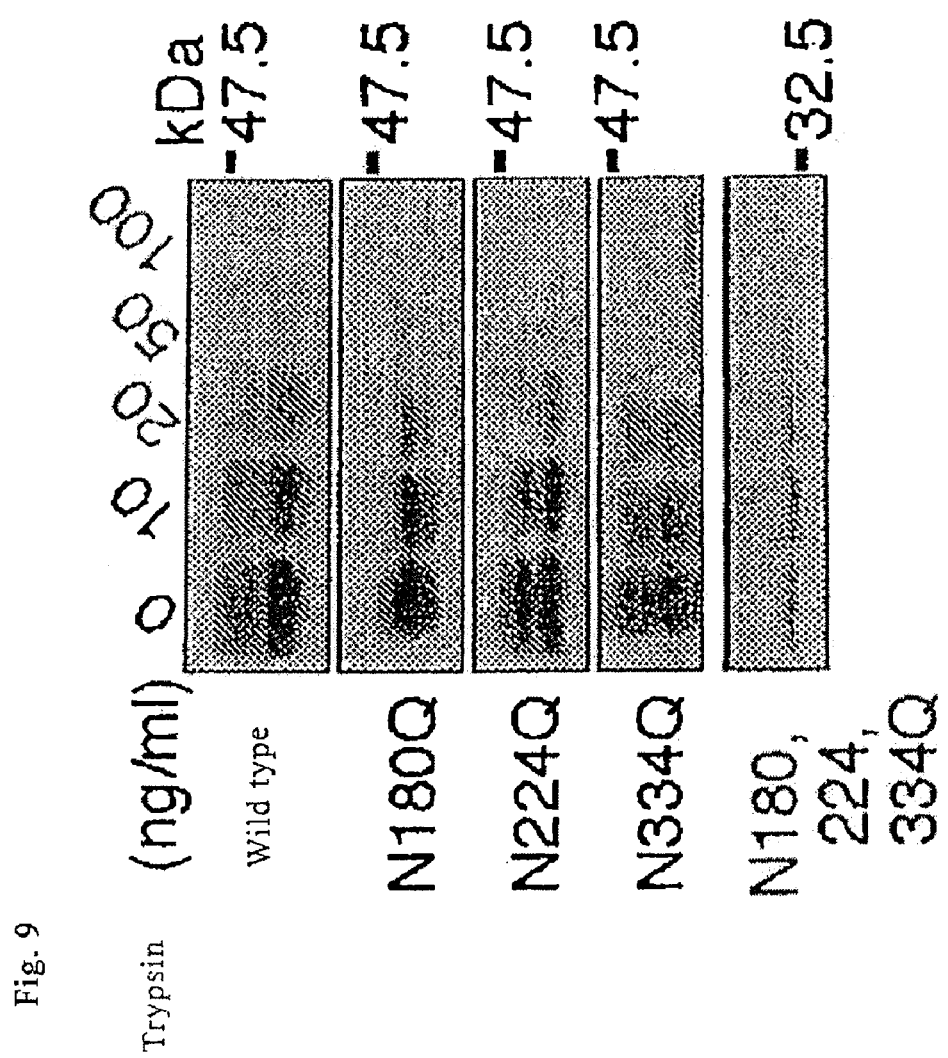
FIG. 9 is a diagram (photograph) showing sensitivity of the mSAT-I mutant to trypsin.

Then, the lysates of the cells in which various mutants were respectively expressed were treated with PNGase F (37° C., 1 hour), and the treated lysates were subjected to SDS-PAGE, followed by immunoblotting with an anti-SAT-I antibody, to compare the amount of total SAT-I. Results of immunoblotting are shown in FIG. 7 and results of numerical conversion of the amount (mean value of three immunoblotting results) based on the results in FIG. 7 are shown in FIG. 8.

As a result, in the mutant N334Q and the mutant "N180Q, N224Q, N334Q", a decrease in amount of protein of about 50% was indicated as compared with the wild type. However, when the cells were treated with tunicamycin, no such decrease was found, and it is unlikely that the sugar chain participates in the decrease in an amount of SAT-I. Further, results of a pulse label experiment with [$^{35}5$]-methionine indicated that the decrease occurred at the level of translation of protein. Therefore, it is considered that since the secondary structure of the mRNA was remarkably changed by mutation, the translation efficiency to a protein decreased. As a result, the amount of the proteins of the mutant N334Q and the mutant "N180Q, N224Q, N334Q" decreased.

(5) Comparison of Trypsin Sensitivities Among Various Mutants

An increase in sensitivity to proteases such as trypsin due to a miss folding of a protein has been known. Therefore, whether the structures of the mutants "N 180Q", "N224Q", "N334Q", and "N180Q, N224Q, N334Q" were significantly changed was examined by comparing sensitivities of the mutants to trypsin. That is, mSAT-I was transiently expressed by using CHO cells, and a lysate of the cells was prepared. The lysate were treated with 0, 10, 20, 50, or 100 ng/ml trypsin at 37° C. for 1 hour. Results are shown in FIG. 9.

As shown in FIG. 9, no significant difference was observed in the sensitivity to trypsin between the wild type and the mutants. Therefore, it was suggested that the possibility that lack of sugar chains would remarkably change the conformation of SAT-I was low.

(6) Influence of Sugar Chain on mSAT-I Activity

Each mutant was transiently expressed by using CHO cells and the cell lysates were used as an enzyme source and their enzyme activities were assayed. Results are shown in FIG. 10.

As a result, in all the mutants N180Q, N224Q, N334Q, and "N180Q, N224Q, N334Q", the activities decreased remarkably as compared with the wild type. In particular, the mutant N180Q had an activity lower than those of the mutants N224Q and N334Q, and in the mutant "N180Q, N224Q, N334Q" in which no sugar chain was linked, almost all the enzyme activity was lost. The above-mentioned results indicated that the presence of each sugar chain was essential for the enzyme activity of mSAT-I.

(7) Retention of Function of N-Linked Sugar Chains by Amino Acid Substitution (Retention of Physiological Activity of Protein)

Whether the function of an N-linked sugar chain is retained by substituting an amino acid at a particular portion (whether the physiological activity of the protein is retained without N-linked sugar chains modification) was examined by using mSAT-I.

First, sugar chains which link to N224 were examined. Mutants N224K (SEQ ID NO: 6) and N224D were created and their activities were compared with those of the wild type and the mutant N224Q.

These mutants were transiently expressed by using CHO cells and the cell lysates were subjected to SDS-PAGE, and immunoblotting with an anti-SAT-I antibody was performed. Results are shown in FIG. 11. The results indicated that the mutants N224K and N224D showed band patterns similar to that of the mutant N224Q.

The results of assay of the SAT-I activity of each mutant are shown in FIG. 12. The results indicated that the mutant N224K showed an activity of the same level as that of the wild type. On the other hand, in the mutant N224D in which substitution was made by D (Asp) having an opposite charge to K (Lys), the activity decreased more than that of the mutant N224Q. These results indicated that the function of the sugar chain which links to N224 was retained by substituting N224 by K (Lys) having a positive charge. The results also indicated that by performing such a substitution of an amino acid, the physiological activity (the enzymatic activity of SAT-0 of the protein was retained without N-linked sugar chain modification.

Then, the sugar chain which links to N334 was examined. The mutants N334K and T336Q (SEQ ID NO: 8) were created and their activities were compared with those of the wild type and a mutant N334Q.

These mutants were transiently expressed by using CHO cells and the cell lysates were subjected to SDS-PAGE, and immunoblotting with an anti-SAT-I antibody was performed. Results are shown in FIG. 13. The results indicated that both the mutants N334K and T336Q showed band patterns similar to that of the mutant N334Q.

Further, results of assay of SAT-I activity of each mutant are shown in FIG. 14. The results indicated that the mutant N334K only showed an activity of the same level as that of the mutant N334Q while the mutant T336Q showed an activity about 1.5 folds higher than that of the wild type. These results indicated that the function of the sugar chain which links to N334 was retained by substituting T336 by Q (Gln). The results also indicated that by performing such a substitution of an amino acid, the physiological activity (the enzymatic activity of SAT-I) of the protein was retained without N-linked sugar chain modification.

Then, the sugar chain which links to N180 was examined. Mutants N180K, N180S (SEQ ID NO: 10), "H177D, N180S" (SEQ ID NO: 12), and H177D (SEQ ID NO: 14) were created and their activities were compared with those of the wild type and a mutant N180Q.

These mutants were transiently expressed by using CHO cells and the cell lysates were subjected to SDS-PAGE, and immunoblotting with an anti-SAT-I antibody was performed. Results are shown in FIG. 15. The results indicated that the mutants N 180S and "H177D, N180S" had a major band around 42 kDa similar to that of the mutant N180Q and the mutant N180K had major bands at around 42 kDa and 40 kDa. The mutant H177D showed a similar band pattern to that of the wild type.

Further, results of assay of SAT-I activity of each mutant are shown in FIG. 16. The results indicated that the mutant N180K only showed an activity of the same level as that of the mutant N180Q while the mutant N180S showed an activity of about 50% of that of the wild type, and the mutant "H177D, N180S" had an activity equivalent to or higher than that of the wild type. Further, the mutant H177D showed an activity of about 1.5 folds higher than that of the wild type. These results indicated that the function of the sugar chain which links to N180 was retained by substituting H177 by D (Asp) and/or substituting N180 by S (Ser). The results also indicated that by performing such a substitution of an amino acid, the physiological activity (the enzymatic activity of SAT-I) of the protein was retained without N-linked sugar chain modification.

Then, the mutant "N180S, N224K, T336Q" having no sugar chain modification site and the mutant "H177D, N180S, N224K, T336Q" (SEQ ID No: 16) were created and their activities were compared with those of the wild type and the mutant "N180Q, N224Q, N334Q".

Figure 17:
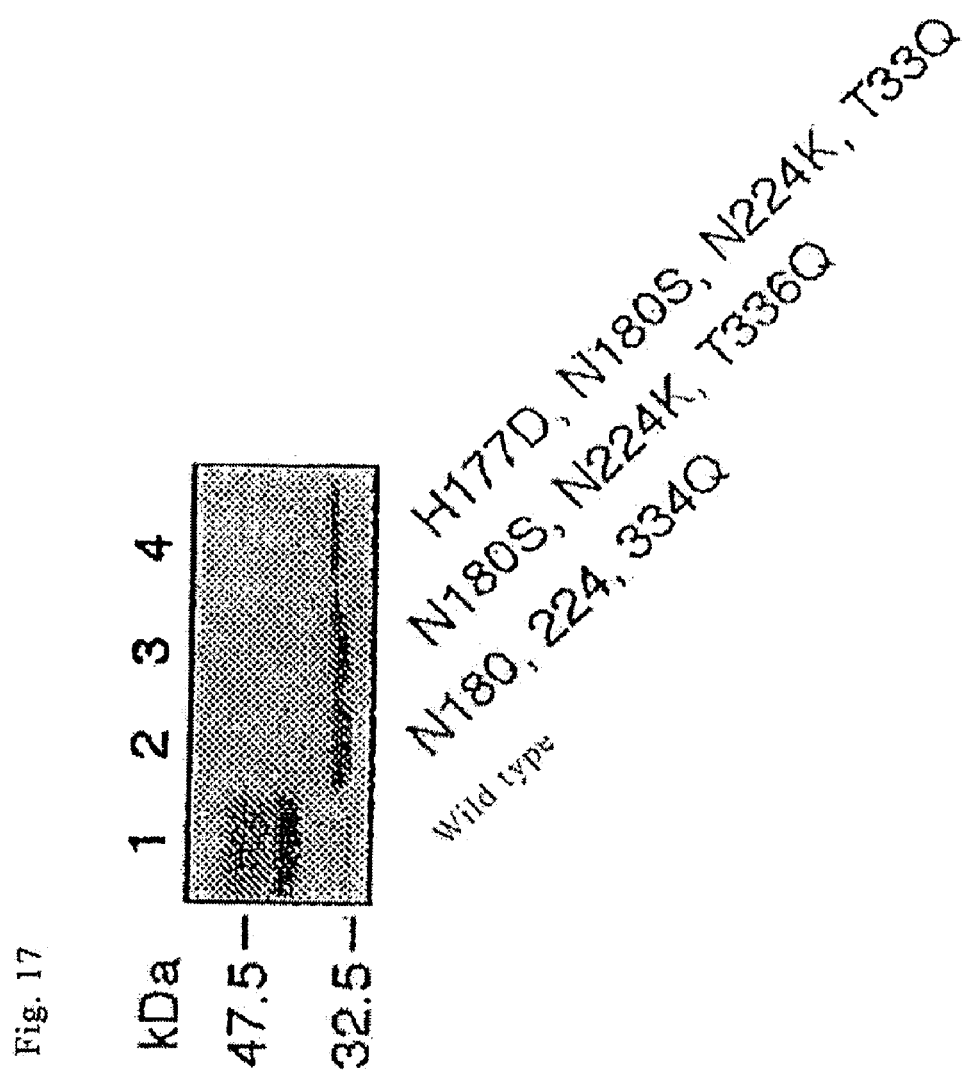
Figure 20:
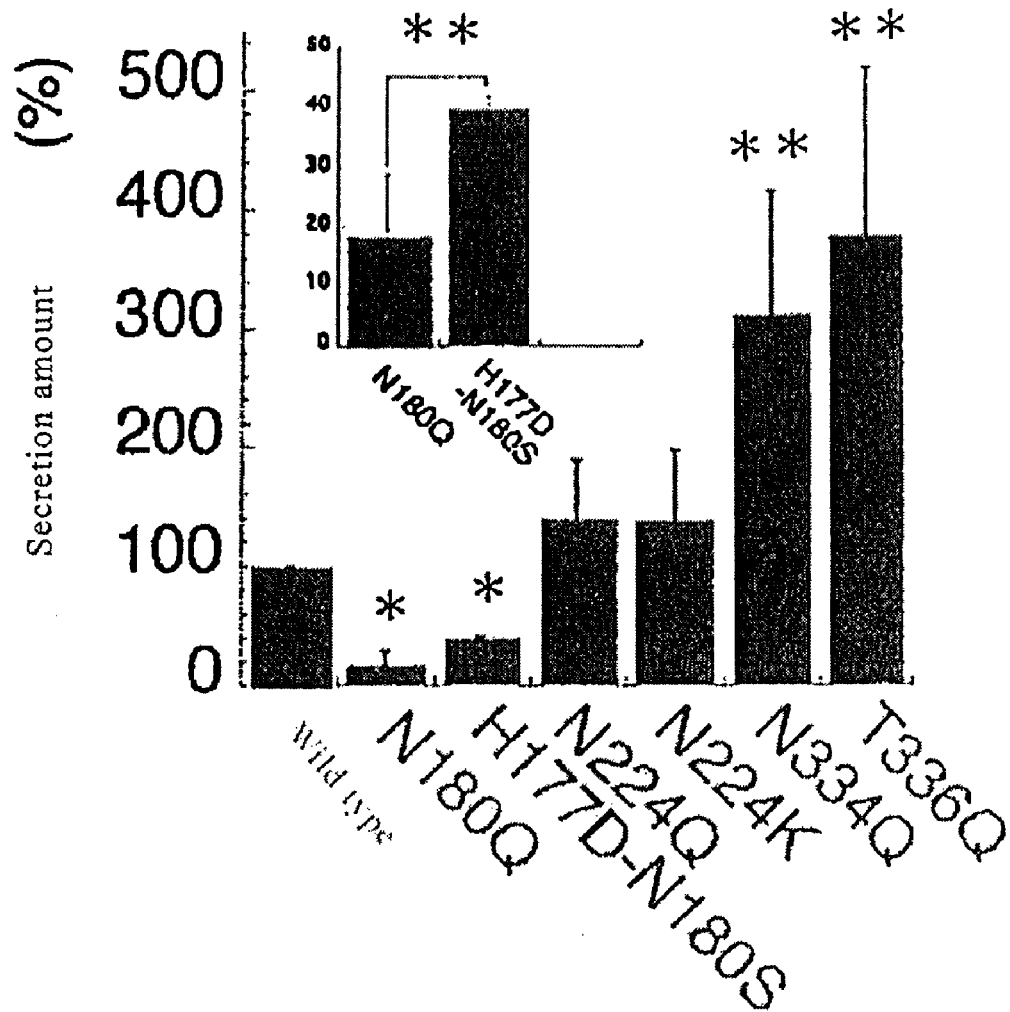

These mutants were transiently expressed by using CHO cells and the cell lysates were subjected to SDS-PAGE, and immunoblotting with an anti-SAT-I antibody was performed. Results are shown in FIG. 17. The results indicated that both mutants showed a band around 35 kDa in a manner similar to the case of PNGase F treatment.

Further, results of assay of SAT-I activity of each mutant are shown in FIG. 18. The results indicated that the mutant "N180S, N224K, T336Q" showed an activity of about 40% of that of the wild type, and the mutant "H177D, N180S, N224K, T336Q" showed an activity of about 50% of that of the wild type. Further, separately, the mutant "N224K, T336Q" (SEQ ID NO: 18) was created and the activity of SAT-I was assayed similarly. As a result, the mutant showed an activity equivalent to that of the wild type.

The results indicated that, in the amino acid sequence of N-linked glycoprotein having the amino acid sequence motif (I) and/or (II) described below, substitution of an amino acid in the amino acid sequence motif (I) and/or (II) by other amino acid(s) according to one or more of rules (A) to (C) described below allowed the physiological activity of the glycoprotein before the mutation is introduced to be retained without being subjected to modification by an N-linked sugar chain in the following amino acid sequence containing the amino acid to be substituted:

(I) Asn Xa1 Xa2 (SEQ ID NO: 1); and (II) Xa3 Val Gly Asn Xa1 Xa2 (SEQ ID NO: 2)

(in the amino acid sequence motif (I) and (II), Xa1 indicates an amino acid other than Pro, Xa2 indicates Thr or Ser, and Xa3 indicates His or Asp);

(A) substitution of Asn by Lys or Ser;

(B) substitution of Xa2 by Gln; and (C) substitution of Xa3 by Asp.

(8) Influence of Amino Acid Substitution on Extracellular Secretion

Experiments on the extracellular secretion of SAT-I were performed.

In a similar manner as the transfection using the above-described CHO cells, HEK293 cells were cultured in a Dulbecco modified Eagle medium and SAT-I was transiently expressed in the HEK293 cells by using a pcDNA3 vector having a wild type mSAT-I inserted therein (wild type pcDNA3.1 Zeo(+)-mST3Gal-V). After the culture, the cell lysates and the culture were separately collected and the lysate of the cell lysates and the culture were subjected to SDS-PAGE, and immunoblotting with an anti-SAT-I antibody was performed. Further, each of the lysate of the cells and the medium was treated with PNGase F and then immunoblotting was similarly performed, and the results thereof were compared (FIG. 19). As a control, the pcDNA3 vector was used.

SAT-I secreted in the medium showed broad bands of 45 kDa and 38 kDa. It was predicted that the 45 kDa band retains an N-linked sugar chain since the 45 kDa band was not detected in immunoblotting after the PNGase F treatment. The 45 kDa band was resistant to Endo H.

Further, by using the HEK293 cells, various mutants of mSAT-I created as described above (the mutants N180Q, "H177D, N180S", "N224Q", N224K, N334Q, and T336Q) and the wild type mSAT-I were transiently expressed, and mSAT-I extracted from the cell lysates and mSAT-I secreted in the culture were subjected to PNGase F treatment and then subjected to SDS-PAGE, and immunoblotting with an anti-SAT-I antibody was performed. The bands were analyzed by measuring concentrations thereof, and a ratio of the amount of protein secreted to the substrate to the amount of protein present in the cells was calculated. Further, setting the ratio of the wild type mSAT-I as 100%, the secretion amount of each mutant was calculated (FIG. 20).

The secretion amounts of the mutant N224Q and of the mutant N224K were substantially the same as that of the wild type. On the other hand, the mutant N180Q had a secretion amount of 20% of that of the wild type and the mutant "H177D, N180S" had a secretion amount of 50% of the wild type. Surprisingly, the mutant N334Q and the mutant T336Q had a secretion amount higher than 300% of the wild type. These results revealed that the N-linked sugar chain linked to the N at the 180th position in SAT-I played an important role in secretion into a medium and on the other hand, the N-linked sugar chain linked to the N at the 334th position participates in the function of retaining the protein in the cells.

The secretion amount of the mutant "H177D, N180S" which retained an activity substantially equivalent to that of the wild type was approximately two times the secretion amount of the mutant N180Q which showed an activity of only about 20% of the activity of the wild type.

The mutant N180Q had an abnormal structure that is enzymatically inactive due to loss of the N-linked sugar chain, so it had an activity of about 20% of the wild type and a secretion amount of about 20% of the wild type. On the other hand, the mutant "H177D, N180S" had an enzyme activity substantially equivalent to that of the wild type, so it was suggested that it retained the enzyme activity structure. It was predicted that the decrease in the secretion amount was due to the loss of the N-linked sugar chain linked to the N at the 180th position.

These results suggested that not only the N-linked sugar chain linked to N at the 180th position but also the protein structure near this site is involved in the activity and secretion of SAT-I.

When the protein of the present invention is produced by genetic engineering, regulation of the function relating to the extracellular secretion is important. The method of obtaining the target protein of the present invention from the culture medium is more convenient and efficient than the method of obtaining the target protein of the present invention from cultured cells.

(9) Expression of Mutant "H177D, N180S, N224K, T336Q" of mSAT-I in *Escherichia coli*

(i) Expression of Mutant mSAT-I in *Escherichia coli*

Expression of mutant mSAT-I in *Escherichia coli* was performed in a Cold Shock Expression System (manufactured by TaKaRa Bio Co., Ltd.).

Specifically, an *Escherichia coli* BL21 strain was transformed with Chaperon plasmid pG-Tf2 (manufactured by TaKaRa Bio Co., Ltd.) to create BL21-pG-Tf2 and then competent cells of the *Escherichia coli* BL21 strain were prepared. Then, a (ΔTM) mutant mSAT-I gene in which a transmembrane region (TM) was deleted was introduced into SAT-I expression plasmids (Psu141 and Psu142) and the competent cell was transformed again with these plasmids to create BL21-pG-Tf2-pSU141 and BL21-pG-Tf2-pSU142. The cells were preincubated in 1 ml of an LB medium (tryptone, yeast extract, NaCl, pH 7.2) at 37° C. and then the preincubated cells were added to the LB medium so that the preincubated cells are diluted such that optical density OD at 600 nm was 0.1. At the same time, tetracycline was added up to 5 ng/ml and the cells were cultured at 37° C. until optical density OD at 600 nm was 0.53. Then, the culture temperature was changed to 15° C. and culture was continued for additional 30 minutes. After that, IPTG (isopropyl (3-D-thiogalactopyranoside/manufactured by SIGMA) was added to the medium up to 0.01 mmol/l and the cells were cultured at 15° C. for 48 hours. After completion of the culture, cells were collected by centrifugation. The collected cells were suspended in PBS containing 1 ml of 1 mmol/l fluorinated 4-(2-aminoethyl)benzenesulfonyl hydrochloride (ABESF; protease inhibitor) and sonicated twice for 30 seconds, and then centrifuged at 20,000×g for 15 minutes to collect a supernatant.

As a control, expression of wild type ΔTM-mSAT-I was similarly performed.

(ii) Purification of Mutant mSAT-I Expressed in *Escherichia coli*

Then, purification of mutant mSAT-I was performed. First, Ni-NTA superflow (manufactured by QIAGEN) was aliquoted in a 1.5-ml tube so that the amount of gel was 10 μl, and 100 μl of PBS containing 0.01% Triton X-100 was added thereto and the gel was allowed to be mixed well. Then, the gel was subjected to equilibration treatment and centrifuged to remove a supernatant. Further, the supernatant obtained in the section (i) mentioned above was aliquoted and gently mixed with the gel by tapping and then the mixture was allowed to react at 4° C. for 2 hours in a rotary mixer. After the reaction, the reaction mixture was centrifuged to remove the supernatant and wash buffer (composition: 50 mM NaH$_2$PO$_4$ (pH 8.0), 300 mM NaCl, 20 mM imidazole, 0.01% Triton X-100) was added thereto. The resultant mixture was centrifuged again to remove a supernatant, and elute buffer (composition: 50 mM NaH$_2$PO$_4$ (pH 8.0), 300 mM NaCl, 125 mM imidazole) was added thereto. The resultant mixture was gently mixed by tapping and centrifuged again to collect the supernatant. The collected supernatant was used as an Ni-affinity-purified sample.

Similarly, wild type mSAT-I was purified.

Further, imidazole in the elute buffer mentioned above was dialyzed and substituted by 20 mM Tris hydrochloride (pH 7.2) and 150 mM NaCl and used as an enzyme source as described in the section (iii) below.

(iii) Assay of Activity of Mutant mSAT-I

After a solvent (chloroform:methanol=1:1) of LacCer solution was dried 4× Reaction mixture was added four times and LacCer was suspended by sonication. Further, only 50 μl of 3 mM CMP-sialic acid, 100 μl of an enzyme source, and buffer (composition: 20 mM Tris hydrochloride, 150 mM NaCl, pH 7.2) were added and the resultant was allowed to react at 37° C. for 2 hours. Ganglioside GM3 was purified from the reaction solution by means of Sep-Pak Plus18 and then was applied to an HPTLC plate. At the same time, a standard substance of GM3 (0.25 or 0.05 μg) was added. As a developing solvent, chloroform/methanol/0.2% CaCl$_2$ (55/45/10) was used to separate lipids. All the lipids were thermally transferred from the HPTLC plate to a PVDF membrane. The obtained PVDF membrane was dried and then blocked with blocking buffer to allow a primary antibody (M2590 which is an IgM monoclonal antibody specific to GM3 was used) to react with the membrane in the blocking buffer. After the PVDF membrane was well washed with TBS-T buffer, the PVDF membrane was allowed to react with a secondary antibody (anti-murine IgM antibody labeled with HRP) in the blocking buffer. The PVDF membrane was well washed with TBS-T buffer, and then the PVDF membrane was allowed to develop chemiluminescences with an ECL kit (manufactured by Amersham Biosciences) and GM3 was detected with an X-ray film.

Similarly, wild type mSAT-I that was expressed in *Escherichia coli* was also assayed for its activity.

Figure 21:
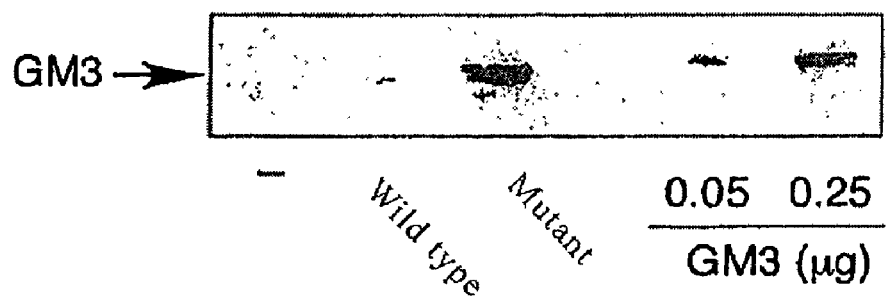

From the results (FIG. 21), 0.05 μg or less of GM3 was detected in the case of the wild type mSAT-I, and about 0.5 μg of GM3 was detected in the case of the mutant SAT-I. Those results suggested that the mutant mSAT-I had an activity 10 folds or more as compared with that of the wild type SAT-I.

These results indicated that the gene of the mutant SAT-I which was not modified with sugar chains was expressed in *Escherichia coli* and had an activity equivalent to that of the wild type. The mutant protein of the present invention is a protein which has an activity without sugar chain modification, so the mutant protein can be mass-produced by using microbial cells such as *Escherichia coli*, and thus is useful.

The present invention also encompasses a concept of a method of allowing a physiological activity of a protein to be retained without sugar chain modification, comprising: comparing amino acid sequences at a particular glycosylation site in N-linked glcoprotein or neighborhood sites including the same among a plurality of animal species to clarify differences in amino acid sequence between the animal species in which a sugar chain is linked at the glycosylation site and the animal species in which no sugar chain is linked at the glycosylation site; and substituting different amino acids in the animal species in which a sugar chain is linked at the glycosylation site by the corresponding amino acids in the animal species in which no sugar chain is linked at the glycosylation site.

The protein of the present invention is an N-linked glycoprotein in which a sugar chain that participates in expression of various functions, which retains the physiological activity of the glycoprotein without modification of a part of or the whole of the N-linked sugar chains. Hence a protein that has a function equivalent to that of the N-linked glycoprotein before the mutation is introduced can be produced conveniently, rapidly, in large amounts, and at low cost and further the quality of the protein to be produced can be maintained at a constant level. Therefore, the protein of the present invention is extremely useful. By utilizing the polynucleotide of the present invention, production of the protein of the present invention can be performed more conveniently and more rapidly, so the polynucleotide of the present invention is extremely useful. Further, the method of the present invention is extremely useful because it allows physiological functions of glycoproteins to be expressed without sugar chain modification. As described above, the present invention is extremely useful as a tool for synthesis or the like of pharmaceuticals, reagents, and various substances.

INDUSTRIAL APPLICABILITY

The protein of the present invention has a function which is equivalent to that of the N-linked glycoprotein before the mutation is introduced, so it can be utilized as a tool for synthesis of pharmaceuticals, reagents, and various substances or the like. The polynucleotide of the present invention can be utilized as a tool for production of the protein of the present invention or the like. Further, the method of the present invention can be applied to the production of the protein of the present invention or the like.

What is claimed is:

1. A mutant sialyltransferase-I (SAT-I) comprising the amino acid sequence of SEQ ID NO:4 into which at least one amino acid substitution selected from the group consisting of (a) to (d) shown below has been introduced:
   (a) substitution of Asn by Lys in the amino acid sequence motif (i) Asn Glu Ser (amino acids 224-226 of SEQ ID NO:4);
   (b) substitution of Thr by Gln in the amino acid sequence motif (ii) Asn Val Thr (amino acids 334-336 of SEQ ID NO:4);
   (c) substitution of Asn by Ser in the amino acid sequence motif (iii) His Val Gly Asn Lys Thr (SEQ ID NO: 43) (amino acids 177-182 of SEQ ID NO:4); and
   (d) substitution of His by Asp in the amino acid sequence motif (iii) His Val Gly Asn Lys Thr (SEQ ID NO: 43) (amino acids 177-182 of SEQ ID NO:4).

2. The mutant SAT-I according to claim 1, which comprises the amino acid sequence of SEQ ID NO: 6.

3. The mutant SAT-I according to claim 1, which comprises the amino acid sequence of SEQ ID NO: 8.

4. The mutant SAT-I according to claim 1, which comprises the amino acid sequence of SEQ ID NO: 10.

5. The mutant SAT-I according to claim 1, which comprises the amino acid sequence of SEQ ID NO: 12.

6. The mutant SAT-I according to claim 1, which comprises the amino acid sequence of SEQ ID NO: 14.

7. The mutant SAT-I according to claim 1, which comprises the amino acid sequence of SEQ ID NO: 16.

8. The mutant SAT-I according to claim 1, which comprises the amino acid sequence of SEQ ID NO: 18.

* * * * *

UNITED STATES PATENT AND TRADEMARK OFFICE
CERTIFICATE OF CORRECTION

PATENT NO. : 8,338,154 B2  
APPLICATION NO. : 12/943461  
DATED : December 25, 2012  
INVENTOR(S) : Inokuchi et al.

Page 1 of 2

It is certified that error appears in the above-identified patent and that said Letters Patent is hereby corrected as shown below:

In the Specifications:

In column 1 at line 62, Change ""H 177D"" to --"H177D"--.

In column 2 at line 42, Change "tetradon" to --tetraodon--.

In column 3 at line 56, Change "SAT-1" to --SAT-I--.

In column 5 at line 15, Change "mSAT-1" to --mSAT-I--.

In column 5 at line 18, Change "mSAT-1" to --mSAT-I--.

In column 5 at line 20, Change "mSAT-1" to --mSAT-I--.

In column 5 at line 21, Change ""*"" to --"**"--.

In column 5 at line 24, Change "mSAT-1" to --mSAT-I--.

In column 5 at line 26, Change "mSAT-1" to --mSAT-I--.

In column 5 at line 27, Change ""*"" to --"**"--.

In column 5 at line 30, Change "mSAT-1" to --mSAT-I--.

In column 5 at line 32, Change "mSAT-1" to --mSAT-I--.

In column 8 at line 21, Change "SAT-1" to --SAT-I--.

In column 9 at line 1, Change "SAT-1" to --SAT-I--.

In column 11 at line 56, Change "Lny" to --Lnγ--.

In column 14 at line 14, Change "Mass.))." to --Mass).--.

In column 14 at line 66, Change "2.5" to --2.5 μg/ml,--.

In column 17 at line 33, Change "tetradon" to --tetraodon--.

In column 17 at line 42, Change "tetradon," to --tetraodon,--.

In column 19 at line 27, Change "[$^{35}$5]" to --[$^{35}$S]--.

In column 19 at line 38, Change ""N 180Q"," to --N180Q",--.

In column 20 at line 57, Change "N 180S" to --N180S--.

Signed and Sealed this  
Ninth Day of July, 2013

Teresa Stanek Rea  
*Acting Director of the United States Patent and Trademark Office*

CERTIFICATE OF CORRECTION (continued)
U.S. Pat. No. 8,338,154 B2

In column 23 at line 11, Change "(3" to --(β--.

In column 24 at line 26, Change "glcoprotein" to --glycoprotein--.

UNITED STATES PATENT AND TRADEMARK OFFICE
CERTIFICATE OF CORRECTION

| | |
|---|---|
| PATENT NO. | : 8,338,154 B2 |
| APPLICATION NO. | : 12/943461 |
| DATED | : December 25, 2012 |
| INVENTOR(S) | : Inokuchi et al. |

It is certified that error appears in the above-identified patent and that said Letters Patent is hereby corrected as shown below:

In the Specification

In column 12 at line 64, Change "tetradon." to --tetraodon.--.

Signed and Sealed this
Thirteenth Day of August, 2013

Teresa Stanek Rea
*Acting Director of the United States Patent and Trademark Office*

SEQUENCE LISTING

<160> NUMBER OF SEQ ID NOS: 43

<210> SEQ ID NO 1
<211> LENGTH: 3
<212> TYPE: PRT
<213> ORGANISM: Artificial sequence
<220> FEATURE:
<223> OTHER INFORMATION: Description of Artificial Sequence: Chemically
      synthesized
<220> FEATURE:
<221> NAME/KEY: misc_feature
<222> LOCATION: 2
<223> OTHER INFORMATION: Xaa = any amino acid other than Pro
<220> FEATURE:
<221> NAME/KEY: misc_feature
<222> LOCATION: 3
<223> OTHER INFORMATION: Xaa = Thr or Ser

<400> SEQUENCE: 1

Asn Xaa Xaa
1

<210> SEQ ID NO 2
<211> LENGTH: 6
<212> TYPE: PRT
<213> ORGANISM: Artificial sequence
<220> FEATURE:
<223> OTHER INFORMATION: Description of Artificial Sequence: Chemically
      synthesized
<220> FEATURE:
<221> NAME/KEY: misc_feature
<222> LOCATION: 1
<223> OTHER INFORMATION: Xaa = His or Asp
<220> FEATURE:
<221> NAME/KEY: misc_feature
<222> LOCATION: 5
<223> OTHER INFORMATION: Xaa = any amino acid other than Pro
<220> FEATURE:
<221> NAME/KEY: misc_feature
<222> LOCATION: 6
<223> OTHER INFORMATION: Xaa = Thr or Ser

<400> SEQUENCE: 2

Xaa Val Gly Asn Xaa Xaa
1               5

<210> SEQ ID NO 3
<211> LENGTH: 1080
<212> TYPE: DNA
<213> ORGANISM: Mus musculus
<220> FEATURE:
<221> NAME/KEY: CDS
<222> LOCATION: (1)..(1080)
<223> OTHER INFORMATION: Open reading frame

<400> SEQUENCE: 3

```
atg aga aga ccc agc ttg tta ata aaa gac atc tgc aag tgc acg ttg      48
Met Arg Arg Pro Ser Leu Leu Ile Lys Asp Ile Cys Lys Cys Thr Leu
1               5                   10                  15 gtt gca ttt gga gtc tgg ctc ctg tac atc ctc att ttg aat tac acc      96
Val Ala Phe Gly Val Trp Leu Leu Tyr Ile Leu Ile Leu Asn Tyr Thr
            20                  25                  30 gct gaa gaa tgt gac atg aaa aga atg cac tat gtg gac cct gac cgg     144
Ala Glu Glu Cys Asp Met Lys Arg Met His Tyr Val Asp Pro Asp Arg
        35                  40                  45 ata aag aga gct cag agc tat gct cag gaa gtc ttg cag aag gaa tgt     192
Ile Lys Arg Ala Gln Ser Tyr Ala Gln Glu Val Leu Gln Lys Glu Cys
    50                  55                  60
```

| | | |
|---|---|---|
| cgg ccc agg tac gcg aag acg gct atg gct ctg tta ttt gag gac agg<br>Arg Pro Arg Tyr Ala Lys Thr Ala Met Ala Leu Leu Phe Glu Asp Arg<br>65                   70                       75                   80 | 240 |
| tac agc atc aac ttg gag cct ttt gtg cag aag gtc ccc acg gcc agt<br>Tyr Ser Ile Asn Leu Glu Pro Phe Val Gln Lys Val Pro Thr Ala Ser<br>               85                     90                     95 | 288 |
| gaa gct gag ctc aag tat gac ccg cct ttt gga ttc cgg aag ttc tcc<br>Glu Ala Glu Leu Lys Tyr Asp Pro Pro Phe Gly Phe Arg Lys Phe Ser<br>            100                    105                 110 | 336 |
| agt aaa gtc cag agc ctc ttg gat atg ctg ccc gaa cat gac ttt tct<br>Ser Lys Val Gln Ser Leu Leu Asp Met Leu Pro Glu His Asp Phe Ser<br>          115                   120                125 | 384 |
| gaa cac ttg aga gcc aag gcc tgc aag cgc tgt gtg gtt ggg aac<br>Glu His Leu Arg Ala Lys Ala Cys Lys Arg Cys Val Val Val Gly Asn<br>130                   135                   140 | 432 |
| ggg ggc atc ctg cac gga cta gag ctg ggt cac gcc ctc aac cag ttc<br>Gly Gly Ile Leu His Gly Leu Glu Leu Gly His Ala Leu Asn Gln Phe<br>145                   150                   155                160 | 480 |
| gat gtg gta ata agg ttg aac agt gcg cca gtt gag ggt tac tct gaa<br>Asp Val Val Ile Arg Leu Asn Ser Ala Pro Val Glu Gly Tyr Ser Glu<br>                    165                  170                175 | 528 |
| cac gtt ggg aat aaa act act ata agg atg act tac cca gag ggt gcg<br>His Val Gly Asn Lys Thr Thr Ile Arg Met Thr Tyr Pro Glu Gly Ala<br>            180                    185                 190 | 576 |
| cca ctg tcg gac gtt gaa tac tac gcc aat gat ttg ttc gtt act gtt<br>Pro Leu Ser Asp Val Glu Tyr Tyr Ala Asn Asp Leu Phe Val Thr Val<br>          195                   200                205 | 624 |
| tta ttt aag agt gtt gat ttc aag tgg ctt caa gca atg gta aaa aat<br>Leu Phe Lys Ser Val Asp Phe Lys Trp Leu Gln Ala Met Val Lys Asn<br>210                   215                   220 | 672 |
| gaa agc ctg ccc ttt tgg gtt cgc ctc ttc ttt tgg aag caa gtg gca<br>Glu Ser Leu Pro Phe Trp Val Arg Leu Phe Phe Trp Lys Gln Val Ala<br>225                   230                   235                240 | 720 |
| gaa aaa gtc cca ctc cag cca aag cac ttc agg att ttg aac cca gtt<br>Glu Lys Val Pro Leu Gln Pro Lys His Phe Arg Ile Leu Asn Pro Val<br>                    245                  250                255 | 768 |
| atc atc aaa gaa act gcc ttc gac atc ctt cag tac tca gag cct cag<br>Ile Ile Lys Glu Thr Ala Phe Asp Ile Leu Gln Tyr Ser Glu Pro Gln<br>            260                    265                 270 | 816 |
| tca aga ttc tgg ggc cat gat aag aac atc ccc acg atc ggc gtc att<br>Ser Arg Phe Trp Gly His Asp Lys Asn Ile Pro Thr Ile Gly Val Ile<br>          275                   280                285 | 864 |
| gcc gtt gtc ttg gct aca cat ctg tgt gat gaa gtc agc ctg gca ggc<br>Ala Val Val Leu Ala Thr His Leu Cys Asp Glu Val Ser Leu Ala Gly<br>290                   295                   300 | 912 |
| ttt ggc tac gac ctc agt caa ccc agg acc cct ctg cac tac ttt gac<br>Phe Gly Tyr Asp Leu Ser Gln Pro Arg Thr Pro Leu His Tyr Phe Asp<br>305                   310                   315                320 | 960 |
| agt cag tgc atg ggc gcc atg cac tgg cag gtc atg cac aat gtg acc<br>Ser Gln Cys Met Gly Ala Met His Trp Gln Val Met His Asn Val Thr<br>                    325                  330                335 | 1008 |
| aca gag acc aag ttc ctc ctg aag ctc ctc aag gag ggc gtg gtg gag<br>Thr Glu Thr Lys Phe Leu Leu Lys Leu Leu Lys Glu Gly Val Val Glu<br>            340                    345                350 | 1056 |
| gac ctc agc ggc ggc atc cac tga<br>Asp Leu Ser Gly Gly Ile His<br>          355 | 1080 |

<210> SEQ ID NO 4
<211> LENGTH: 359
<212> TYPE: PRT

<213> ORGANISM: Mus musculus

<400> SEQUENCE: 4

```
Met Arg Arg Pro Ser Leu Leu Ile Lys Asp Ile Cys Lys Cys Thr Leu
1               5                   10                  15

Val Ala Phe Gly Val Trp Leu Leu Tyr Ile Leu Ile Leu Asn Tyr Thr
            20                  25                  30

Ala Glu Glu Cys Asp Met Lys Arg Met His Tyr Val Asp Pro Asp Arg
        35                  40                  45

Ile Lys Arg Ala Gln Ser Tyr Ala Gln Glu Val Leu Gln Lys Glu Cys
    50                  55                  60

Arg Pro Arg Tyr Ala Lys Thr Ala Met Ala Leu Phe Glu Asp Arg
65                  70                  75                  80

Tyr Ser Ile Asn Leu Glu Pro Phe Val Gln Lys Val Pro Thr Ala Ser
            85                  90                  95

Glu Ala Glu Leu Lys Tyr Asp Pro Pro Phe Gly Phe Arg Lys Phe Ser
        100                 105                 110

Ser Lys Val Gln Ser Leu Leu Asp Met Leu Pro Glu His Asp Phe Ser
    115                 120                 125

Glu His Leu Arg Ala Lys Ala Cys Lys Arg Cys Val Val Gly Asn
130                 135                 140

Gly Gly Ile Leu His Gly Leu Glu Leu Gly His Ala Leu Asn Gln Phe
145                 150                 155                 160

Asp Val Val Ile Arg Leu Asn Ser Ala Pro Val Glu Gly Tyr Ser Glu
            165                 170                 175

His Val Gly Asn Lys Thr Thr Ile Arg Met Thr Tyr Pro Glu Gly Ala
        180                 185                 190

Pro Leu Ser Asp Val Glu Tyr Tyr Ala Asn Asp Leu Phe Val Thr Val
    195                 200                 205

Leu Phe Lys Ser Val Asp Phe Lys Trp Leu Gln Ala Met Val Lys Asn
210                 215                 220

Glu Ser Leu Pro Phe Trp Val Arg Leu Phe Phe Trp Lys Gln Val Ala
225                 230                 235                 240

Glu Lys Val Pro Leu Gln Pro Lys His Phe Arg Ile Leu Asn Pro Val
            245                 250                 255

Ile Ile Lys Glu Thr Ala Phe Asp Ile Leu Gln Tyr Ser Glu Pro Gln
        260                 265                 270

Ser Arg Phe Trp Gly His Asp Lys Asn Ile Pro Thr Ile Gly Val Ile
    275                 280                 285

Ala Val Val Leu Ala Thr His Leu Cys Asp Glu Val Ser Leu Ala Gly
290                 295                 300

Phe Gly Tyr Asp Leu Ser Gln Pro Arg Thr Pro Leu His Tyr Phe Asp
305                 310                 315                 320

Ser Gln Cys Met Gly Ala Met His Trp Gln Val Met His Asn Val Thr
            325                 330                 335

Thr Glu Thr Lys Phe Leu Leu Lys Leu Lys Glu Gly Val Val Glu
        340                 345                 350

Asp Leu Ser Gly Gly Ile His
        355
```

<210> SEQ ID NO 5
<211> LENGTH: 1080
<212> TYPE: DNA
<213> ORGANISM: Mus musculus
<220> FEATURE:
<221> NAME/KEY: CDS
<222> LOCATION: (1)..(1080)
<223> OTHER INFORMATION: Open reading frame

<400> SEQUENCE: 5

| | | | | | | | | | | | | | | | | |
|---|---|---|---|---|---|---|---|---|---|---|---|---|---|---|---|---|
| atg | aga | aga | ccc | agc | ttg | tta | ata | aaa | gac | atc | tgc | aag | tgc | acg | ttg | 48 |
| Met | Arg | Arg | Pro | Ser | Leu | Leu | Ile | Lys | Asp | Ile | Cys | Lys | Cys | Thr | Leu | |
| 1 | | | 5 | | | | | 10 | | | | | 15 | | | |

| | | | | | | | | | | | | | | | | |
|---|---|---|---|---|---|---|---|---|---|---|---|---|---|---|---|---|
| gtt | gca | ttt | gga | gtc | tgg | ctc | ctg | tac | atc | ctc | att | ttg | aat | tac | acc | 96 |
| Val | Ala | Phe | Gly | Val | Trp | Leu | Leu | Tyr | Ile | Leu | Ile | Leu | Asn | Tyr | Thr | |
| | | | 20 | | | | 25 | | | | | 30 | | | | |

| | | | | | | | | | | | | | | | | |
|---|---|---|---|---|---|---|---|---|---|---|---|---|---|---|---|---|
| gct | gaa | gaa | tgt | gac | atg | aaa | aga | atg | cac | tat | gtg | gac | cct | gac | cgg | 144 |
| Ala | Glu | Glu | Cys | Asp | Met | Lys | Arg | Met | His | Tyr | Val | Asp | Pro | Asp | Arg | |
| | | 35 | | | | | 40 | | | | | 45 | | | | |

| | | | | | | | | | | | | | | | | |
|---|---|---|---|---|---|---|---|---|---|---|---|---|---|---|---|---|
| ata | aag | aga | gct | cag | agc | tat | gct | cag | gaa | gtc | ttg | cag | aag | gaa | tgt | 192 |
| Ile | Lys | Arg | Ala | Gln | Ser | Tyr | Ala | Gln | Glu | Val | Leu | Gln | Lys | Glu | Cys | |
| | 50 | | | | | 55 | | | | | 60 | | | | | |

| | | | | | | | | | | | | | | | | |
|---|---|---|---|---|---|---|---|---|---|---|---|---|---|---|---|---|
| cgg | ccc | agg | tac | gcg | aag | acg | gct | atg | gct | ctg | tta | ttt | gag | gac | agg | 240 |
| Arg | Pro | Arg | Tyr | Ala | Lys | Thr | Ala | Met | Ala | Leu | Leu | Phe | Glu | Asp | Arg | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| tac | agc | atc | aac | ttg | gag | cct | ttt | gtg | cag | aag | gtc | ccc | acg | gcc | agt | 288 |
| Tyr | Ser | Ile | Asn | Leu | Glu | Pro | Phe | Val | Gln | Lys | Val | Pro | Thr | Ala | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| gaa | gct | gag | ctc | aag | tat | gac | ccg | cct | ttt | gga | ttc | gg | aag | ttc | tcc | 336 |
| Glu | Ala | Glu | Leu | Lys | Tyr | Asp | Pro | Pro | Phe | Gly | Phe | Arg | Lys | Phe | Ser | |
| | | | | 100 | | | | | 105 | | | | | 110 | | |

| | | | | | | | | | | | | | | | | |
|---|---|---|---|---|---|---|---|---|---|---|---|---|---|---|---|---|
| agt | aaa | gtc | cag | agc | ctc | ttg | gat | atg | ctg | ccc | gaa | cat | gac | ttt | tct | 384 |
| Ser | Lys | Val | Gln | Ser | Leu | Leu | Asp | Met | Leu | Pro | Glu | His | Asp | Phe | Ser | |
| | | | 115 | | | | | 120 | | | | | 125 | | | |

| | | | | | | | | | | | | | | | | |
|---|---|---|---|---|---|---|---|---|---|---|---|---|---|---|---|---|
| gaa | cac | ttg | aga | gcc | aag | gcc | tgc | aag | cgc | tgt | gtg | gtt | gtt | ggg | aac | 432 |
| Glu | His | Leu | Arg | Ala | Lys | Ala | Cys | Lys | Arg | Cys | Val | Val | Val | Gly | Asn | |
| | | 130 | | | | | 135 | | | | | 140 | | | | |

| | | | | | | | | | | | | | | | | |
|---|---|---|---|---|---|---|---|---|---|---|---|---|---|---|---|---|
| ggg | ggc | atc | ctg | cac | gga | cta | gag | ctg | ggt | cac | gcc | ctc | aac | cag | ttc | 480 |
| Gly | Gly | Ile | Leu | His | Gly | Leu | Glu | Leu | Gly | His | Ala | Leu | Asn | Gln | Phe | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gat | gtg | gta | ata | agg | ttg | aac | agt | gcg | cca | gtt | gag | ggt | tac | tct | gaa | 528 |
| Asp | Val | Val | Ile | Arg | Leu | Asn | Ser | Ala | Pro | Val | Glu | Gly | Tyr | Ser | Glu | |
| | | | | 165 | | | | | 170 | | | | | 175 | | |

| | | | | | | | | | | | | | | | | |
|---|---|---|---|---|---|---|---|---|---|---|---|---|---|---|---|---|
| cac | gtt | ggg | aat | aaa | act | act | ata | agg | atg | act | tac | cca | gag | ggt | gcg | 576 |
| His | Val | Gly | Asn | Lys | Thr | Thr | Ile | Arg | Met | Thr | Tyr | Pro | Glu | Gly | Ala | |
| | | | 180 | | | | | 185 | | | | | 190 | | | |

| | | | | | | | | | | | | | | | | |
|---|---|---|---|---|---|---|---|---|---|---|---|---|---|---|---|---|
| cca | ctg | tcg | gac | gtt | gaa | tac | tac | gcc | aat | gat | ttg | ttc | gtt | act | gtt | 624 |
| Pro | Leu | Ser | Asp | Val | Glu | Tyr | Tyr | Ala | Asn | Asp | Leu | Phe | Val | Thr | Val | |
| | | 195 | | | | | 200 | | | | | 205 | | | | |

| | | | | | | | | | | | | | | | | |
|---|---|---|---|---|---|---|---|---|---|---|---|---|---|---|---|---|
| tta | ttt | aag | agt | gtt | gat | ttc | aag | tgg | ctt | caa | gca | atg | gta | aaa | aag | 672 |
| Leu | Phe | Lys | Ser | Val | Asp | Phe | Lys | Trp | Leu | Gln | Ala | Met | Val | Lys | Lys | |
| | 210 | | | | | 215 | | | | | 220 | | | | | |

| | | | | | | | | | | | | | | | | |
|---|---|---|---|---|---|---|---|---|---|---|---|---|---|---|---|---|
| gaa | agc | ctg | ccc | ttt | tgg | gtt | cgc | ctc | ttc | ttt | tgg | aag | caa | gtg | gca | 720 |
| Glu | Ser | Leu | Pro | Phe | Trp | Val | Arg | Leu | Phe | Phe | Trp | Lys | Gln | Val | Ala | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| gaa | aaa | gtc | cca | ctc | cag | cca | aag | cac | ttc | agg | att | ttg | aac | cca | gtt | 768 |
| Glu | Lys | Val | Pro | Leu | Gln | Pro | Lys | His | Phe | Arg | Ile | Leu | Asn | Pro | Val | |
| | | | | 245 | | | | | 250 | | | | | 255 | | |

| | | | | | | | | | | | | | | | | |
|---|---|---|---|---|---|---|---|---|---|---|---|---|---|---|---|---|
| atc | atc | aaa | gaa | act | gcc | ttc | gac | atc | ctt | cag | tac | tca | gag | cct | cag | 816 |
| Ile | Ile | Lys | Glu | Thr | Ala | Phe | Asp | Ile | Leu | Gln | Tyr | Ser | Glu | Pro | Gln | |
| | | | | 260 | | | | | 265 | | | | | 270 | | |

| | | | | | | | | | | | | | | | | |
|---|---|---|---|---|---|---|---|---|---|---|---|---|---|---|---|---|
| tca | aga | ttc | tgg | ggc | cat | gat | aag | aac | atc | ccc | acg | atc | ggc | gtc | att | 864 |
| Ser | Arg | Phe | Trp | Gly | His | Asp | Lys | Asn | Ile | Pro | Thr | Ile | Gly | Val | Ile | |
| | | 275 | | | | | 280 | | | | | 285 | | | | |

| | | | | | | | | | | | | | | | | |
|---|---|---|---|---|---|---|---|---|---|---|---|---|---|---|---|---|
| gcc | gtt | gtc | ttg | gct | aca | cat | ctg | tgt | gat | gaa | gtc | agc | ctg | gca | ggc | 912 |
| Ala | Val | Val | Leu | Ala | Thr | His | Leu | Cys | Asp | Glu | Val | Ser | Leu | Ala | Gly | |
| | 290 | | | | | 295 | | | | | 300 | | | | | |

```
ttt  ggc  tac  gac  ctc  agt  caa  ccc  agg  acc  cct  ctg  cac  tac  ttt  gac       960
Phe  Gly  Tyr  Asp  Leu  Ser  Gln  Pro  Arg  Thr  Pro  Leu  His  Tyr  Phe  Asp
305                      310                      315                      320 agt  cag  tgc  atg  ggc  gcc  atg  cac  tgg  cag  gtc  atg  cac  aat  gtg  acc      1008
Ser  Gln  Cys  Met  Gly  Ala  Met  His  Trp  Gln  Val  Met  His  Asn  Val  Thr
                         325                      330                      335 aca  gag  acc  aag  ttc  ctc  ctg  aag  ctc  ctc  aag  gag  ggc  gtg  gtg  gag      1056
Thr  Glu  Thr  Lys  Phe  Leu  Leu  Lys  Leu  Leu  Lys  Glu  Gly  Val  Val  Glu
                    340                      345                      350 gac  ctc  agc  ggc  ggc  atc  cac  tga                                              1080
Asp  Leu  Ser  Gly  Gly  Ile  His
          355

<210> SEQ ID NO 6
<211> LENGTH: 359
<212> TYPE: PRT
<213> ORGANISM: Mus musculus

<400> SEQUENCE: 6

Met  Arg  Arg  Pro  Ser  Leu  Leu  Ile  Lys  Asp  Ile  Cys  Lys  Cys  Thr  Leu
1                     5                      10                      15

Val  Ala  Phe  Gly  Val  Trp  Leu  Leu  Tyr  Ile  Leu  Ile  Leu  Asn  Tyr  Thr
                20                      25                      30

Ala  Glu  Glu  Cys  Asp  Met  Lys  Arg  Met  His  Tyr  Val  Asp  Pro  Asp  Arg
           35                      40                      45

Ile  Lys  Arg  Ala  Gln  Ser  Tyr  Ala  Gln  Glu  Val  Leu  Gln  Lys  Glu  Cys
      50                      55                      60

Arg  Pro  Arg  Tyr  Ala  Lys  Thr  Ala  Met  Ala  Leu  Leu  Phe  Glu  Asp  Arg
65                      70                      75                      80

Tyr  Ser  Ile  Asn  Leu  Glu  Pro  Phe  Val  Gln  Lys  Val  Pro  Thr  Ala  Ser
                85                      90                      95

Glu  Ala  Glu  Leu  Lys  Tyr  Asp  Pro  Pro  Phe  Gly  Phe  Arg  Lys  Phe  Ser
           100                     105                     110

Ser  Lys  Val  Gln  Ser  Leu  Leu  Asp  Met  Leu  Pro  Glu  His  Asp  Phe  Ser
      115                     120                     125

Glu  His  Leu  Arg  Ala  Lys  Ala  Cys  Lys  Arg  Cys  Val  Val  Val  Gly  Asn
     130                     135                     140

Gly  Gly  Ile  Leu  His  Gly  Leu  Glu  Leu  Gly  His  Ala  Leu  Asn  Gln  Phe
145                     150                     155                     160

Asp  Val  Val  Ile  Arg  Leu  Asn  Ser  Ala  Pro  Val  Glu  Gly  Tyr  Ser  Glu
                165                     170                     175

His  Val  Gly  Asn  Lys  Thr  Thr  Ile  Arg  Met  Thr  Tyr  Pro  Glu  Gly  Ala
           180                     185                     190

Pro  Leu  Ser  Asp  Val  Glu  Tyr  Tyr  Ala  Asn  Asp  Leu  Phe  Val  Thr  Val
      195                     200                     205

Leu  Phe  Lys  Ser  Val  Asp  Phe  Lys  Trp  Leu  Gln  Ala  Met  Val  Lys  Lys
210                     215                     220

Glu  Ser  Leu  Pro  Phe  Trp  Val  Arg  Leu  Phe  Phe  Trp  Lys  Gln  Val  Ala
225                     230                     235                     240

Glu  Lys  Val  Pro  Leu  Gln  Pro  Lys  His  Phe  Arg  Ile  Leu  Asn  Pro  Val
                245                     250                     255

Ile  Ile  Lys  Glu  Thr  Ala  Phe  Asp  Ile  Leu  Gln  Tyr  Ser  Glu  Pro  Gln
           260                     265                     270

Ser  Arg  Phe  Trp  Gly  His  Asp  Lys  Asn  Ile  Pro  Thr  Ile  Gly  Val  Ile
      275                     280                     285

Ala  Val  Val  Leu  Ala  Thr  His  Leu  Cys  Asp  Glu  Val  Ser  Leu  Ala  Gly
```

-continued

```
                    290                 295                 300
     Phe Gly Tyr Asp Leu Ser Gln Pro Arg Thr Pro Leu His Tyr Phe Asp
     305                 310                 315                 320

Ser Gln Cys Met Gly Ala Met His Trp Gln Val Met His Asn Val Thr
                     325                 330                 335

Thr Glu Thr Lys Phe Leu Leu Lys Leu Leu Lys Glu Gly Val Val Glu
                 340                 345                 350

Asp Leu Ser Gly Gly Ile His
                 355

<210> SEQ ID NO 7
<211> LENGTH: 1080
<212> TYPE: DNA
<213> ORGANISM: Mus musculus
<220> FEATURE:
<221> NAME/KEY: CDS
<222> LOCATION: (1)..(1080)
<223> OTHER INFORMATION: Open reading frame

<400> SEQUENCE: 7 atg aga aga ccc agc ttg tta ata aaa gac atc tgc aag tgc acg ttg      48
Met Arg Arg Pro Ser Leu Leu Ile Lys Asp Ile Cys Lys Cys Thr Leu
1               5                   10                  15 gtt gca ttt gga gtc tgg ctc ctg tac atc ctc att ttg aat tac acc      96
Val Ala Phe Gly Val Trp Leu Leu Tyr Ile Leu Ile Leu Asn Tyr Thr
                20                  25                  30 gct gaa gaa tgt gac atg aaa aga atg cac tat gtg gac cct gac cgg     144
Ala Glu Glu Cys Asp Met Lys Arg Met His Tyr Val Asp Pro Asp Arg
            35                  40                  45 ata aag aga gct cag agc tat gct cag gaa gtc ttg cag aag gaa tgt     192
Ile Lys Arg Ala Gln Ser Tyr Ala Gln Glu Val Leu Gln Lys Glu Cys
        50                  55                  60 cgg ccc agg tac gcg aag acg gct atg gct ctg tta ttt gag gac agg     240
Arg Pro Arg Tyr Ala Lys Thr Ala Met Ala Leu Leu Phe Glu Asp Arg
65                  70                  75                  80 tac agc atc aac ttg gag cct ttt gtg cag aag gtc ccc acg gcc agt     288
Tyr Ser Ile Asn Leu Glu Pro Phe Val Gln Lys Val Pro Thr Ala Ser
                85                  90                  95 gaa gct gag ctc aag tat gac ccg cct ttt gga ttc cgg aag ttc tcc     336
Glu Ala Glu Leu Lys Tyr Asp Pro Pro Phe Gly Phe Arg Lys Phe Ser
                100                 105                 110 agt aaa gtc cag agc ctc ttg gat atg ctg ccc gaa cat gac ttt tct     384
Ser Lys Val Gln Ser Leu Leu Asp Met Leu Pro Glu His Asp Phe Ser
            115                 120                 125 gaa cac ttg aga gcc aag gcc tgc aag cgc tgt gtg gtt ggg aac         432
Glu His Leu Arg Ala Lys Ala Cys Lys Arg Cys Val Val Val Gly Asn
        130                 135                 140 ggg ggc atc ctg cac gga cta gag ctg ggt cac gcc ctc aac cag ttc     480
Gly Gly Ile Leu His Gly Leu Glu Leu Gly His Ala Leu Asn Gln Phe
145                 150                 155                 160 gat gtg gta ata agg ttg aac agt gcg cca gtt gag ggt tac tct gaa     528
Asp Val Val Ile Arg Leu Asn Ser Ala Pro Val Glu Gly Tyr Ser Glu
                165                 170                 175 cac gtt ggg aat aaa act act ata agg atg act tac cca gag ggt gcg     576
His Val Gly Asn Lys Thr Thr Ile Arg Met Thr Tyr Pro Glu Gly Ala
            180                 185                 190 cca ctg tcg gac gtt gaa tac tac gcc aat gat ttg ttc gtt act gtt     624
Pro Leu Ser Asp Val Glu Tyr Tyr Ala Asn Asp Leu Phe Val Thr Val
        195                 200                 205 tta ttt aag agt gtt gat ttc aag tgg ctt caa gca atg gta aaa aat     672
Leu Phe Lys Ser Val Asp Phe Lys Trp Leu Gln Ala Met Val Lys Asn
```

```
                    210                 215                 220
gaa agc ctg ccc ttt tgg gtt cgc ctc ttc ttt tgg aag caa gtg gca        720
Glu Ser Leu Pro Phe Trp Val Arg Leu Phe Phe Trp Lys Gln Val Ala
225                 230                 235                 240 gaa aaa gtc cca ctc cag cca aag cac ttc agg att ttg aac cca gtt        768
Glu Lys Val Pro Leu Gln Pro Lys His Phe Arg Ile Leu Asn Pro Val
            245                 250                 255 atc atc aaa gaa act gcc ttc gac atc ctt cag tac tca gag cct cag        816
Ile Ile Lys Glu Thr Ala Phe Asp Ile Leu Gln Tyr Ser Glu Pro Gln
        260                 265                 270 tca aga ttc tgg ggc cat gat aag aac atc ccc acg atc ggc gtc att        864
Ser Arg Phe Trp Gly His Asp Lys Asn Ile Pro Thr Ile Gly Val Ile
    275                 280                 285 gcc gtt gtc ttg gct aca cat ctg tgt gat gaa gtc agc ctg gca ggc        912
Ala Val Val Leu Ala Thr His Leu Cys Asp Glu Val Ser Leu Ala Gly
290                 295                 300 ttt ggc tac gac ctc agt caa ccc agg acc cct ctg cac tac ttt gac        960
Phe Gly Tyr Asp Leu Ser Gln Pro Arg Thr Pro Leu His Tyr Phe Asp
305                 310                 315                 320 agt cag tgc atg ggc gcc atg cac tgg cag gtc atg cac aat gtg cag       1008
Ser Gln Cys Met Gly Ala Met His Trp Gln Val Met His Asn Val Gln
            325                 330                 335 aca gag acc aag ttc ctc ctg aag ctc ctc aag gag ggc gtg gtg gag       1056
Thr Glu Thr Lys Phe Leu Leu Lys Leu Leu Lys Glu Gly Val Val Glu
        340                 345                 350 gac ctc agc ggc ggc atc cac tga                                       1080
Asp Leu Ser Gly Gly Ile His
            355

<210> SEQ ID NO 8
<211> LENGTH: 359
<212> TYPE: PRT
<213> ORGANISM: Mus musculus

<400> SEQUENCE: 8

Met Arg Arg Pro Ser Leu Leu Ile Lys Asp Ile Cys Lys Cys Thr Leu
1               5                   10                  15

Val Ala Phe Gly Val Trp Leu Leu Tyr Ile Leu Ile Leu Asn Tyr Thr
            20                  25                  30

Ala Glu Glu Cys Asp Met Lys Arg Met His Tyr Val Asp Pro Asp Arg
        35                  40                  45

Ile Lys Arg Ala Gln Ser Tyr Ala Gln Glu Val Leu Gln Lys Glu Cys
    50                  55                  60

Arg Pro Arg Tyr Ala Lys Thr Ala Met Ala Leu Leu Phe Glu Asp Arg
65                  70                  75                  80

Tyr Ser Ile Asn Leu Glu Pro Phe Val Gln Lys Val Pro Thr Ala Ser
                85                  90                  95

Glu Ala Glu Leu Lys Tyr Asp Pro Pro Phe Gly Phe Arg Lys Phe Ser
            100                 105                 110

Ser Lys Val Gln Ser Leu Leu Asp Met Leu Pro Glu His Asp Phe Ser
        115                 120                 125

Glu His Leu Arg Ala Lys Ala Cys Lys Arg Cys Val Val Gly Asn
    130                 135                 140

Gly Gly Ile Leu His Gly Leu Glu Leu Gly His Ala Leu Asn Gln Phe
145                 150                 155                 160

Asp Val Val Ile Arg Leu Asn Ser Ala Pro Val Glu Gly Tyr Ser Glu
                165                 170                 175

His Val Gly Asn Lys Thr Thr Ile Arg Met Thr Tyr Pro Glu Gly Ala
```

```
                        180                 185                 190
Pro Leu Ser Asp Val Glu Tyr Tyr Ala Asn Asp Leu Phe Val Thr Val
            195                 200                 205
Leu Phe Lys Ser Val Asp Phe Lys Trp Leu Gln Ala Met Val Lys Asn
210                 215                 220
Glu Ser Leu Pro Phe Trp Val Arg Leu Phe Phe Trp Lys Gln Val Ala
225                 230                 235                 240
Glu Lys Val Pro Leu Gln Pro Lys His Phe Arg Ile Leu Asn Pro Val
                245                 250                 255
Ile Ile Lys Glu Thr Ala Phe Asp Ile Leu Gln Tyr Ser Glu Pro Gln
            260                 265                 270
Ser Arg Phe Trp Gly His Asp Lys Asn Ile Pro Thr Ile Gly Val Ile
            275                 280                 285
Ala Val Val Leu Ala Thr His Leu Cys Asp Glu Val Ser Leu Ala Gly
            290                 295                 300
Phe Gly Tyr Asp Leu Ser Gln Pro Arg Thr Pro Leu His Tyr Phe Asp
305                 310                 315                 320
Ser Gln Cys Met Gly Ala Met His Trp Gln Val Met His Asn Val Gln
                325                 330                 335
Thr Glu Thr Lys Phe Leu Leu Lys Leu Leu Lys Glu Gly Val Val Glu
            340                 345                 350
Asp Leu Ser Gly Gly Ile His
            355

<210> SEQ ID NO 9
<211> LENGTH: 1080
<212> TYPE: DNA
<213> ORGANISM: Mus musculus
<220> FEATURE:
<221> NAME/KEY: CDS
<222> LOCATION: (1)..(1080)
<223> OTHER INFORMATION: Open reading frame

<400> SEQUENCE: 9 atg aga aga ccc agc ttg tta ata aaa gac atc tgc aag tgc acg ttg     48
Met Arg Arg Pro Ser Leu Leu Ile Lys Asp Ile Cys Lys Cys Thr Leu
1               5                   10                  15 gtt gca ttt gga gtc tgg ctc ctg tac atc ctc att ttg aat tac acc     96
Val Ala Phe Gly Val Trp Leu Leu Tyr Ile Leu Ile Leu Asn Tyr Thr
            20                  25                  30 gct gaa gaa tgt gac atg aaa aga atg cac tat gtg gac cct gac cgg    144
Ala Glu Glu Cys Asp Met Lys Arg Met His Tyr Val Asp Pro Asp Arg
        35                  40                  45 ata aag aga gct cag agc tat gct cag gaa gtc ttg cag aag gaa tgt    192
Ile Lys Arg Ala Gln Ser Tyr Ala Gln Glu Val Leu Gln Lys Glu Cys
    50                  55                  60 cgg ccc agg tac gcg aag acg gct atg gct ctg tta ttt gag gac agg    240
Arg Pro Arg Tyr Ala Lys Thr Ala Met Ala Leu Leu Phe Glu Asp Arg
65                  70                  75                  80 tac agc atc aac ttg gag cct ttt gtg cag aag gtc ccc acg gcc agt    288
Tyr Ser Ile Asn Leu Glu Pro Phe Val Gln Lys Val Pro Thr Ala Ser
                85                  90                  95 gaa gct gag ctc aag tat gac ccg cct ttt gga ttc cgg aag ttc tcc    336
Glu Ala Glu Leu Lys Tyr Asp Pro Pro Phe Gly Phe Arg Lys Phe Ser
            100                 105                 110 agt aaa gtc cag agc ctc ttg gat atg ctg ccc gaa cat gac ttt tct    384
Ser Lys Val Gln Ser Leu Leu Asp Met Leu Pro Glu His Asp Phe Ser
        115                 120                 125 gaa cac ttg aga gcc aag gcc tgc aag cgc tgt gtg gtt gtt ggg aac    432
```

```
Glu His Leu Arg Ala Lys Ala Cys Lys Arg Cys Val Val Gly Asn
    130                 135                 140 ggg ggc atc ctg cac gga cta gag ctg ggt cac gcc ctc aac cag ttc      480
Gly Gly Ile Leu His Gly Leu Glu Leu Gly His Ala Leu Asn Gln Phe
145                 150                 155                 160 gat gtg gta ata agg ttg aac agt gcg cca gtt gag ggt tac tct gaa      528
Asp Val Val Ile Arg Leu Asn Ser Ala Pro Val Glu Gly Tyr Ser Glu
                165                 170                 175 cac gtt ggg agc aaa act act ata agg atg act tac cca gag ggt gcg      576
His Val Gly Ser Lys Thr Thr Ile Arg Met Thr Tyr Pro Glu Gly Ala
            180                 185                 190 cca ctg tcg gac gtt gaa tac tac gcc aat gat ttg ttc gtt act gtt      624
Pro Leu Ser Asp Val Glu Tyr Tyr Ala Asn Asp Leu Phe Val Thr Val
        195                 200                 205 tta ttt aag agt gtt gat ttc aag tgg ctt caa gca atg gta aaa aat      672
Leu Phe Lys Ser Val Asp Phe Lys Trp Leu Gln Ala Met Val Lys Asn
    210                 215                 220 gaa agc ctg ccc ttt tgg gtt cgc ctc ttt ttt tgg aag caa gtg gca      720
Glu Ser Leu Pro Phe Trp Val Arg Leu Phe Phe Trp Lys Gln Val Ala
225                 230                 235                 240 gaa aaa gtc cca ctc cag cca aag cac ttc agg att ttg aac cca gtt      768
Glu Lys Val Pro Leu Gln Pro Lys His Phe Arg Ile Leu Asn Pro Val
                245                 250                 255 atc atc aaa gaa act gcc ttc gac atc ctt cag tac tca gag cct cag      816
Ile Ile Lys Glu Thr Ala Phe Asp Ile Leu Gln Tyr Ser Glu Pro Gln
            260                 265                 270 tca aga ttc tgg ggc cat gat aag aac atc ccc acg atc ggc gtc att      864
Ser Arg Phe Trp Gly His Asp Lys Asn Ile Pro Thr Ile Gly Val Ile
        275                 280                 285 gcc gtt gtc ttg gct aca cat ctg tgt gat gaa gtc agc ctg gca ggc      912
Ala Val Val Leu Ala Thr His Leu Cys Asp Glu Val Ser Leu Ala Gly
    290                 295                 300 ttt ggc tac gac ctc agt caa ccc agg acc cct ctg cac tac ttt gac      960
Phe Gly Tyr Asp Leu Ser Gln Pro Arg Thr Pro Leu His Tyr Phe Asp
305                 310                 315                 320 agt cag tgc atg ggc gcc atg cac tgg cag gtc atg cac aat gtg acc     1008
Ser Gln Cys Met Gly Ala Met His Trp Gln Val Met His Asn Val Thr
                325                 330                 335 aca gag acc aag ttc ctc ctg aag ctc ctc aag gag ggc gtg gtg gag     1056
Thr Glu Thr Lys Phe Leu Leu Lys Leu Leu Lys Glu Gly Val Val Glu
            340                 345                 350 gac ctc agc ggc ggc atc cac tga                                     1080
Asp Leu Ser Gly Gly Ile His
        355

<210> SEQ ID NO 10
<211> LENGTH: 359
<212> TYPE: PRT
<213> ORGANISM: Mus musculus

<400> SEQUENCE: 10

Met Arg Arg Pro Ser Leu Leu Ile Lys Asp Ile Cys Lys Cys Thr Leu
1               5                   10                  15

Val Ala Phe Gly Val Trp Leu Leu Tyr Ile Leu Ile Leu Asn Tyr Thr
                20                  25                  30

Ala Glu Glu Cys Asp Met Lys Arg Met His Tyr Val Asp Pro Asp Arg
            35                  40                  45

Ile Lys Arg Ala Gln Ser Tyr Ala Gln Glu Val Leu Gln Lys Glu Cys
        50                  55                  60

Arg Pro Arg Tyr Ala Lys Thr Ala Met Ala Leu Leu Phe Glu Asp Arg
```

```
                 65                  70                  75                  80
Tyr Ser Ile Asn Leu Glu Pro Phe Val Gln Lys Val Pro Thr Ala Ser
                        85                  90                  95

Glu Ala Glu Leu Lys Tyr Asp Pro Pro Phe Gly Phe Arg Lys Phe Ser
                100                 105                 110

Ser Lys Val Gln Ser Leu Leu Asp Met Leu Pro Glu His Asp Phe Ser
                115                 120                 125

Glu His Leu Arg Ala Lys Ala Cys Lys Arg Cys Val Val Gly Asn
    130                 135                 140

Gly Gly Ile Leu His Gly Leu Glu Leu Gly His Ala Leu Asn Gln Phe
145                 150                 155                 160

Asp Val Val Ile Arg Leu Asn Ser Ala Pro Val Glu Gly Tyr Ser Glu
                165                 170                 175

His Val Gly Ser Lys Thr Thr Ile Arg Met Thr Tyr Pro Glu Gly Ala
                180                 185                 190

Pro Leu Ser Asp Val Glu Tyr Tyr Ala Asn Asp Leu Phe Val Thr Val
                195                 200                 205

Leu Phe Lys Ser Val Asp Phe Lys Trp Leu Gln Ala Met Val Lys Asn
    210                 215                 220

Glu Ser Leu Pro Phe Trp Val Arg Leu Phe Phe Trp Lys Gln Val Ala
225                 230                 235                 240

Glu Lys Val Pro Leu Gln Pro Lys His Phe Arg Ile Leu Asn Pro Val
                245                 250                 255

Ile Ile Lys Glu Thr Ala Phe Asp Ile Leu Gln Tyr Ser Glu Pro Gln
                260                 265                 270

Ser Arg Phe Trp Gly His Asp Lys Asn Ile Pro Thr Ile Gly Val Ile
    275                 280                 285

Ala Val Val Leu Ala Thr His Leu Cys Asp Glu Val Ser Leu Ala Gly
    290                 295                 300

Phe Gly Tyr Asp Leu Ser Gln Pro Arg Thr Pro Leu His Tyr Phe Asp
305                 310                 315                 320

Ser Gln Cys Met Gly Ala Met His Trp Gln Val Met His Asn Val Thr
                325                 330                 335

Thr Glu Thr Lys Phe Leu Leu Lys Leu Leu Lys Glu Gly Val Val Glu
                340                 345                 350

Asp Leu Ser Gly Gly Ile His
            355

<210> SEQ ID NO 11
<211> LENGTH: 1080
<212> TYPE: DNA
<213> ORGANISM: Mus musculus
<220> FEATURE:
<221> NAME/KEY: CDS
<222> LOCATION: (1)..(1080)
<223> OTHER INFORMATION: Open reading frame

<400> SEQUENCE: 11 atg aga aga ccc agc ttg tta ata aaa gac atc tgc aag tgc acg ttg      48
Met Arg Arg Pro Ser Leu Leu Ile Lys Asp Ile Cys Lys Cys Thr Leu
1               5                   10                  15 gtt gca ttt gga gtc tgg ctc ctg tac atc ctc att ttg aat tac acc      96
Val Ala Phe Gly Val Trp Leu Leu Tyr Ile Leu Ile Leu Asn Tyr Thr
            20                  25                  30 gct gaa gaa tgt gac atg aaa aga atg cac tat gtg gac cct gac cgg     144
Ala Glu Glu Cys Asp Met Lys Arg Met His Tyr Val Asp Pro Asp Arg
        35                  40                  45
```

```
ata aag aga gct cag agc tat gct cag gaa gtc ttg cag aag gaa tgt       192
Ile Lys Arg Ala Gln Ser Tyr Ala Gln Glu Val Leu Gln Lys Glu Cys
     50                  55                  60 cgg ccc agg tac gcg aag acg gct atg gct ctg tta ttt gag gac agg       240
Arg Pro Arg Tyr Ala Lys Thr Ala Met Ala Leu Leu Phe Glu Asp Arg
 65                  70                  75                  80 tac agc atc aac ttg gag cct ttt gtg cag aag gtc ccc acg gcc agt       288
Tyr Ser Ile Asn Leu Glu Pro Phe Val Gln Lys Val Pro Thr Ala Ser
                 85                  90                  95 gaa gct gag ctc aag tat gac ccg cct ttt gga ttc cgg aag ttc tcc       336
Glu Ala Glu Leu Lys Tyr Asp Pro Pro Phe Gly Phe Arg Lys Phe Ser
            100                 105                 110 agt aaa gtc cag agc ctc ttg gat atg ctg ccc gaa cat gac ttt tct       384
Ser Lys Val Gln Ser Leu Leu Asp Met Leu Pro Glu His Asp Phe Ser
        115                 120                 125 gaa cac ttg aga gcc aag gcc tgc aag cgc tgt gtg gtt ggg aac           432
Glu His Leu Arg Ala Lys Ala Cys Lys Arg Cys Val Val Gly Asn
    130                 135                 140 ggg ggc atc ctg cac gga cta gag ctg ggt cac gcc ctc aac cag ttc       480
Gly Gly Ile Leu His Gly Leu Glu Leu Gly His Ala Leu Asn Gln Phe
145                 150                 155                 160 gat gtg gta ata agg ttg aac agt gcg cca gtt gag ggt tac tct gaa       528
Asp Val Val Ile Arg Leu Asn Ser Ala Pro Val Glu Gly Tyr Ser Glu
                165                 170                 175 gac gtt ggg agc aaa act act ata agg atg act tac cca gag ggt gcg       576
Asp Val Gly Ser Lys Thr Thr Ile Arg Met Thr Tyr Pro Glu Gly Ala
            180                 185                 190 cca ctg tcg gac gtt gaa tac tac gcc aat gat ttg ttc gtt act gtt       624
Pro Leu Ser Asp Val Glu Tyr Tyr Ala Asn Asp Leu Phe Val Thr Val
        195                 200                 205 tta ttt aag agt gtt gat ttc aag tgg ctt caa gca atg gta aaa aat       672
Leu Phe Lys Ser Val Asp Phe Lys Trp Leu Gln Ala Met Val Lys Asn
    210                 215                 220 gaa agc ctg ccc ttt tgg gtt cgc ctc ttt ttt tgg aag caa gtg gca       720
Glu Ser Leu Pro Phe Trp Val Arg Leu Phe Phe Trp Lys Gln Val Ala
225                 230                 235                 240 gaa aaa gtc cca ctc cag cca aag cac ttc agg att ttg aac cca gtt       768
Glu Lys Val Pro Leu Gln Pro Lys His Phe Arg Ile Leu Asn Pro Val
                245                 250                 255 atc atc aaa gaa act gcc ttc gac atc ctt cag tac tca gag cct cag       816
Ile Ile Lys Glu Thr Ala Phe Asp Ile Leu Gln Tyr Ser Glu Pro Gln
            260                 265                 270 tca aga ttc tgg ggc cat gat aag aac atc ccc acg atc ggc gtc att       864
Ser Arg Phe Trp Gly His Asp Lys Asn Ile Pro Thr Ile Gly Val Ile
        275                 280                 285 gcc gtt gtc ttg gct aca cat ctg tgt gat gaa gtc agc ctg gca ggc       912
Ala Val Val Leu Ala Thr His Leu Cys Asp Glu Val Ser Leu Ala Gly
    290                 295                 300 ttt ggc tac gac ctc agt caa ccc agg acc cct ctg cac tac ttt gac       960
Phe Gly Tyr Asp Leu Ser Gln Pro Arg Thr Pro Leu His Tyr Phe Asp
305                 310                 315                 320 agt cag tgc atg ggc gcc atg cac tgg cag gtc atg cac aat gtg acc      1008
Ser Gln Cys Met Gly Ala Met His Trp Gln Val Met His Asn Val Thr
                325                 330                 335 aca gag acc aag ttc ctc ctg aag ctc ctc aag gag ggc gtg gtg gag      1056
Thr Glu Thr Lys Phe Leu Leu Lys Leu Leu Lys Glu Gly Val Val Glu
            340                 345                 350 gac ctc agc ggc ggc atc cac tga                                      1080
Asp Leu Ser Gly Gly Ile His
        355
```

<210> SEQ ID NO 12
<211> LENGTH: 359
<212> TYPE: PRT
<213> ORGANISM: Mus musculus

<400> SEQUENCE: 12

Met Arg Arg Pro Ser Leu Leu Ile Lys Asp Ile Cys Lys Cys Thr Leu
1               5                   10                  15

Val Ala Phe Gly Val Trp Leu Leu Tyr Ile Leu Ile Leu Asn Tyr Thr
            20                  25                  30

Ala Glu Glu Cys Asp Met Lys Arg Met His Tyr Val Asp Pro Asp Arg
        35                  40                  45

Ile Lys Arg Ala Gln Ser Tyr Ala Gln Glu Val Leu Gln Lys Glu Cys
    50                  55                  60

Arg Pro Arg Tyr Ala Lys Thr Ala Met Ala Leu Leu Phe Glu Asp Arg
65                  70                  75                  80

Tyr Ser Ile Asn Leu Glu Pro Phe Val Gln Lys Val Pro Thr Ala Ser
                85                  90                  95

Glu Ala Glu Leu Lys Tyr Asp Pro Pro Phe Gly Phe Arg Lys Phe Ser
            100                 105                 110

Ser Lys Val Gln Ser Leu Leu Asp Met Leu Pro Glu His Asp Phe Ser
        115                 120                 125

Glu His Leu Arg Ala Lys Ala Cys Lys Arg Cys Val Val Gly Asn
    130                 135                 140

Gly Gly Ile Leu His Gly Leu Glu Leu Gly His Ala Leu Asn Gln Phe
145                 150                 155                 160

Asp Val Val Ile Arg Leu Asn Ser Ala Pro Val Glu Gly Tyr Ser Glu
                165                 170                 175

Asp Val Gly Ser Lys Thr Thr Ile Arg Met Thr Tyr Pro Glu Gly Ala
            180                 185                 190

Pro Leu Ser Asp Val Glu Tyr Tyr Ala Asn Asp Leu Phe Val Thr Val
        195                 200                 205

Leu Phe Lys Ser Val Asp Phe Lys Trp Leu Gln Ala Met Val Lys Asn
    210                 215                 220

Glu Ser Leu Pro Phe Trp Val Arg Leu Phe Phe Trp Lys Gln Val Ala
225                 230                 235                 240

Glu Lys Val Pro Leu Gln Pro Lys His Phe Arg Ile Leu Asn Pro Val
                245                 250                 255

Ile Ile Lys Glu Thr Ala Phe Asp Ile Leu Gln Tyr Ser Glu Pro Gln
            260                 265                 270

Ser Arg Phe Trp Gly His Asp Lys Asn Ile Pro Thr Ile Gly Val Ile
        275                 280                 285

Ala Val Val Leu Ala Thr His Leu Cys Asp Glu Val Ser Leu Ala Gly
    290                 295                 300

Phe Gly Tyr Asp Leu Ser Gln Pro Arg Thr Pro Leu His Tyr Phe Asp
305                 310                 315                 320

Ser Gln Cys Met Gly Ala Met His Trp Gln Val Met His Asn Val Thr
                325                 330                 335

Thr Glu Thr Lys Phe Leu Leu Lys Leu Leu Lys Glu Gly Val Val Glu
            340                 345                 350

Asp Leu Ser Gly Gly Ile His
        355

<210> SEQ ID NO 13
<211> LENGTH: 1080

```
<212> TYPE: DNA
<213> ORGANISM: Mus musculus
<220> FEATURE:
<221> NAME/KEY: CDS
<222> LOCATION: (1)..(1080)
<223> OTHER INFORMATION: Open reading frame

<400> SEQUENCE: 13 atg aga aga ccc agc ttg tta ata aaa gac atc tgc aag tgc acg ttg        48
Met Arg Arg Pro Ser Leu Leu Ile Lys Asp Ile Cys Lys Cys Thr Leu
1               5                   10                  15 gtt gca ttt gga gtc tgg ctc ctg tac atc ctc att ttg aat tac acc        96
Val Ala Phe Gly Val Trp Leu Leu Tyr Ile Leu Ile Leu Asn Tyr Thr
            20                  25                  30 gct gaa gaa tgt gac atg aaa aga atg cac tat gtg gac cct gac cgg       144
Ala Glu Glu Cys Asp Met Lys Arg Met His Tyr Val Asp Pro Asp Arg
        35                  40                  45 ata aag aga gct cag agc tat gct cag gaa gtc ttg cag aag gaa tgt       192
Ile Lys Arg Ala Gln Ser Tyr Ala Gln Glu Val Leu Gln Lys Glu Cys
    50                  55                  60 cgg ccc agg tac gcg aag acg gct atg gct ctg tta ttt gag gac agg       240
Arg Pro Arg Tyr Ala Lys Thr Ala Met Ala Leu Leu Phe Glu Asp Arg
65                  70                  75                  80 tac agc atc aac ttg gag cct ttt gtg cag aag gtc ccc acg gcc agt       288
Tyr Ser Ile Asn Leu Glu Pro Phe Val Gln Lys Val Pro Thr Ala Ser
                85                  90                  95 gaa gct gag ctc aag tat gac ccg cct ttt gga ttc cgg aag ttc tcc       336
Glu Ala Glu Leu Lys Tyr Asp Pro Pro Phe Gly Phe Arg Lys Phe Ser
            100                 105                 110 agt aaa gtc cag agc ctc ttg gat atg ctg ccc gaa cat gac ttt tct       384
Ser Lys Val Gln Ser Leu Leu Asp Met Leu Pro Glu His Asp Phe Ser
        115                 120                 125 gaa cac ttg aga gcc aag gcc tgc aag cgc tgt gtg gtt ggg aac            432
Glu His Leu Arg Ala Lys Ala Cys Lys Arg Cys Val Val Gly Asn
    130                 135                 140 ggg ggc atc ctg cac gga cta gag ctg ggt cac gcc ctc aac cag ttc       480
Gly Gly Ile Leu His Gly Leu Glu Leu Gly His Ala Leu Asn Gln Phe
145                 150                 155                 160 gat gtg gta ata agg ttg aac agt gcg cca gtt gag ggt tac tct gaa       528
Asp Val Val Ile Arg Leu Asn Ser Ala Pro Val Glu Gly Tyr Ser Glu
                165                 170                 175 gac gtt ggg aat aaa act act ata agg atg act tac cca gag ggt gcg       576
Asp Val Gly Asn Lys Thr Thr Ile Arg Met Thr Tyr Pro Glu Gly Ala
            180                 185                 190 cca ctg tcg gac gtt gaa tac tac gcc aat gat ttg ttc gtt act gtt       624
Pro Leu Ser Asp Val Glu Tyr Tyr Ala Asn Asp Leu Phe Val Thr Val
        195                 200                 205 tta ttt aag agt gtt gat ttc aag tgg ctt caa gca atg gta aaa aat       672
Leu Phe Lys Ser Val Asp Phe Lys Trp Leu Gln Ala Met Val Lys Asn
    210                 215                 220 gaa agc ctg ccc ttt tgg gtt cgc ctc ttc ttt tgg aag caa gtg gca       720
Glu Ser Leu Pro Phe Trp Val Arg Leu Phe Phe Trp Lys Gln Val Ala
225                 230                 235                 240 gaa aaa gtc cca ctc cag cca aag cac ttc agg att ttg aac cca gtt       768
Glu Lys Val Pro Leu Gln Pro Lys His Phe Arg Ile Leu Asn Pro Val
                245                 250                 255 atc atc aaa gaa act gcc ttc gac atc ctt cag tac tca gag cct cag       816
Ile Ile Lys Glu Thr Ala Phe Asp Ile Leu Gln Tyr Ser Glu Pro Gln
            260                 265                 270 tca aga ttc tgg ggc cat gat aag aac atc ccc acg atc ggc gtc att       864
Ser Arg Phe Trp Gly His Asp Lys Asn Ile Pro Thr Ile Gly Val Ile
        275                 280                 285
```

```
gcc gtt gtc ttg gct aca cat ctg tgt gat gaa gtc agc ctg gca ggc    912
Ala Val Val Leu Ala Thr His Leu Cys Asp Glu Val Ser Leu Ala Gly
290                 295                 300 ttt ggc tac gac ctc agt caa ccc agg acc cct ctg cac tac ttt gac    960
Phe Gly Tyr Asp Leu Ser Gln Pro Arg Thr Pro Leu His Tyr Phe Asp
305                 310                 315                 320 agt cag tgc atg ggc gcc atg cac tgg cag gtc atg cac aat gtg acc   1008
Ser Gln Cys Met Gly Ala Met His Trp Gln Val Met His Asn Val Thr
            325                 330                 335 aca gag acc aag ttc ctc ctg aag ctc ctc aag gag ggc gtg gtg gag   1056
Thr Glu Thr Lys Phe Leu Leu Lys Leu Leu Lys Glu Gly Val Val Glu
340                 345                 350 gac ctc agc ggc ggc atc cac tga                                   1080
Asp Leu Ser Gly Gly Ile His
            355

<210> SEQ ID NO 14
<211> LENGTH: 359
<212> TYPE: PRT
<213> ORGANISM: Mus musculus

<400> SEQUENCE: 14

Met Arg Arg Pro Ser Leu Leu Ile Lys Asp Ile Cys Lys Cys Thr Leu
1               5                   10                  15

Val Ala Phe Gly Val Trp Leu Leu Tyr Ile Leu Ile Leu Asn Tyr Thr
            20                  25                  30

Ala Glu Glu Cys Asp Met Lys Arg Met His Tyr Val Asp Pro Asp Arg
        35                  40                  45

Ile Lys Arg Ala Gln Ser Tyr Ala Gln Glu Val Leu Gln Lys Glu Cys
    50                  55                  60

Arg Pro Arg Tyr Ala Lys Thr Ala Met Ala Leu Leu Phe Glu Asp Arg
65                  70                  75                  80

Tyr Ser Ile Asn Leu Glu Pro Phe Val Gln Lys Val Pro Thr Ala Ser
                85                  90                  95

Glu Ala Glu Leu Lys Tyr Asp Pro Pro Phe Gly Phe Arg Lys Phe Ser
            100                 105                 110

Ser Lys Val Gln Ser Leu Leu Asp Met Leu Pro Glu His Asp Phe Ser
        115                 120                 125

Glu His Leu Arg Ala Lys Ala Cys Lys Arg Cys Val Val Gly Asn
    130                 135                 140

Gly Gly Ile Leu His Gly Leu Glu Leu Gly His Ala Leu Asn Gln Phe
145                 150                 155                 160

Asp Val Val Ile Arg Leu Asn Ser Ala Pro Val Glu Gly Tyr Ser Glu
                165                 170                 175

Asp Val Gly Asn Lys Thr Thr Ile Arg Met Thr Tyr Pro Glu Gly Ala
            180                 185                 190

Pro Leu Ser Asp Val Glu Tyr Tyr Ala Asn Asp Leu Phe Val Thr Val
        195                 200                 205

Leu Phe Lys Ser Val Asp Phe Lys Trp Leu Gln Ala Met Val Lys Asn
    210                 215                 220

Glu Ser Leu Pro Phe Trp Val Arg Leu Phe Phe Trp Lys Gln Val Ala
225                 230                 235                 240

Glu Lys Val Pro Leu Gln Pro Lys His Phe Arg Ile Leu Asn Pro Val
                245                 250                 255

Ile Ile Lys Glu Thr Ala Phe Asp Ile Leu Gln Tyr Ser Glu Pro Gln
            260                 265                 270
```

```
Ser Arg Phe Trp Gly His Asp Lys Asn Ile Pro Thr Ile Gly Val Ile
        275                 280                 285

Ala Val Val Leu Ala Thr His Leu Cys Asp Glu Val Ser Leu Ala Gly
        290                 295                 300

Phe Gly Tyr Asp Leu Ser Gln Pro Arg Thr Pro Leu His Tyr Phe Asp
305                 310                 315                 320

Ser Gln Cys Met Gly Ala Met His Trp Gln Val Met His Asn Val Thr
                325                 330                 335

Thr Glu Thr Lys Phe Leu Leu Lys Leu Leu Lys Glu Gly Val Val Glu
            340                 345                 350

Asp Leu Ser Gly Gly Ile His
            355

<210> SEQ ID NO 15
<211> LENGTH: 1080
<212> TYPE: DNA
<213> ORGANISM: Mus musculus
<220> FEATURE:
<221> NAME/KEY: CDS
<222> LOCATION: (1)..(1080)
<223> OTHER INFORMATION: Open reading frame

<400> SEQUENCE: 15 atg aga aga ccc agc ttg tta ata aaa gac atc tgc aag tgc acg ttg      48
Met Arg Arg Pro Ser Leu Leu Ile Lys Asp Ile Cys Lys Cys Thr Leu
1               5                  10                  15 gtt gca ttt gga gtc tgg ctc ctg tac atc ctc att ttg aat tac acc      96
Val Ala Phe Gly Val Trp Leu Leu Tyr Ile Leu Ile Leu Asn Tyr Thr
                20                  25                  30 gct gaa gaa tgt gac atg aaa aga atg cac tat gtg gac cct gac cgg     144
Ala Glu Glu Cys Asp Met Lys Arg Met His Tyr Val Asp Pro Asp Arg
            35                  40                  45 ata aag aga gct cag agc tat gct cag gaa gtc ttg cag aag gaa tgt     192
Ile Lys Arg Ala Gln Ser Tyr Ala Gln Glu Val Leu Gln Lys Glu Cys
        50                  55                  60 cgg ccc agg tac gcg aag acg gct atg gct ctg tta ttt gag gac agg     240
Arg Pro Arg Tyr Ala Lys Thr Ala Met Ala Leu Leu Phe Glu Asp Arg
65                  70                  75                  80 tac agc atc aac ttg gag cct ttt gtg cag aag gtc ccc acg gcc agt     288
Tyr Ser Ile Asn Leu Glu Pro Phe Val Gln Lys Val Pro Thr Ala Ser
                85                  90                  95 gaa gct gag ctc aag tat gac ccg cct ttt gga ttc cgg aag ttc tcc     336
Glu Ala Glu Leu Lys Tyr Asp Pro Pro Phe Gly Phe Arg Lys Phe Ser
            100                 105                 110 agt aaa gtc cag agc ctc ttg gat atg ctg ccc gaa cat gac ttt tct     384
Ser Lys Val Gln Ser Leu Leu Asp Met Leu Pro Glu His Asp Phe Ser
        115                 120                 125 gaa cac ttg aga gcc aag gcc tgc aag cgc tgt gtg gtt ggg aac         432
Glu His Leu Arg Ala Lys Ala Cys Lys Arg Cys Val Val Val Gly Asn
    130                 135                 140 ggg ggc atc ctg cac gga cta gag ctg ggt cac gcc ctc aac cag ttc     480
Gly Gly Ile Leu His Gly Leu Glu Leu Gly His Ala Leu Asn Gln Phe
145                 150                 155                 160 gat gtg gta ata agg ttg aac agt gcg cca gtt gag ggt tac tct gaa     528
Asp Val Val Ile Arg Leu Asn Ser Ala Pro Val Glu Gly Tyr Ser Glu
                165                 170                 175 gac gtt ggg agc aaa act act ata agg atg act tac cca gag ggt gcg     576
Asp Val Gly Ser Lys Thr Thr Ile Arg Met Thr Tyr Pro Glu Gly Ala
            180                 185                 190 cca ctg tcg gac gtt gaa tac tac gcc aat gat ttg ttc gtt act gtt     624
Pro Leu Ser Asp Val Glu Tyr Tyr Ala Asn Asp Leu Phe Val Thr Val
```

```
tta ttt aag agt gtt gat ttc aag tgg ctt caa gca atg gta aaa aag      672
Leu Phe Lys Ser Val Asp Phe Lys Trp Leu Gln Ala Met Val Lys Lys
210                 215                 220 gaa agc ctg ccc ttt tgg gtt cgc ctc ttc ttt tgg aag caa gtg gca      720
Glu Ser Leu Pro Phe Trp Val Arg Leu Phe Phe Trp Lys Gln Val Ala
225                 230                 235                 240 gaa aaa gtc cca ctc cag cca aag cac ttc agg att ttg aac cca gtt      768
Glu Lys Val Pro Leu Gln Pro Lys His Phe Arg Ile Leu Asn Pro Val
                245                 250                 255 atc atc aaa gaa act gcc ttc gac atc ctt cag tac tca gag cct cag      816
Ile Ile Lys Glu Thr Ala Phe Asp Ile Leu Gln Tyr Ser Glu Pro Gln
        260                 265                 270 tca aga ttc tgg ggc cat gat aag aac atc ccc acg atc ggc gtc att      864
Ser Arg Phe Trp Gly His Asp Lys Asn Ile Pro Thr Ile Gly Val Ile
    275                 280                 285 gcc gtt gtc ttg gct aca cat ctg tgt gat gaa gtc agc ctg gca ggc      912
Ala Val Val Leu Ala Thr His Leu Cys Asp Glu Val Ser Leu Ala Gly
290                 295                 300 ttt ggc tac gac ctc agt caa ccc agg acc cct ctg cac tac ttt gac      960
Phe Gly Tyr Asp Leu Ser Gln Pro Arg Thr Pro Leu His Tyr Phe Asp
305                 310                 315                 320 agt cag tgc atg ggc gcc atg cac tgg cag gtc atg cac aat gtg cag     1008
Ser Gln Cys Met Gly Ala Met His Trp Gln Val Met His Asn Val Gln
                325                 330                 335 aca gag acc aag ttc ctc ctg aag ctc ctc aag gag ggc gtg gtg gag     1056
Thr Glu Thr Lys Phe Leu Leu Lys Leu Leu Lys Glu Gly Val Val Glu
        340                 345                 350 gac ctc agc ggc ggc atc cac tga                                     1080
Asp Leu Ser Gly Gly Ile His
    355
```

<210> SEQ ID NO 16
<211> LENGTH: 359
<212> TYPE: PRT
<213> ORGANISM: Mus musculus

<400> SEQUENCE: 16

```
Met Arg Arg Pro Ser Leu Leu Ile Lys Asp Ile Cys Lys Cys Thr Leu
1               5                   10                  15

Val Ala Phe Gly Val Trp Leu Leu Tyr Ile Leu Ile Leu Asn Tyr Thr
                20                  25                  30

Ala Glu Glu Cys Asp Met Lys Arg Met His Tyr Val Asp Pro Asp Arg
            35                  40                  45

Ile Lys Arg Ala Gln Ser Tyr Ala Gln Glu Val Leu Gln Lys Glu Cys
        50                  55                  60

Arg Pro Arg Tyr Ala Lys Thr Ala Met Ala Leu Leu Phe Glu Asp Arg
65                  70                  75                  80

Tyr Ser Ile Asn Leu Glu Pro Phe Val Gln Lys Val Pro Thr Ala Ser
                85                  90                  95

Glu Ala Glu Leu Lys Tyr Asp Pro Pro Phe Gly Phe Arg Lys Phe Ser
            100                 105                 110

Ser Lys Val Gln Ser Leu Leu Asp Met Leu Pro Glu His Asp Phe Ser
        115                 120                 125

Glu His Leu Arg Ala Lys Ala Cys Lys Arg Cys Val Val Gly Asn
    130                 135                 140

Gly Gly Ile Leu His Gly Leu Glu Leu Gly His Ala Leu Asn Gln Phe
145                 150                 155                 160
```

-continued

```
Asp Val Val Ile Arg Leu Asn Ser Ala Pro Val Glu Gly Tyr Ser Glu
                165                 170                 175

Asp Val Gly Ser Lys Thr Thr Ile Arg Met Thr Tyr Pro Glu Gly Ala
            180                 185                 190

Pro Leu Ser Asp Val Glu Tyr Tyr Ala Asn Asp Leu Phe Val Thr Val
        195                 200                 205

Leu Phe Lys Ser Val Asp Phe Lys Trp Leu Gln Ala Met Val Lys Lys
    210                 215                 220

Glu Ser Leu Pro Phe Trp Val Arg Leu Phe Trp Lys Gln Val Ala
225                 230                 235                 240

Glu Lys Val Pro Leu Gln Pro Lys His Phe Arg Ile Leu Asn Pro Val
                245                 250                 255

Ile Ile Lys Glu Thr Ala Phe Asp Ile Leu Gln Tyr Ser Glu Pro Gln
            260                 265                 270

Ser Arg Phe Trp Gly His Asp Lys Asn Ile Pro Thr Ile Gly Val Ile
        275                 280                 285

Ala Val Val Leu Ala Thr His Leu Cys Asp Glu Val Ser Leu Ala Gly
    290                 295                 300

Phe Gly Tyr Asp Leu Ser Gln Pro Arg Thr Pro Leu His Tyr Phe Asp
305                 310                 315                 320

Ser Gln Cys Met Gly Ala Met His Trp Gln Val Met His Asn Val Gln
                325                 330                 335

Thr Glu Thr Lys Phe Leu Leu Lys Leu Lys Glu Gly Val Val Glu
            340                 345                 350

Asp Leu Ser Gly Gly Ile His
        355

<210> SEQ ID NO 17
<211> LENGTH: 1080
<212> TYPE: DNA
<213> ORGANISM: Mus musculus
<220> FEATURE:
<221> NAME/KEY: CDS
<222> LOCATION: (1)..(1080)
<223> OTHER INFORMATION: Open reading frame

<400> SEQUENCE: 17 atg aga aga ccc agc ttg tta ata aaa gac atc tgc aag tgc acg ttg      48
Met Arg Arg Pro Ser Leu Leu Ile Lys Asp Ile Cys Lys Cys Thr Leu
1               5                   10                  15 gtt gca ttt gga gtc tgg ctc ctg tac atc ctc att ttg aat tac acc      96
Val Ala Phe Gly Val Trp Leu Leu Tyr Ile Leu Ile Leu Asn Tyr Thr
            20                  25                  30 gct gaa gaa tgt gac atg aaa aga atg cac tat gtg gac cct gac cgg     144
Ala Glu Glu Cys Asp Met Lys Arg Met His Tyr Val Asp Pro Asp Arg
        35                  40                  45 ata aag aga gct cag agc tat gct cag gaa gtc ttg cag aag gaa tgt     192
Ile Lys Arg Ala Gln Ser Tyr Ala Gln Glu Val Leu Gln Lys Glu Cys
    50                  55                  60 cgg ccc agg tac gcg aag acg gct atg gct ctg tta ttt gag gac agg     240
Arg Pro Arg Tyr Ala Lys Thr Ala Met Ala Leu Leu Phe Glu Asp Arg
65                  70                  75                  80 tac agc atc aac ttg gag cct ttt gtg cag aag gtc ccc acg gcc agt     288
Tyr Ser Ile Asn Leu Glu Pro Phe Val Gln Lys Val Pro Thr Ala Ser
                85                  90                  95 gaa gct gag ctc aag tat gac ccg cct ttt gga ttc cgg aag ttc tcc     336
Glu Ala Glu Leu Lys Tyr Asp Pro Pro Phe Gly Phe Arg Lys Phe Ser
            100                 105                 110 agt aaa gtc cag agc ctc ttg gat atg ctg ccc gaa cat gac ttt tct     384
```

```
                                               Ser Lys Val Gln Ser Leu Leu Asp Met Leu Pro Glu His Asp Phe Ser
                                                   115                 120                 125 gaa cac ttg aga gcc aag gcc tgc aag cgc tgt gtg gtt gtt ggg aac       432
Glu His Leu Arg Ala Lys Ala Cys Lys Arg Cys Val Val Val Gly Asn
130                 135                 140 ggg ggc atc ctg cac gga cta gag ctg ggt cac gcc ctc aac cag ttc       480
Gly Gly Ile Leu His Gly Leu Glu Leu Gly His Ala Leu Asn Gln Phe
145                 150                 155                 160 gat gtg gta ata agg ttg aac agt gcg cca gtt gag ggt tac tct gaa       528
Asp Val Val Ile Arg Leu Asn Ser Ala Pro Val Glu Gly Tyr Ser Glu
                165                 170                 175 cac gtt ggg aat aaa act act ata agg atg act tac cca gag ggt gcg       576
His Val Gly Asn Lys Thr Thr Ile Arg Met Thr Tyr Pro Glu Gly Ala
            180                 185                 190 cca ctg tcg gac gtt gaa tac tac gcc aat gat ttg ttc gtt act gtt       624
Pro Leu Ser Asp Val Glu Tyr Tyr Ala Asn Asp Leu Phe Val Thr Val
        195                 200                 205 tta ttt aag agt gtt gat ttc aag tgg ctt caa gca atg gta aaa aag       672
Leu Phe Lys Ser Val Asp Phe Lys Trp Leu Gln Ala Met Val Lys Lys
    210                 215                 220 gaa agc ctg ccc ttt tgg gtt cgc ctc ttt ttt tgg aag caa gtg gca       720
Glu Ser Leu Pro Phe Trp Val Arg Leu Phe Phe Trp Lys Gln Val Ala
225                 230                 235                 240 gaa aaa gtc cca ctc cag cca aag cac ttc agg att ttg aac cca gtt       768
Glu Lys Val Pro Leu Gln Pro Lys His Phe Arg Ile Leu Asn Pro Val
                245                 250                 255 atc atc aaa gaa act gcc ttc gac atc ctt cag tac tca gag cct cag       816
Ile Ile Lys Glu Thr Ala Phe Asp Ile Leu Gln Tyr Ser Glu Pro Gln
            260                 265                 270 tca aga ttc tgg ggc cat gat aag aac atc ccc acg atc ggc gtc att       864
Ser Arg Phe Trp Gly His Asp Lys Asn Ile Pro Thr Ile Gly Val Ile
        275                 280                 285 gcc gtt gtc ttg gct aca cat ctg tgt gat gaa gtc agc ctg gca ggc       912
Ala Val Val Leu Ala Thr His Leu Cys Asp Glu Val Ser Leu Ala Gly
    290                 295                 300 ttt ggc tac gac ctc agt caa ccc agg acc cct ctg cac tac ttt gac       960
Phe Gly Tyr Asp Leu Ser Gln Pro Arg Thr Pro Leu His Tyr Phe Asp
305                 310                 315                 320 agt cag tgc atg ggc gcc atg cac tgg cag gtc atg cac aat gtg cag      1008
Ser Gln Cys Met Gly Ala Met His Trp Gln Val Met His Asn Val Gln
                325                 330                 335 aca gag acc aag ttc ctc ctg aag ctc ctc aag gag ggc gtg gtg gag      1056
Thr Glu Thr Lys Phe Leu Leu Lys Leu Leu Lys Glu Gly Val Val Glu
            340                 345                 350 gac ctc agc ggc ggc atc cac tga                                      1080
Asp Leu Ser Gly Gly Ile His
        355

<210> SEQ ID NO 18
<211> LENGTH: 359
<212> TYPE: PRT
<213> ORGANISM: Mus musculus

<400> SEQUENCE: 18

Met Arg Arg Pro Ser Leu Leu Ile Lys Asp Ile Cys Lys Cys Thr Leu
1               5                   10                  15

Val Ala Phe Gly Val Trp Leu Leu Tyr Ile Leu Ile Leu Asn Tyr Thr
                20                  25                  30

Ala Glu Glu Cys Asp Met Lys Arg Met His Tyr Val Asp Pro Asp Arg
            35                  40                  45
```

```
Ile Lys Arg Ala Gln Ser Tyr Ala Gln Glu Val Leu Gln Lys Glu Cys
 50                  55                  60

Arg Pro Arg Tyr Ala Lys Thr Ala Met Ala Leu Phe Glu Asp Arg
 65                  70                  75                  80

Tyr Ser Ile Asn Leu Glu Pro Phe Val Gln Lys Val Pro Thr Ala Ser
                     85                  90                  95

Glu Ala Glu Leu Lys Tyr Asp Pro Pro Phe Gly Phe Arg Lys Phe Ser
                100                 105                 110

Ser Lys Val Gln Ser Leu Leu Asp Met Leu Pro Glu His Asp Phe Ser
                115                 120                 125

Glu His Leu Arg Ala Lys Ala Cys Lys Arg Cys Val Val Val Gly Asn
                130                 135                 140

Gly Gly Ile Leu His Gly Leu Glu Leu Gly His Ala Leu Asn Gln Phe
145                 150                 155                 160

Asp Val Val Ile Arg Leu Asn Ser Ala Pro Val Glu Gly Tyr Ser Glu
                165                 170                 175

His Val Gly Asn Lys Thr Thr Ile Arg Met Thr Tyr Pro Glu Gly Ala
                180                 185                 190

Pro Leu Ser Asp Val Glu Tyr Tyr Ala Asn Asp Leu Phe Val Thr Val
                195                 200                 205

Leu Phe Lys Ser Val Asp Phe Lys Trp Leu Gln Ala Met Val Lys Lys
210                 215                 220

Glu Ser Leu Pro Phe Trp Val Arg Leu Phe Phe Trp Lys Gln Val Ala
225                 230                 235                 240

Glu Lys Val Pro Leu Gln Pro Lys His Phe Arg Ile Leu Asn Pro Val
                245                 250                 255

Ile Ile Lys Glu Thr Ala Phe Asp Ile Leu Gln Tyr Ser Glu Pro Gln
                260                 265                 270

Ser Arg Phe Trp Gly His Asp Lys Asn Ile Pro Thr Ile Gly Val Ile
                275                 280                 285

Ala Val Val Leu Ala Thr His Leu Cys Asp Glu Val Ser Leu Ala Gly
                290                 295                 300

Phe Gly Tyr Asp Leu Ser Gln Pro Arg Thr Pro Leu His Tyr Phe Asp
305                 310                 315                 320

Ser Gln Cys Met Gly Ala Met His Trp Gln Val Met His Asn Val Gln
                325                 330                 335

Thr Glu Thr Lys Phe Leu Leu Lys Leu Leu Lys Glu Gly Val Val Glu
                340                 345                 350

Asp Leu Ser Gly Gly Ile His
                355

<210> SEQ ID NO 19
<211> LENGTH: 34
<212> TYPE: DNA
<213> ORGANISM: Artificial sequence
<220> FEATURE:
<223> OTHER INFORMATION: Description of Artificial Sequence: primer for
      N180Q mutagenesis

<400> SEQUENCE: 19
ctctgaacac gttgggcaga aaactactat aagg                             34

<210> SEQ ID NO 20
<211> LENGTH: 34
<212> TYPE: DNA
<213> ORGANISM: Artificial sequence
<220> FEATURE:
<223> OTHER INFORMATION: Description of Artificial Sequence: primer for
```

N180Q mutagenesis

<400> SEQUENCE: 20
ccttatagta gttttctgcc caacgtgttc agag    34

<210> SEQ ID NO 21
<211> LENGTH: 34
<212> TYPE: DNA
<213> ORGANISM: Artificial sequence
<220> FEATURE:
<223> OTHER INFORMATION: Description of Artificial Sequence: primer for
     N180K mutagenesis

<400> SEQUENCE: 21
ctctgaacac gttgggaaga aaactactat aagg    34

<210> SEQ ID NO 22
<211> LENGTH: 34
<212> TYPE: DNA
<213> ORGANISM: Artificial sequence
<220> FEATURE:
<223> OTHER INFORMATION: Description of Artificial Sequence: primer for
     N180K mutagenesis

<400> SEQUENCE: 22
ccttatagta gttttcttcc caacgtgttc agag    34

<210> SEQ ID NO 23
<211> LENGTH: 34
<212> TYPE: DNA
<213> ORGANISM: Artificial sequence
<220> FEATURE:
<223> OTHER INFORMATION: Description of Artificial Sequence: primer for
     N180S mutagenesis

<400> SEQUENCE: 23
ctctgaacac gttgggagca aaactactat aagg    34

<210> SEQ ID NO 24
<211> LENGTH: 34
<212> TYPE: DNA
<213> ORGANISM: Artificial sequence
<220> FEATURE:
<223> OTHER INFORMATION: Description of Artificial Sequence: primer for
     N180S mutagenesis

<400> SEQUENCE: 24
ccttatagta gttttgctcc caacgtgttc agag    34

<210> SEQ ID NO 25
<211> LENGTH: 42
<212> TYPE: DNA
<213> ORGANISM: Artificial sequence
<220> FEATURE:
<223> OTHER INFORMATION: Description of Artificial Sequence: primer for
     H177D, N180S mutagenesis

<400> SEQUENCE: 25
gagggttact ctgaagacgt tgggagcaaa actactataa gg    42

<210> SEQ ID NO 26
<211> LENGTH: 42
<212> TYPE: DNA
<213> ORGANISM: Artificial sequence
<220> FEATURE:
<223> OTHER INFORMATION: Description of Artificial Sequence: primer for
     H177D, N180S mutagenesis

<400> SEQUENCE: 26
ccttatagta gttttgctcc caacgtcttc agagtaaccc tc                              42

<210> SEQ ID NO 27
<211> LENGTH: 35
<212> TYPE: DNA
<213> ORGANISM: Artificial sequence
<220> FEATURE:
<223> OTHER INFORMATION: Description of Artificial Sequence: primer for
      H177D mutagenesis

<400> SEQUENCE: 27
gagggttact ctgaagacgt tgggaataaa actac                                     35

<210> SEQ ID NO 28
<211> LENGTH: 35
<212> TYPE: DNA
<213> ORGANISM: Artificial sequence
<220> FEATURE:
<223> OTHER INFORMATION: Description of Artificial Sequence: primer for
      H177D mutagenesis

<400> SEQUENCE: 28
gtagttttat tcccaacgtc ttcagagtaa ccctc                                     35

<210> SEQ ID NO 29
<211> LENGTH: 27
<212> TYPE: DNA
<213> ORGANISM: Artificial sequence
<220> FEATURE:
<223> OTHER INFORMATION: Description of Artificial Sequence: primer for
      N224Q mutagenesis

<400> SEQUENCE: 29
gcaatggtaa aacaggaaag cctgccc                                              27

<210> SEQ ID NO 30
<211> LENGTH: 27
<212> TYPE: DNA
<213> ORGANISM: Artificial sequence
<220> FEATURE:
<223> OTHER INFORMATION: Description of Artificial Sequence: primer for
      N224Q mutagenesis

<400> SEQUENCE: 30
gggcaggctt tcctgtttta ccattgc                                              27

<210> SEQ ID NO 31
<211> LENGTH: 27
<212> TYPE: DNA
<213> ORGANISM: Artificial sequence
<220> FEATURE:
<223> OTHER INFORMATION: Description of Artificial Sequence: primer for
      N224K mutagenesis

<400> SEQUENCE: 31
gcaatggtaa aaaaggaaag cctgccc                                              27

<210> SEQ ID NO 32
<211> LENGTH: 27
<212> TYPE: DNA
<213> ORGANISM: Artificial sequence
<220> FEATURE:
<223> OTHER INFORMATION: Description of Artificial Sequence: primer for
      N224K mutagenesis

<400> SEQUENCE: 32

```
gggcaggctt tccttttttta ccattgc                                     27
```

<210> SEQ ID NO 33
<211> LENGTH: 39
<212> TYPE: DNA
<213> ORGANISM: Artificial sequence
<220> FEATURE:
<223> OTHER INFORMATION: Description of Artificial Sequence: primer for
      N224D mutagenesis

<400> SEQUENCE: 33

```
gcttcaagca atggtaaaag atgaaagcct gcccttttg                         39
```

<210> SEQ ID NO 34
<211> LENGTH: 39
<212> TYPE: DNA
<213> ORGANISM: Artificial sequence
<220> FEATURE:
<223> OTHER INFORMATION: Description of Artificial Sequence: primer for
      N224D mutagenesis

<400> SEQUENCE: 34

```
caaaagggca ggctttcatc ttttaccatt gcttgaagc                         39
```

<210> SEQ ID NO 35
<211> LENGTH: 37
<212> TYPE: DNA
<213> ORGANISM: Artificial sequence
<220> FEATURE:
<223> OTHER INFORMATION: Description of Artificial Sequence: primer for
      N334Q mutagenesis

<400> SEQUENCE: 35

```
ctggcaggtc atgcaccagg tgaccacaga gaccaag                           37
```

<210> SEQ ID NO 36
<211> LENGTH: 37
<212> TYPE: DNA
<213> ORGANISM: Artificial sequence
<220> FEATURE:
<223> OTHER INFORMATION: Description of Artificial Sequence: primer for
      N334Q mutagenesis

<400> SEQUENCE: 36

```
cttggtctct gtggtcacct ggtgcatgac ctgccag                           37
```

<210> SEQ ID NO 37
<211> LENGTH: 37
<212> TYPE: DNA
<213> ORGANISM: Artificial sequence
<220> FEATURE:
<223> OTHER INFORMATION: Description of Artificial Sequence: primer for
      N334K mutagenesis

<400> SEQUENCE: 37

```
cttggtctct gtggtcacct tgtgcatgac ctgccag                           37
```

<210> SEQ ID NO 38
<211> LENGTH: 37
<212> TYPE: DNA
<213> ORGANISM: Artificial sequence
<220> FEATURE:
<223> OTHER INFORMATION: Description of Artificial Sequence: primer for
      N334K mutagenesis

<400> SEQUENCE: 38

```
cttggtctct gtggtcacct tgtgcatgac ctgccag                           37
```

```
<210> SEQ ID NO 39
<211> LENGTH: 39
<212> TYPE: DNA
<213> ORGANISM: Artificial sequence
<220> FEATURE:
<223> OTHER INFORMATION: Description of Artificial Sequence: primer for
      T336Q mutagenesis

<400> SEQUENCE: 39
caggtcatgc acaatgtgca gacagagacc aagttcctc                           39

<210> SEQ ID NO 40
<211> LENGTH: 39
<212> TYPE: DNA
<213> ORGANISM: Artificial sequence
<220> FEATURE:
<223> OTHER INFORMATION: Description of Artificial Sequence: primer for
      T336Q mutagenesis

<400> SEQUENCE: 40
gaggaacttg gtctctgtct gcacattgtg catgacctg                           39

<210> SEQ ID NO 41
<211> LENGTH: 364
<212> TYPE: PRT
<213> ORGANISM: Danio rerio

<400> SEQUENCE: 41
```

Met Arg Arg Val Met Lys Gln Ser Ser Cys Tyr Phe Ser Lys Arg Thr
1               5                   10                  15

Met Ile Leu Leu Leu Ser Leu Ala Leu Met Ser Leu Ala Phe Leu Lys
            20                  25                  30

Leu Pro Ser Phe His Thr Glu Leu Lys Pro Val Glu Val Pro Val Asp
        35                  40                  45

Asn Lys Phe Arg Lys Arg Val His Ser His Val Arg Glu Ile Leu Asp
    50                  55                  60

Lys Glu Cys Arg Pro Ser Phe Ala Arg Gln Arg Met Val Thr Glu His
65                  70                  75                  80

His Gly Ser Thr Pro Thr Ile Asp Pro Phe Leu Asn Lys Asn Met Lys
                85                  90                  95

Leu Asp Glu Gln Ile Phe Gln Tyr Pro Pro Pro Phe Gly Phe Leu Asp
            100                 105                 110

Met Lys Lys Lys Leu Glu Glu Ile Leu Asn Leu Leu Pro Val Ser Ser
        115                 120                 125

Glu Gln Arg Leu Gly Glu Arg Asp Cys Arg Arg Cys Val Val Val Gly
    130                 135                 140

Asn Gly Gly Ile Leu Lys Gly Leu Gly Leu Gly His Leu Leu Asn Arg
145                 150                 155                 160

Phe Asp Ile Ile Ile Arg Leu Asn Ser Gly Pro Leu Gln Asp Phe Ser
                165                 170                 175

Ala Asp Val Gly Asn Arg Thr Thr Ile Arg Met Ser Tyr Pro Glu Ser
            180                 185                 190

Cys Pro Lys Val Trp Glu Asp Thr Asp Pro Asp Leu Lys Tyr Val Ala
        195                 200                 205

Val Ile Phe Lys Ser Val Asp Phe His Trp Leu Arg Ala Met Ile Ser
    210                 215                 220

Arg Thr Pro Val Ser Leu Trp Asp Arg Leu Phe Phe Trp Gln Asn Val
225                 230                 235                 240

Pro Met Ser Val Pro Val Lys Thr Ser Gln Phe His Leu Leu Asn Pro

```
                        245                 250                 255
Gln Ile Ile Arg Glu Met Ala Leu Asp Leu Leu Asn Tyr Pro Glu Pro
                260                 265                 270

Lys Lys Arg Leu Trp Ser Trp Asp Gln Asn Ile Pro Thr Leu Gly Leu
            275                 280                 285

Thr Ala Leu Asn Leu Ala Thr Tyr Ile Cys Asp Glu Val Ser Leu Ala
        290                 295                 300

Gly Phe Gly Tyr Asn Leu Ser Gln Lys Glu Ala Pro Leu His Tyr Tyr
305                 310                 315                 320

Asp Ser Val Pro Met Thr Thr Ile Leu Lys Glu Ala Met His Asn Val
                325                 330                 335

Gln Lys Glu Thr Val Phe Leu Lys Arg Leu Val Ala Ser Gly Ser Ile
            340                 345                 350

Thr Asp Leu Thr Gly Gly Ile His Cys Ser Phe Cys
        355                 360

<210> SEQ ID NO 42
<211> LENGTH: 362
<212> TYPE: PRT
<213> ORGANISM: Homo sapiens

<400> SEQUENCE: 42

Met Arg Arg Pro Ser Leu Leu Lys Asp Ile Leu Lys Cys Thr Leu
1               5                   10                  15

Leu Val Phe Gly Val Trp Ile Leu Tyr Ile Leu Lys Leu Asn Tyr Thr
            20                  25                  30

Thr Glu Glu Cys Asp Met Lys Lys Met His Tyr Val Asp Pro Asp His
        35                  40                  45

Val Lys Arg Ala Gln Lys Tyr Ala Gln Val Leu Gln Lys Glu Cys
    50                  55                  60

Arg Pro Lys Phe Ala Lys Thr Ser Met Ala Leu Leu Phe Glu His Arg
65                  70                  75                  80

Tyr Ser Val Asp Leu Leu Pro Phe Val Gln Lys Ala Pro Lys Asp Ser
                85                  90                  95

Glu Ala Glu Ser Lys Tyr Asp Pro Pro Phe Gly Phe Arg Lys Phe Ser
            100                 105                 110

Ser Lys Val Gln Thr Leu Leu Glu Leu Leu Pro Glu His Asp Leu Pro
        115                 120                 125

Glu His Leu Lys Ala Lys Thr Cys Arg Arg Cys Val Val Ile Gly Ser
    130                 135                 140

Gly Gly Ile Leu His Gly Leu Glu Leu Gly His Thr Leu Asn Gln Phe
145                 150                 155                 160

Asp Val Val Ile Arg Leu Asn Ser Ala Pro Val Glu Gly Tyr Ser Glu
                165                 170                 175

His Val Gly Asn Lys Thr Thr Ile Arg Met Thr Tyr Pro Glu Gly Ala
            180                 185                 190

Pro Leu Ser Asp Leu Glu Tyr Tyr Ser Asn Asp Leu Phe Val Ala Val
        195                 200                 205

Leu Phe Lys Ser Val Asp Phe Asn Trp Leu Gln Ala Met Val Lys Lys
    210                 215                 220

Glu Thr Leu Pro Phe Trp Val Arg Leu Phe Phe Trp Lys Gln Val Ala
225                 230                 235                 240

Glu Lys Ile Pro Leu Gln Pro Lys His Phe Arg Ile Leu Asn Pro Val
                245                 250                 255

Ile Ile Lys Glu Thr Ala Phe Asp Ile Leu Gln Tyr Ser Glu Pro Gln
```

```
                    260                 265                 270
Ser Arg Phe Trp Gly Arg Asp Lys Asn Val Pro Thr Ile Gly Val Ile
        275                 280                 285

Ala Val Val Leu Ala Thr His Leu Cys Asp Glu Val Ser Leu Ala Gly
        290                 295                 300

Phe Gly Tyr Asp Leu Asn Gln Pro Arg Thr Pro Leu His Tyr Phe Asp
305                 310                 315                 320

Ser Gln Cys Met Ala Ala Met Asn Phe Gln Thr Met His Asn Val Thr
                325                 330                 335

Thr Glu Thr Lys Phe Leu Leu Lys Leu Val Lys Glu Gly Val Val Lys
                340                 345                 350

Asp Leu Ser Gly Gly Ile Asp Arg Glu Phe
        355                 360

<210> SEQ ID NO 43
<211> LENGTH: 6
<212> TYPE: PRT
<213> ORGANISM: Mus musculus

<400> SEQUENCE: 43

His Val Gly Asn Lys Thr
1               5
```